US012087001B2

(12) United States Patent
Iwase

(10) Patent No.: US 12,087,001 B2
(45) Date of Patent: Sep. 10, 2024

(54) MEDICAL IMAGE PROCESSING APPARATUS, OPTICAL COHERENCE TOMOGRAPHY APPARATUS, MEDICAL IMAGE PROCESSING METHOD, AND COMPUTER-READABLE MEDIUM

(71) Applicant: CANON KABUSHIKI KAISHA, Tokyo (JP)

(72) Inventor: Yoshihiko Iwase, Kanagawa (JP)

(73) Assignee: Canon Kabushiki Kaisha, Tokyo (JP)

(*) Notice: Subject to any disclaimer, the term of this patent is extended or adjusted under 35 U.S.C. 154(b) by 162 days.

(21) Appl. No.: 17/824,038

(22) Filed: May 25, 2022

(65) Prior Publication Data
US 2022/0335633 A1 Oct. 20, 2022

Related U.S. Application Data

(63) Continuation of application No. PCT/JP2020/043963, filed on Nov. 26, 2020.

(30) Foreign Application Priority Data
Nov. 29, 2019 (JP) .................. 2019-216516

(51) Int. Cl.
*G06T 7/38* (2017.01)
*A61B 3/10* (2006.01)
(Continued)

(52) U.S. Cl.
CPC ............... *G06T 7/38* (2017.01); *A61B 3/102* (2013.01); *G06T 7/0012* (2013.01); *G06T 7/579* (2017.01);
(Continued)

(58) Field of Classification Search
CPC ......... G06T 7/38; G06T 7/0012; G06T 7/579; G06T 19/20; G06T 2207/10101;
(Continued)

(56) References Cited

U.S. PATENT DOCUMENTS 8,556,424 B2 10/2013 Iwase et al.
8,634,081 B2 1/2014 Suehira et al.
(Continued)

FOREIGN PATENT DOCUMENTS

JP 2008-209166 A 9/2008
JP 2012-147976 A 8/2012
(Continued)

OTHER PUBLICATIONS

Jun. 9, 2022 International Preliminary Report on Patentability for International Patent Application No. PCT/JP2020/043963.
(Continued)

*Primary Examiner* — Vijay Shankar
(74) *Attorney, Agent, or Firm* — Venable LLP

(57) ABSTRACT

A medical image processing apparatus including an obtaining unit configured to obtain a plurality of tomographic images obtained by radially scanning measuring light on an eye to be examined, and corresponding to a plurality of locations of the eye to be examined, respectively, and an imaging parameter corresponding to each tomographic image, a modifying unit configured to modify a shape of a tomographic image corresponding to the imaging parameter by using the imaging parameter, and an aligning unit configured to align a plurality of shape-modified tomographic images with each other.

18 Claims, 23 Drawing Sheets

(51) Int. Cl.
*G06T 7/00* (2017.01)
*G06T 7/579* (2017.01)
*G06T 19/20* (2011.01)

(52) U.S. Cl.
CPC .... *G06T 19/20* (2013.01); *G06T 2207/10101* (2013.01); *G06T 2207/30041* (2013.01); *G06T 2210/41* (2013.01); *G06T 2219/2004* (2013.01); *G06T 2219/2021* (2013.01)

(58) Field of Classification Search
CPC ....... G06T 2207/30041; G06T 2210/41; G06T 2219/2004; G06T 2219/2021; G06T 2207/20081; G06T 2207/20084; G06T 7/33; A61B 3/102; A61B 3/1225
See application file for complete search history.

(56) References Cited

U.S. PATENT DOCUMENTS

| | | | |
|---|---|---|---|
| 8,657,440 B2 | 2/2014 | Iwase et al. | |
| 9,004,685 B2 | 4/2015 | Iwase et al. | |
| 9,025,844 B2 | 5/2015 | Iwase et al. | |
| 9,082,010 B2 * | 7/2015 | Yonezawa | G06V 40/193 |
| 9,149,181 B2 | 10/2015 | Matsumoto et al. | |
| 10,383,511 B2 | 8/2019 | Iwase et al. | |
| 10,537,243 B2 | 1/2020 | Ikegami | |
| 10,973,406 B2 | 4/2021 | Imamura et al. | |
| 2008/0208525 A1 | 8/2008 | Kikawa et al. | |
| 2011/0137157 A1 | 6/2011 | Imamura et al. | |
| 2013/0071004 A1 * | 3/2013 | Yonezawa | G06V 40/193 |
| | | | 382/133 |
| 2018/0000341 A1 | 1/2018 | Tomatsu et al. | |
| 2021/0106217 A1 | 4/2021 | Higashita | |
| 2021/0158525 A1 * | 5/2021 | Iwase | G06T 7/97 |
| 2022/0183551 A1 | 6/2022 | Tanaka et al. | |

FOREIGN PATENT DOCUMENTS

| | | |
|---|---|---|
| JP | 2012-148003 A | 8/2012 |
| JP | 2018-175258 A | 11/2018 |
| JP | 2019-187551 A | 10/2019 |
| JP | 2021-062077 A | 4/2021 |

OTHER PUBLICATIONS

Yu Tanaka et al., A method for accurate reconstruction of fundus volume data from radially cross-sectional images, MIRU2007, pp. 487-492.

Sep. 12, 2023 Japanese Official Action in Japanese Patent Appln. No. 2019-216516.

* cited by examiner

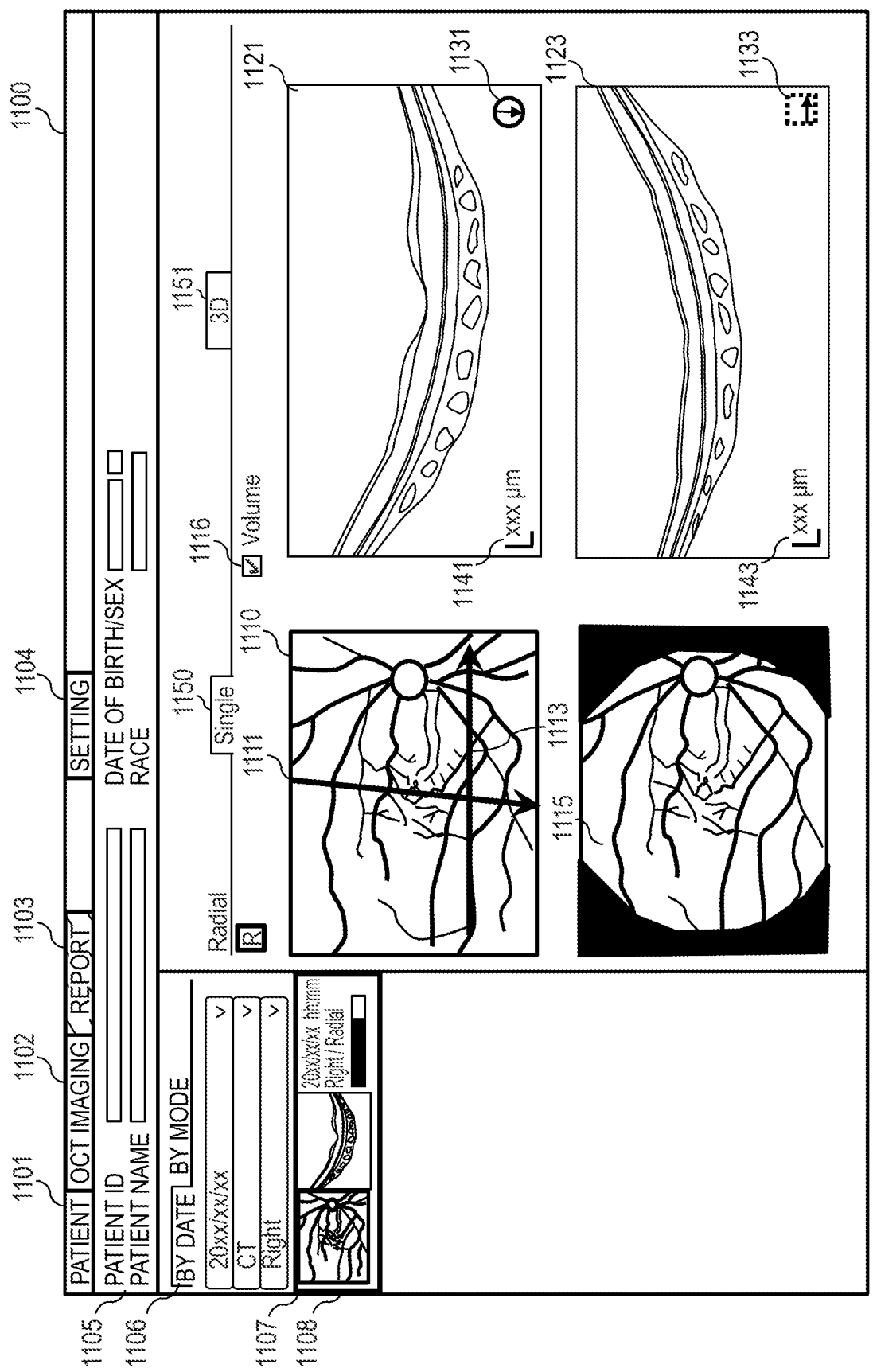

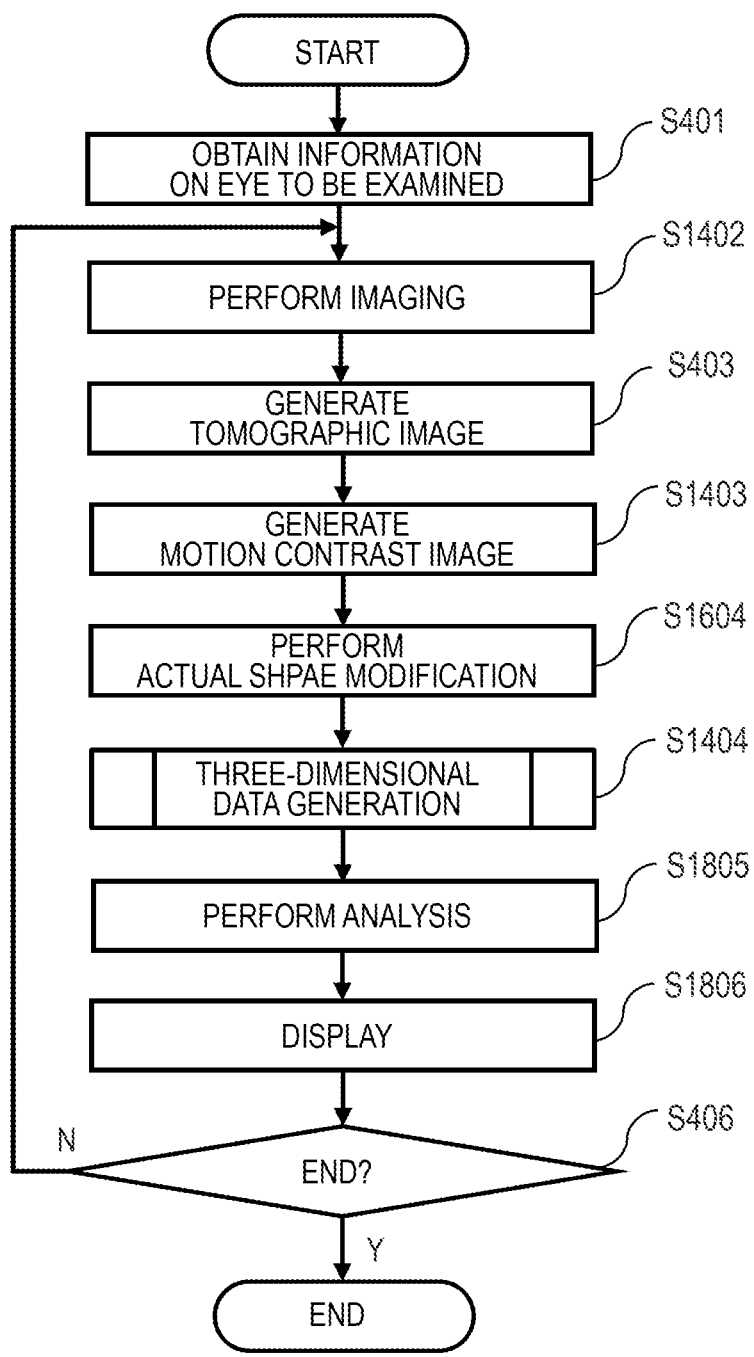

MEDICAL IMAGE PROCESSING APPARATUS, OPTICAL COHERENCE TOMOGRAPHY APPARATUS, MEDICAL IMAGE PROCESSING METHOD, AND COMPUTER-READABLE MEDIUM

CROSS-REFERENCE TO RELATED APPLICATIONS

This application is a Continuation of International Patent Application No. PCT/JP2020/043963, filed Nov. 26, 2020, which claims the benefit of Japanese Patent Application No. 2019-216516, filed Nov. 29, 2019, both of which are hereby incorporated by reference herein in their entirety.

BACKGROUND OF THE INVENTION

Field of the Invention

The present invention relates to a medical image processing apparatus, an optical coherence tomography apparatus, a medical image processing method, and a computer-readable medium.

Description of the Related Art

The state inside a retinal layer can be observed in three dimensions by using a tomographic image imaging apparatus of eyes, such as an OCT apparatus using the optical coherence tomography (OCT). Tomographic image imaging apparatuses have been attracting attention in recent years, since tomographic image imaging apparatuses are useful for more accurately diagnosing diseases. As a form of the OCT, for example, as a method of obtaining an image at high speed, the SD-OCT (Spectral Domain OCT) is known that obtains an interferogram with a spectroscope by using a broadband light source. Additionally, the SS-OCT (Swept Source OCT) is known as a method of measuring the spectrum interference with a single channel photodetector by using a high-speed wavelength swept light source as a light source.

Then, in recent years, the OCT Angiography (OCTA) using the OCT has been proposed as the angiography that does not use a contrast agent. In the OCTA, a blood vessel image (hereinafter referred to as an OCTA image or a motion contrast front image) can be generated by projecting a three-dimensional motion contrast image obtained by using the OCT onto a two-dimensional plane. Here, a motion contrast image is data obtained by repeatedly imaging the same cross section of a measuring object with the OCT, and detecting the changes in the measuring object over time during the imaging. A motion contrast image can be obtained by, for example, calculating the changes over time of the phase, vector, or intensity of a complex OCT signal from differences, ratios, or correlation.

In a case where data of a measuring object is obtained with an OCT apparatus, when an eye to be examined moves, a movement artifact is generated in the data. Therefore, in order to obtain three-dimensional data with the OCT apparatus while reducing the measuring time, Japanese Patent Application Laid-Open No. 2008-209166 discloses a method of obtaining a tomographic image by radially scanning an eye to be examined.

When a retina is radially scanned, a two-dimensional tomographic image of the retina scanned from all directions can be obtained. Therefore, compared to horizontal or vertical scanning, the overall shape of the retina can be grasped with the radial scan.

However, since a plurality of radially scanned two-dimensional tomographic images are obtained at different times, a deviation is generated in the imaging position between adjacent tomographic images. Therefore, it is desired to perform alignment when performing confirmation by comparing between adjacent tomographic images. Therefore, one embodiment of the present invention provides a medical image processing apparatus, an optical coherence tomography apparatus, a medical image processing method, and a computer-readable medium storing a program that can reduce misalignment between a plurality of pieces of data obtained with radial scan.

SUMMARY OF THE INVENTION

A medical image processing apparatus according to one implementation of the present invention includes an obtaining unit configured to obtain a plurality of tomographic images obtained by radially scanning a measuring light on an eye to be examined and corresponding to a plurality of locations of the eye to be examined, respectively, and an imaging parameter corresponding to each tomographic image, a modifying unit configured to modify a shape of a tomographic image corresponding to the imaging parameter by using the imaging parameter, and an aligning unit configured to align a plurality of shape-modified tomographic images with each other.

Further features of the present invention will become apparent from the following description of exemplary embodiments with reference to the attached drawings.

BRIEF DESCRIPTION OF THE DRAWINGS

FIG. 11B illustrates an example of the user interface according to Example 1.

FIG. 18 is a flowchart illustrating an example of a flow of processing according to Example 5.

FIG. 19A illustrates an example of a user interface according to Example 5.

FIG. 19B illustrates an example of the user interface according to Example 5.

DESCRIPTION OF THE EMBODIMENTS

Figure 1:
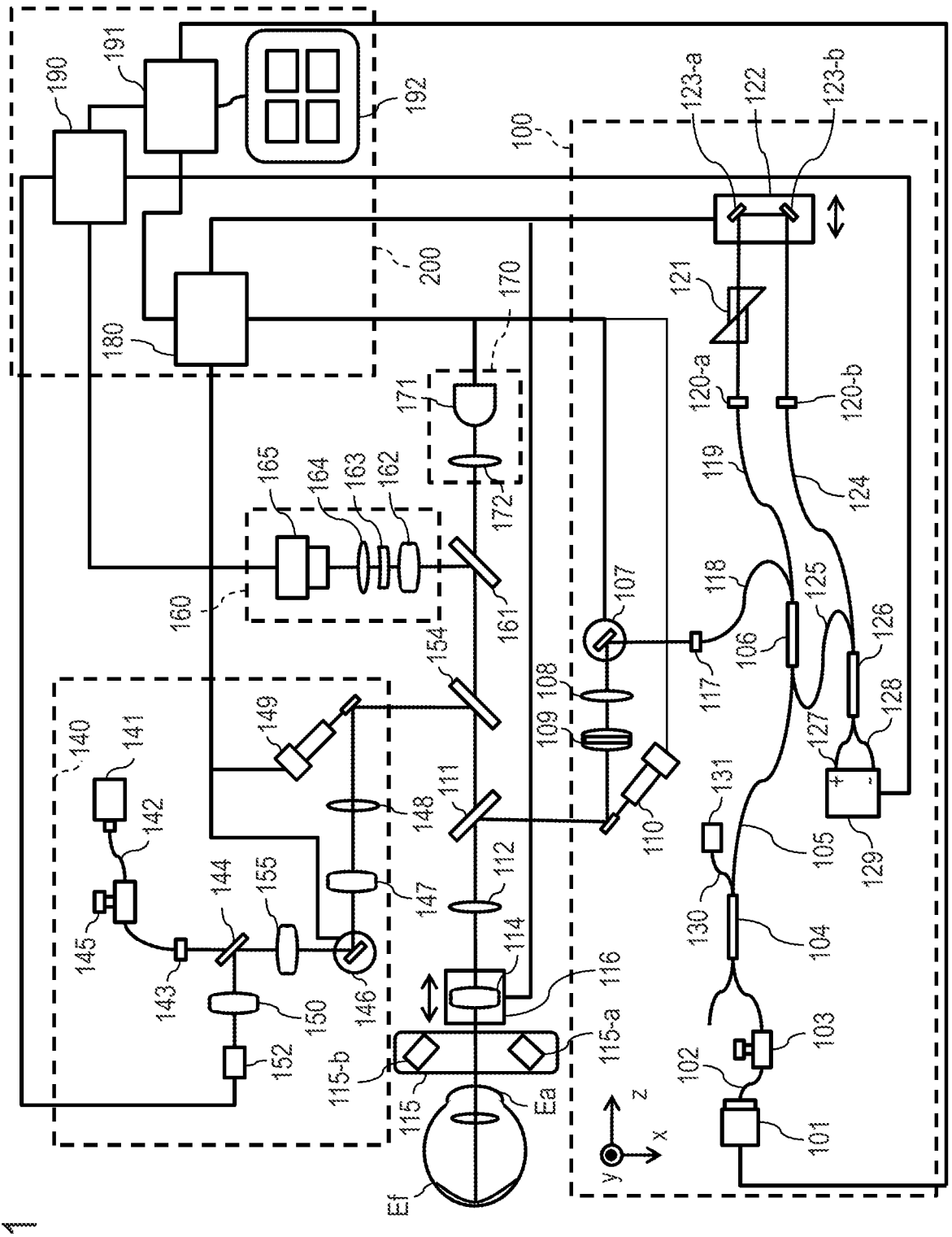
FIG. 1 illustrates an example of a schematic configuration of an optical coherence tomography apparatus according to one embodiment.

Exemplary embodiment and examples of the present invention will now be described in detail in accordance with the accompanying drawings. However, the dimensions, materials, shapes and relative positions of the components described in the following embodiment and examples are not determinate, and can be changed according to a configuration of an apparatus to which the present invention is applied or to various conditions. Further, identical or functionally similar elements are denoted by the same reference numerals in different drawings.

Note that, in the following, the term "machine learning model" refers to a learning model that learned according to a machine learning algorithm. Specific examples of algorithms for machine learning include the nearest-neighbor method, the naive Bayes method, the decision tree, and the support vector machine. Further, deep learning (deep structured learning) which utilizes a neural network to generate, by itself, feature amount and combining weighting factors for learning may also be mentioned.

Algorithms that can be utilized among the aforementioned algorithms can be appropriately used and applied to the embodiments and modifications that are described hereunder. Further, the term "teaching data" refers to training data that is constituted by pairs of input data and output data (ground truth). Furthermore, the term "correct answer data" refers to a ground truth of training data (teaching data).

Note that, the term "learned model" refers to a model which has performed training (learning), with respect to a machine learning model that is in accordance with any machine learning algorithm such as deep learning, using appropriate teaching data (training data) in advance. However, although the learned model is a model obtained using appropriate training data in advance, the learned model is not a model that does not perform further learning, and is a model that can also perform incremental learning. Incremental learning can also be performed after the apparatus is installed at the usage destination.

Here, an optical coherence tomography apparatus (OCT apparatus) that images a subject body, according to one embodiment of the present invention will be described. The OCT apparatus according to the present embodiment includes an irradiation unit that irradiates light having a first wavelength band to a subject body. Here, the first wavelength band is, for example, 400 nm to 700 nm. Additionally, the irradiation unit is, for example, an illumination optical system including an objective lens.

Additionally, the OCT apparatus includes a plane image obtaining unit that obtains a plane image of the subject body based on the return light from the subject body related to the light irradiated by an irradiation means. Further, the OCT apparatus includes an imaging unit that performs imaging of the subject body by, for example, imaging, via an imaging optical system, the return light from the subject body to which the light having the first wavelength band is irradiated. The plane image obtaining unit can obtain a plane image of the subject body based on an output signal of the imaging unit.

Additionally, the OCT apparatus includes a light source that emits laser light while sweeping a second wavelength band that is longer than the first wavelength band. Here, the second wavelength band is, for example, 980 nm to 1100 nm. Additionally, the light source is, for example, a wavelength swept light source of the SS-OCT.

Further, the OCT apparatus includes a tomographic image obtaining unit that obtains a tomographic image of the subject body based on the light obtained by multiplexing the return light from the subject body to which measuring light based on the laser light emitted from the light source is irradiated by an irradiation means, and reference light corresponding to the measuring light. The tomographic image obtaining unit can obtain a tomographic image according to the SS-OCT. Hereinafter, although the OCT apparatus will be described by taking an SS-OCT apparatus as an example, the OCT apparatus is not limited to this. For example, it may be an OCT apparatus with a different imaging system, such as an SD-OCT (Spectral Domain OCT), a PS-OCT (Polarization Sensitive OCT), or an AO-OCT (Adaptive Optics OCT).

Note that the OCT apparatus according to the present invention can be applied to an apparatus that performs measurement of a subject body, such as an eye to be examined, skin, or internal organs. Additionally, when the subject body is a fundus of an eye to be examined, a plane image is a fundus image. In addition, the OCT apparatus according to the present invention, is, for example, an ophthalmic apparatus or an endoscope, and as its example, the ophthalmic apparatus will be described in detail by using the drawings.

Example 1

Hereinafter, referring to FIG. 1 to FIG. 11B, an OCT apparatus according to Example 1 of the present invention will be described. FIG. 1 illustrates a schematic configuration example of the OCT apparatus in the present example. The OCT apparatus is provided with an OCT optical system (SS-OCT optical system) 100, an SLO (Scanning Laser Ophthalmoscope) optical system 140, an anterior ocular segment imaging unit 160, an internal fixation lamp 170, and a controlling apparatus 200.

<Configuration of OCT Optical System>

First, referring to FIG. 1, a configuration of the OCT optical system 100 will be described. The OCT optical system 100 is provided with a light source 101, a polarization controller 103, fiber couplers 104 and 106, and a PM (Power Meter) 131. Additionally, the OCT optical system 100 is provided with a collimator 117, an X scanner 107, lenses 108 and 109, a Y scanner 110, a fiber coupler 126, and a differential detector (balanced receiver) 129. Further, the OCT optical system 100 is provided with collimators 120-a and 120-b, a dispersion compensation glass 121, a coherence gate stage 122, and mirrors 123-a and 123-b.

The light source 101 is a variable wavelength light source, and emits, for example, light having a center wavelength of 1040 nm and a band width of 100 nm. The wavelength of the light emitted from the light source 101 is controlled by the controlling unit 191 of the controlling apparatus 200. More specifically, the wavelength of the light emitted from the light source 101 is swept based on control by the controlling unit 191. Therefore, the controlling unit 191 functions as an example of the controlling unit that controls sweeping of the wavelength of the light emitted from the light source 101. Additionally, the wavelength of the light emitted from the light source 101 can be swept at regular intervals, and can be swept such that the wave numbers (the reciprocal of the wavelength) are equally spaced, due to the calculation restrictions at the time of performing Fourier transform.

The light emitted from the light source 101 is guided to the fiber coupler 104 via a fiber 102 and the polarization controller 103. The fiber coupler 104 divides and emits the incident light to a fiber 130 connected to the PM 131 for measuring the light intensity, and a fiber 105 connected to an optical system for performing OCT measurement. The light emitted from the light source 101 is incident on the PM 131 via the fiber 130. The PM 131 measures the light intensity (power) of the incident light.

The light incident on the fiber 105 is guided to the fiber coupler 106. The fiber coupler 106 divides the incident light into measuring light (also called OCT measuring light) and reference light, emits the measuring light to a fiber 118, and emits the reference light to a fiber 119.

The polarization controller 103 adjusts the state of polarization of the light emitted from the light source 101, and adjusts the polarization state to linear polarization. The division ratio of the fiber coupler 104 is 99:1, and the division ratio of the fiber coupler 106 is 90 (the reference light):10 (the measuring light). Note that the division ratios are not limited to these values, and can be other values.

The measuring light divided by the fiber coupler 106 is emitted as parallel light from the collimator 117 via the fiber 118. The measuring light emitted from the collimator 117 reaches the lens 109 via the X scanner 107 formed from a Galvano mirror that scans the measuring light horizontally (the up-and-down direction of paper) in a fundus Ef, and the lens 108. Further, the measuring light that has passed through the lens 109 reaches a dichroic mirror 111 via the Y scanner 110 formed from a Galvano mirror that scans the measuring light perpendicularly (the depth direction of paper) in the fundus Ef. Additionally, the dichroic mirror 111 has the characteristics of, for example, reflecting light from 950 nm to 1100 nm, and transmitting the other light.

Here, the X scanner 107 and the Y scanner 110 are controlled by a drive controlling unit 180 of the controlling apparatus 200, and form a scanning unit that can scan the region of a desired range on the fundus Ef with the measuring light. Note that the X scanner 107 and the Y scanner 110 may be formed by using other arbitrary deflecting mirrors.

The measuring light reflected by the dichroic mirror 111 reaches a focus lens 114 provided on a stage 116 via the lens 112. The measuring light that has passed through the focus lens 114 reaches a retinal layer of the fundus Ef via an anterior ocular segment Ea of an eye to be examined. The focus lens 114 is moved in an optical axis direction, which is indicated by an arrow in the figure, by the stage 116 controlled by the drive controlling unit 180, and can focus the measuring light to the retinal layer of the fundus Ef. Here, the optical system arranged between the light source 101 and the eye to be examined functions as an example of the illumination optical system that guides the light emitted from the light source 101 to the eye to be examined. The measuring light that has reached the fundus Ef is reflected/scattered by each retinal layer, and returns to the fiber coupler 106 via the above-described optical path. The return light of the measuring light from the fundus Ef reaches the fiber coupler 126 via the fiber 125 from the fiber coupler 106.

On the other hand, the reference light divided by the fiber coupler 106 is emitted as parallel light from the collimator 120-a via the fiber 119. The reference light emitted from the collimator 120-a passes through the dispersion compensation glass 121, and is reflected by the mirrors 123-a and 123-b on the coherence gate stage 122. The reference light reflected by the mirror 123-a and 123-b reaches the fiber coupler 126 via the collimator 120-b and a fiber 124. The coherence gate stage 122 is controlled by the drive controlling unit 180, and can be moved in an optical axis direction indicated by an arrow in the figure. The drive controlling unit 180 can change the optical path length of the reference light by moving the coherence gate stage 122, and can adjust the optical path length of the reference light according to the optical path length of the measuring light, which is different depending on the eye to be examined.

The measuring light and the reference light that have reached the fiber coupler 126 are multiplexed into interference light, and are incident on the differential detector 129, which is a photodetector, via fibers 127 and 128. The differential detector 129 detects the interference light, and outputs an interference signal, which is an electric signal. Here, the optical system arranged between the eye to be examined and the differential detector 129 functions as an example of the imaging optical system that guides the return light from the eye to be examined of the measuring light based on sweep light controlled by the controlling unit 191 to an imaging unit. The interference signal output from the differential detector 129 is analyzed by a signal processing unit 190 of the controlling apparatus 200. Additionally, the photodetector is not limited to the differential detector, and other detectors may be used. The signal processing unit 190 can generate a tomographic image of the eye to be examined, based on the interference signal output from the differential detector 129.

Additionally, although the present example has the configuration in which the measuring light and the reference light interfere with each other in the fiber coupler 126, the configuration is not limited to this. For example, the mirror 123-a may be arranged so as to reflect the reference light to the fiber 119, and the measuring light and the reference light may interfere with each other in the fiber coupler 106. In this case, the fiber coupler 106 is connected to the photodetector, and the mirror 123-b, the collimator 120-b, the fiber 124, and the fiber coupler 126 are not required. Note that an optical circulator can also be used in this case.

<Configuration of SLO Optical System>

Next, a configuration of the SLO optical system 140 will be described. The SLO optical system 140 functions as an example of a fundus image obtaining unit that obtains a fundus image of the eye to be examined. The SLO optical system 140 is provided with a light source 141, a polarization controller 145, a collimator 143, a perforated mirror 144, a lens 155, an X scanner 146, lenses 147 and 148, a Y scanner 149, a lens 150, and an APD (avalanche photodiode) 152.

The light source 141 is, for example, a semiconductor laser, and emits, for example, light having a center wavelength of 780 nm in the present example. The SLO measuring light emitted from the light source 141 passes through a fiber 142, is adjusted to linear polarization by the polarization controller 145, and is emitted as parallel light from the collimator 143. The emitted SLO measuring light passes through a hole of the perforated mirror 144, and reaches the lens 155. The SLO measuring light that has passed through the lens 155 reaches a dichroic mirror 154 via the X scanner 146, the lenses 147 and 148, and the Y scanner 149 formed from a Galvano mirror. Note that the polarization controller 145 may not be provided. The dichroic mirror 154 has the characteristics of, for example, reflecting 760 nm to 800 nm, and transmitting the other light.

Here, the X scanner 146 is formed from a Galvano mirror that horizontally scans the SLO measuring light in the fundus Ef, and the Y scanner 149 is formed from a Galvano mirror that perpendicularly scans the SLO measuring light in the fundus Ef. The X scanner 146 and the Y scanner 149 are controlled by the drive controlling unit 180, and can scan a desired range on the fundus Ef with the SLO measuring light. Not that the X scanner 146 and the Y scanner 149 may be formed by using other arbitrary deflecting mirrors, and, for example, the X scanner 146 may be formed from a polygon mirror or the like.

The SLO measuring light of the linear polarization reflected by the dichroic mirror 154 reaches the fundus Ef via the same optical path as the OCT measuring light in the OCT optical system 100 after passing through the dichroic mirror 111.

The SLO measuring light irradiated on the fundus Ef is reflected/scattered by the fundus Ef, follows the above-described optical path, reaches the perforated mirror 144, and is reflected by the perforated mirror 144. Here, the position of the perforated mirror 144 is conjugate to pupil position of the eye to be examined, and among the reflected/scattered light of the SLO measuring light irradiated on the fundus Ef, the light that has passed through the pupil periphery is reflected by the perforated mirror 144. The light reflected by the perforated mirror 144 reaches the APD 152 via the lens 150, and is received by the APD 152. The APD 152 converts the return light of the received SLO measuring light into an electric signal, and outputs the electric signal to the signal processing unit 190. The signal processing unit 190 can generate a fundus image, which is a front image of the eye to be examined, based on the output from the APD 152.

<Configuration of Anterior Ocular Segment Imaging Unit>

Next, a configuration of the anterior ocular segment imaging unit 160 will be described. The anterior ocular segment imaging unit 160 is provided with lenses 162, 163, and 164 and an anterior ocular segment camera 165. When imaging is performed by the anterior ocular segment imaging unit 160, for example, an illumination light source 115, which includes LEDs 115-a and 115-b that emit illumination light having a wavelength of 850 nm, irradiates an anterior ocular segment Ea with illumination light The light reflected by the anterior ocular segment Ea reaches a dichroic mirror 161 via the focus lens 114, the lens 112, and the dichroic mirrors 111 and 154. The dichroic mirror 161 has the characteristics of, for example, reflecting light of 820 nm to 900 nm, and transmitting the other light. Note that the illumination light source 115 may be controlled by the drive controlling unit 180.

The light reflected by the dichroic mirror 161 reaches the anterior ocular segment camera 165 via the lenses 162, 163, and 164, and is received by the anterior ocular segment camera 165. The anterior ocular segment camera 165 converts the received light into an electric signal, and outputs the electric signal to the signal processing unit 190. The signal processing unit 190 can generate an anterior ocular segment image of the eye to be examined, based on the output from the anterior ocular segment camera 165.

<Regarding Configuration of Internal Fixation Lamp>

Next, the internal fixation lamp 170 will be described. The internal fixation lamp 170 is provided with a fixation lamp display unit 171 and a lens 172. For example, a plurality of light emitting diodes (LDs) arranged in a matrix can be used as the fixation lamp display unit 171. The lighting positions of the light emitting diodes are changed according to a site to be imaged under the control of the drive controlling unit 180. The light from the fixation lamp display unit 171 is guided to the eye to be examined via the lens 172. The light emitted from the fixation lamp display unit 171 has a wavelength of, for example, 520 nm. Additionally, as the fixation lamp, a desired pattern can be displayed under the control of the drive controlling unit 180.

The alignment of the apparatus can be performed by using an anterior ocular segment image of the eye to be examined observed by the anterior ocular segment imaging unit 160 in a state where the internal fixation lamp 170 is turned on, and the eye to be examined is made to gaze the internal fixation lamp 170. Note that the alignment may be automatically performed by analyzing the anterior ocular segment image by the controlling apparatus 200, or may be manually performed by presenting the anterior ocular segment image to an operator. After the completion of the alignment, the imaging of the fundus using the OCT optical system 100 and the SLO optical system 140 can be performed.

<Regarding Configuration of Controlling Apparatus>

Next, a controlling apparatus 200 (medical image processing apparatus) will be described. The controlling apparatus 200 is provided with the drive controlling unit 180, the signal processing unit 190, the controlling unit 191, and a display unit 192. As described above, the drive controlling unit 180 controls the components such as the OCT optical system 100, the SLO optical system 140, the anterior ocular segment imaging unit 160, and the X scanner 107 in the internal fixation lamp 170.

The signal processing unit 190 performs generation of an image, analysis of the generated image, generation of visualized information of an analysis result, etc., based on signals output from the differential detector 129, the APD 152, and the anterior ocular segment camera 165, respectively. Note that the details of the generation processing of an image, etc., will be described later.

The controlling unit 191 controls the entire OCT apparatus, and displays an image generated by the signal processing unit 190, etc., on a display screen of the display unit 192. Note that image data generated by the signal processing unit 190 may be transmitted to the controlling unit 191 by wire, or may be transmitted to the controlling unit 191 wirelessly.

The display unit 192 may be formed from, for example, an arbitrary monitor such as a display of liquid crystal, and functions as an example of a display apparatus. Under the control of the controlling unit 191, the display unit 192 displays various kinds of information as will be described later. Note that image data from the controlling unit 191 may be transmitted to the display unit 192 by wire, or may be transmitted to the display unit 192 wirelessly. Additionally, the display unit 192, the controlling unit 191, etc., are included in the controlling apparatus 200, but may be provided separately from the controlling apparatus 200. Note that the controlling apparatus 200 may be configured as a dedicated computer for the OCT apparatus, or may be configured by using a general computer. Additionally, the drive controlling unit 180, the signal processing unit 190, and the controlling unit 191 may be configured with a software module executed by a CPU of the controlling apparatus 200, or may be configured with a circuit realizing specific functions, such as an ASIC, or with an independent apparatus, etc.

Additionally, the controlling unit 191 and the display unit 192 may be integrally formed, and may be formed as, for example, a tablet computer, which is an apparatus that can be carried by a user. In this case, a touch-panel function can be installed in the display unit 192, and a touch panel can be configured to allow operations such as moving the display position of an image, scaling, and changing of the displayed image. Note that the touch-panel function may be installed in the display unit 192 even when the controlling unit 191 and the display unit 192 are not integrally formed, and a touch panel may be used as an instruction apparatus. Additionally, the controlling apparatus 200 may be connected to an instruction apparatus not illustrated, and may be connected to, for example, a mouse and a keyboard.

Figure 2:
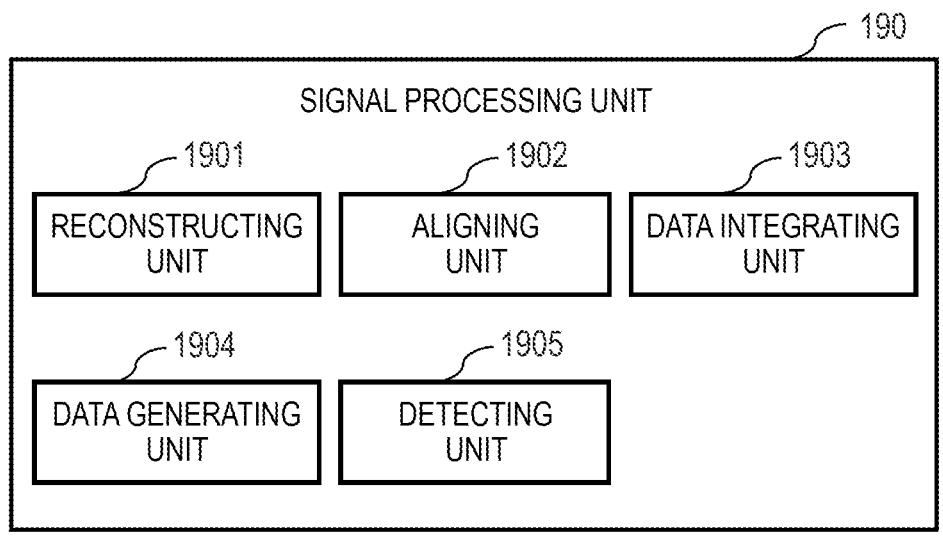
FIG. 2 illustrates an example of a schematic configuration of a signal processing unit according to Example 1.

Next, referring to FIG. 2, the image generation and image analysis in the signal processing unit 190 will be described. FIG. 2 illustrates a schematic configuration example of the signal processing unit 190. The signal processing unit 190 is provided with a reconstructing unit 1901, an aligning unit 1902, a data integrating unit 1903, a data generating unit 1904, and a detecting unit 1905.

The reconstructing unit 1901 in the signal processing unit 190 generates a tomographic image by performing general reconstruction processing that includes wave number conversion, fast Fourier transform (FFT), and absolute value conversion (obtaining of amplitude) on the interference signal output from the differential detector 129. Note that the method of reconstruction processing is not limited to this, and known arbitrary methods may be used.

Figure 3A:
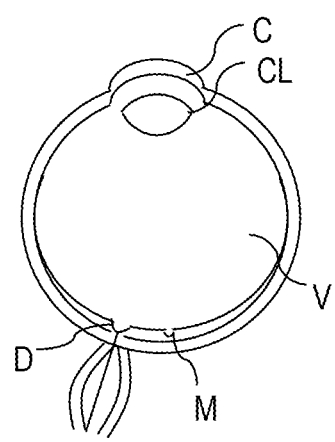
FIG. 3A is a diagram for describing a structure of an eye.

Here, referring to FIG. 3A to FIG. 3C, a tomographic image imaged by using the OCT optical system 100 and generated by the reconstructing unit 1901, a fundus image imaged by using the SLO optical system 140 and generated by the signal processing unit 190, and the structure of an eye will be described. FIG. 3A illustrates a schematic diagram of an eyeball. In FIG. 3A, a cornea C, a crystalline lens CL, a vitreous body V, a macular area M (the center portion of a macular represents a fovea), and an optic nerve head D are illustrated. Hereinafter, a case will be described in which the posterior pole of the retina, mainly including the vitreous body, the macular area, and the optic nerve head, is imaged by using the OCT optical system 100. Note that, although a description is omitted, the anterior ocular segment of the cornea and the crystalline lens can also be imaged by using the OCT optical system 100.

Figure 3B:
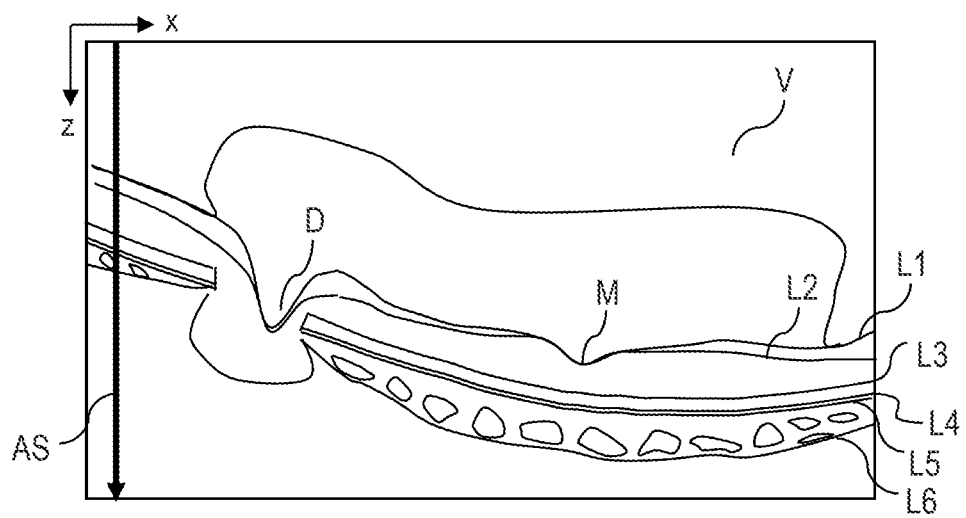
FIG. 3B is a diagram for describing a tomographic image.

FIG. 3B illustrates an example of a tomographic image in a case where the retina is imaged by using the OCT optical system 100. In FIG. 3B, AS represents the unit of obtaining image in an OCT tomographic image called A-scan, and a tomographic image in the depth direction at one point of a fundus can be obtained with one A-scan. Single B-scan is formed by repeating this A-scan, while scanning the measuring light for one transverse direction of the fundus. Therefore, by performing single B-scan, one B-scan image, which is a collection of a plurality of A-scan images obtained by A-scan, can be obtained. Here, a B-scan image is called a two-dimensional tomographic image (or tomographic view).

In FIG. 3B, the vitreous body V, the macular area M, and the optic nerve head D are illustrated. Additionally, in FIG. 3B, a boundary L1 between an inner limiting membrane (ILM) and a nerve fiber layer (NFL), a boundary L2 between the nerve fiber layer and a ganglion cell layer (GCL), a photoreceptor inner segment-outer segment junction (ISOS) L3, a retinal pigment epithelium (RPE) L4, a Bruch's membrane (BM) L5, and a choroid L6 are illustrated. Note that, in the example of the tomographic image illustrated in FIG. 3B, a horizontal axis (scanning direction (B-scan direction) of OCT) is an x axis, and a vertical axis (depth direction) is a z axis.

Figure 3C:
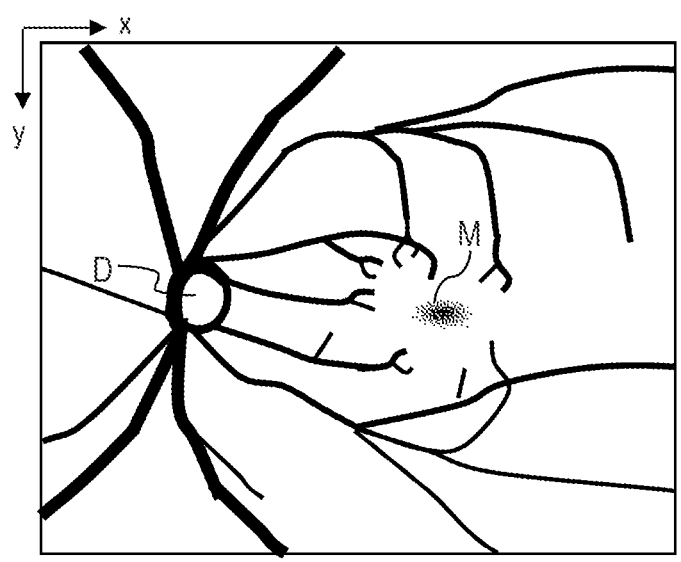
FIG. 3C is a diagram for describing a fundus image.

FIG. 3C illustrates an example of a fundus image obtained by using the SLO optical system 140. The SLO optical system 140 is an optical system for imaging fundus images of an eye. Note that the SLO optical system 140 may be provided as an SLO apparatus. Note that a fundus camera, etc., may be provided as an apparatus for obtaining fundus images.

In FIG. 3C, the macular area M and the optic nerve head D are illustrated, and a thick curve in FIG. 3C represents a retinal blood vessel. In a fundus image, let a horizontal axis be an x axis, and a vertical axis be a y axis. Note that the apparatus configuration related to the OCT optical system 100 and the SLO optical system 140 may be of an integral type or may be of a separated type.

Figure 4A:
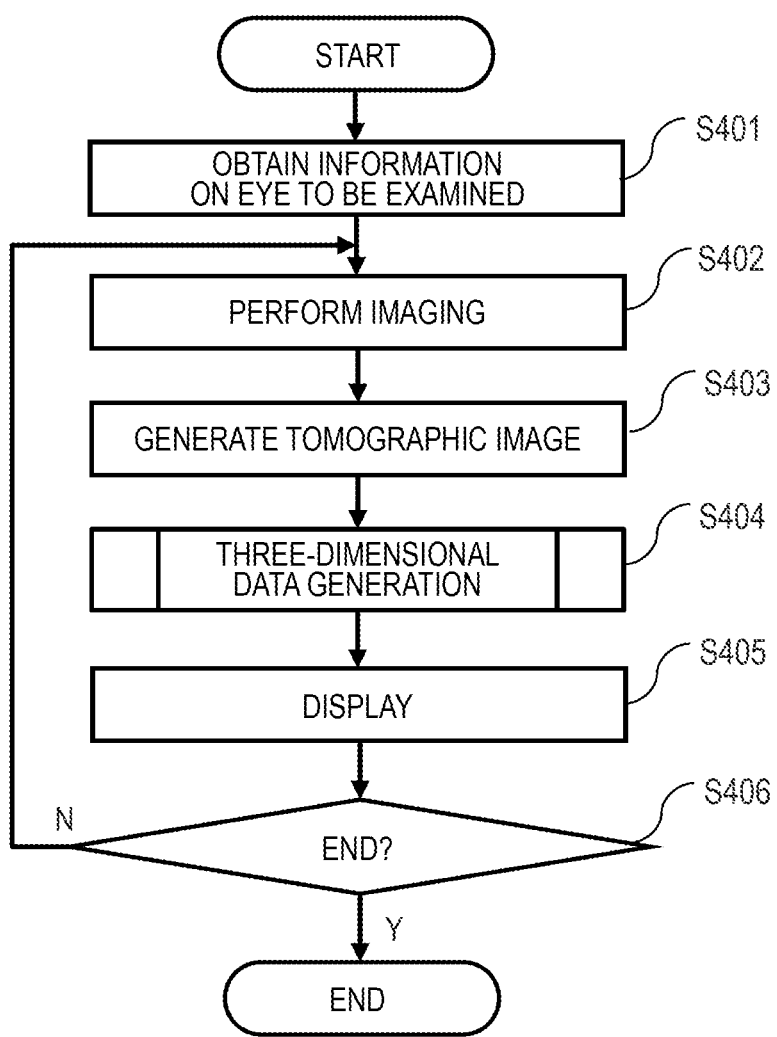
FIG. 4A is a flowchart illustrating an example of a flow of processing according to Example 1.
Figure 4B:
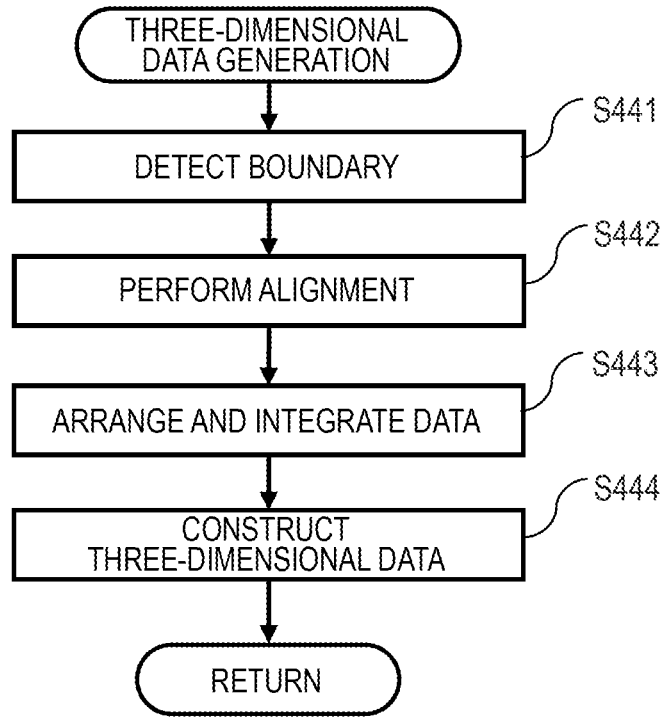
FIG. 4B is a flowchart illustrating an example of a flow of three-dimensional data generation processing according to Example 1.

Next, referring to FIG. 4A and FIG. 4B, a processing procedure of the controlling apparatus 200 according to the present example will be illustrated. FIG. 4A is a flowchart illustrating a flow of a series of operational processing according to the present example, and FIG. 4B is a flowchart illustrating a flow of three-dimensional data generation processing according to the present example. When the series of operational processing according to the present example is started, the processing proceeds to step S401.

<Step S401>

In step S401, the controlling apparatus 200 obtains a subject identification number from the outside as information for identifying an eye to be examined. In addition, the subject identification number may be input by the operator via the input unit of a not shown. The controlling apparatus 200 obtains the information on the eye to be examined concerned which the external memory part of a not shown holds based on the subject identification number, and stores it to the storage of a not shown. Note that a storage may be an arbitrary memory or a storage medium provided in the controlling apparatus 200.

<Step S402>

In step S402, imaging is performed by scanning an eye to be examined. The scanning of the eye to be examined may be performed according to an instruction to start scanning by an operator. When the instruction to start scanning is input, the controlling apparatus 200 controls the operations of the X scanner 107 and the Y scanner 110 by the drive controlling unit 180, and performs scanning of the eye to be examined by using the OCT optical system 100.

When the respective orientations of the X scanner 107 and the Y scanner 110 are changed, the measuring light can be scanned in each direction of the horizontal direction (X) and the vertical direction (Y) in an apparatus coordinate system. Therefore, by changing the orientations of the X scanner 107 and the Y scanner 110 at the same time, scanning can be performed in the direction obtained by combining the horizontal direction and the vertical direction, and the measuring light can be scanned in arbitrary directions on a fundus plane.

The controlling unit 191 of the controlling apparatus 200 performs adjustment of various imaging parameters when performing imaging. Specifically, the controlling unit 191 sets at least the parameters related to the position of the internal fixation lamp 170, a scan range, a scan pattern, a coherence gate position, and focusing. Based on the set imaging parameters, the drive controlling unit 180 controls the light emitting diodes of the fixation lamp display unit 171 to control the position of the internal fixation lamp 170 so as to perform imaging at a desired location, such as the macular area or the optic nerve head. Note that the operator can instruct the position of the internal fixation lamp 170 by using a user interface not illustrated, and the controlling unit 191 can set the position of the internal fixation lamp 170 according to an instruction from the operator.

Additionally, the controlling unit 191 according to the present example sets a scan pattern of radial scan as the scan pattern. In addition, the controlling unit 191 can also set the number and positions of scanning lines for radial scan, and the order of scanning as the imaging parameters. Note that the controlling unit 191 may set these imaging parameters according to an instruction from the operator, or may automatically set the imaging parameters that are set for each predetermined imaging mode. After the adjustment of these imaging parameters ends, when the operator gives an instruction, such as selecting start imaging, which is not illustrated, the controlling apparatus 200 starts imaging of the eye to be examined.

Here, referring to FIG. 5A to FIG. 5D, radial scan in the present example will be described. FIG. 5A to FIG. 5D illustrate examples of the scanning lines for radial scan. Arrows indicate the directions to be scanned. Note that the directions to be scanned may not be the directions illustrated in the figures, but may be the opposite directions.

Figure 5A:
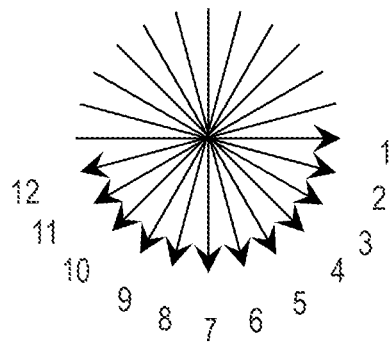
FIG. 5A is a diagram for describing an example of a scanning state according to Example 1.
Figure 5B:
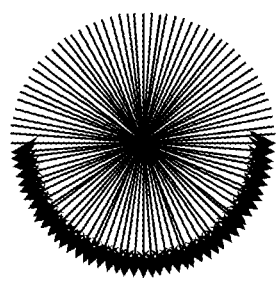
FIG. 5B is a diagram for describing an example of the scanning state according to Example 1.

Although 12 scanning lines are illustrated in FIG. 5A for convenience of description, when aiming at building three-dimensional data from radial scan, it is better to set the scanning lines densely as illustrated in FIG. 5B, and the number n of the scanning lines can be set to 90 or more. When the number n of the scanning lines is 90, it means that a circular area having 360 degrees is scanned at 2 degree intervals. When the number n of the scanning lines n is 12, it is a 15-degree interval, and thus the density of imaging can be increased by increasing n.

Figure 5C:
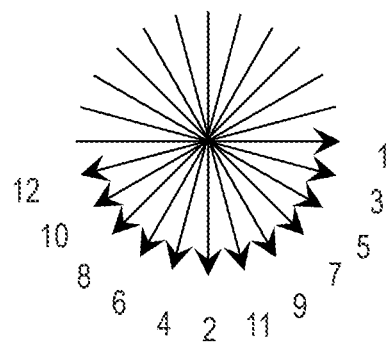
FIG. 5C is a diagram for describing an example of the scanning state according to Example 1.
Figure 5D:
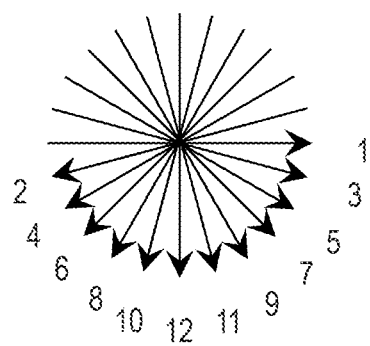
FIG. 5D is a diagram for describing an example of the scanning state according to Example 1.

Further, the order of performing the radial scan need not be the order of adjacent scanning lines as illustrated in FIG. 5A, and may be an arbitrary order, for example, the order as illustrated in FIG. 5C or FIG. 5D. The example illustrated in FIG. 5C is an example of performing scanning in order at 90 degree intervals. Additionally, the example illustrated in FIG. 5D is an example of performing scanning such that the time difference between adjacent scanning lines becomes the smallest, and is an example of alternately scanning the scanning lines that are earlier in the order and the scanning lines that are later in the order, with respect to the order of the adjacent scanning lines as illustrated in FIG. 5A. For example, in the example illustrated in FIG. 5A, although the scanning lines are adjacent to each other in the first scan and the twelfth scan, the time for performing scanning on the scanning lines becomes relatively long since 11 times of scanning is included in between. On the other hand, in the example illustrated in FIG. 5D, the time interval for performing scanning on the adjacent scanning lines only takes the time required for two scans at most. The misalignment between adjacent tomographic images obtained by performing scanning on adjacent scanning lines can be reduced by shortening the time interval for the adjacent scanning lines. Note that, by changing the order of the scanning lines in the radial scan, advantages can be expected such as blood flow measurement can be conducted more appropriately for, for example, a person with a high blood flow velocity.

<Step S403>

In step S403, the reconstructing unit 1901 generates a tomographic image by performing the above-described reconstruction processing on the interference signal output from the differential detector 129. First, the reconstructing unit 1901 performs fixed pattern noise elimination on the interference signal. The fixed pattern noise elimination is performed by, for example, extracting fixed pattern noise by averaging a plurality of detected A-scan signals, and subtracting this from the input interference signal. Next, the reconstructing unit 1901 performs desired window function processing in order to optimize the depth resolution and the dynamic range, which will be in a trade-off relationship when Fourier transform is performed in a finite interval. Next, the reconstructing unit 1901 generates a tomographic image by performing FFT processing. Note that, as described above, the reconstruction processing is not limited to this, and may be performed with known arbitrary methods.

<Step S404>

In step S404, generation of three-dimensional data is performed. Hereinafter, referring to the flowchart of FIG. 4B and FIG. 6A to FIG. 11B, the generation of a three-dimensional data will be described in detail. When the generation processing of three-dimensional data is started, the processing proceeds to step S441.

<Step S441>

In step S441, in order to perform alignment of tomographic images, the detecting unit 1905 detects retinal boundary lines. As the layers for performing alignment, for example, the boundary L1 between the ILM and the NFL, and the photoreceptor inner segment-outer segment junction L3 illustrated in FIG. 3B are detected. The detecting unit 1905 applies each of a median filter and a Sobel filter to a tomographic image to be processed to create images (hereinafter, a median image and a Sobel image). Next, a profile is created for each A-scan from the created median image and Sobel image. It will be the profile of intensity value for a median image, and the profile of gradient for a Sobel image. Then, the peak in the profile created from the Sobel image is detected. The boundary line of each region of the retinal layer is detected by referring to the profiles of median images corresponding to before/after the detected peak and between the peaks. Note that the detection method of boundary lines is not limited to this, and known arbitrary methods may be used. For example, the detecting unit 1905 may detect a boundary line from a tomographic image by using a learned model for a machine learning model. In this case, as training data for the learned model, for example, a tomographic image may be used as input data, and a label image obtained by applying the label of a boundary line to the tomographic image by a doctor, etc., may be used as output data.

<Step S442>

In step S442, the aligning unit 1902 performs alignment of adjacent tomographic images. While imaging high-density radial scan, an eye is moving. As for movement within an XY surface, since imaging is performed while performing tracking in real time, alignment is almost made at the time of imaging. However, as for the depth direction, since real-time tracking is not performed, it is necessary to perform alignment between the data of tomographic images. Therefore, here, the alignment between the data of tomographic images obtained by radial scan will be described by using FIG. 6A to FIG. 6C.

Figure 6A:
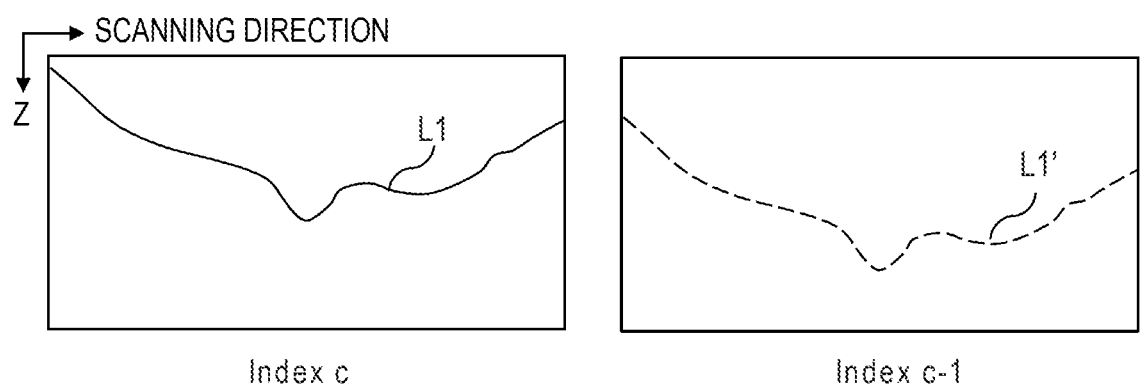
FIG. 6A is a diagram for describing an example of alignment according to Example 1.

FIG. 6A illustrates an example of a boundary line used for alignment. In the present example, a case will be described where the line of the boundary L1 (hereinafter simply referred to as a boundary line L1) between the inner limiting membrane (ILM) and the nerve fiber layer (NFL) is used for alignment. Note that, in the present example, although the example will be described that uses the boundary line L1 as the boundary line used for alignment, the kind of the boundary line is not limited to this. Other boundary lines may be used, and a plurality of boundary lines may be combined.

In FIG. 6A, reference data is Index c, and target data is Index c-1. Note that, in the present example, the data (image) of the boundary line L1 for a tomographic image for a first scan of radial scan is used as first reference data. Additionally, the data (image) of the boundary line L1 for a tomographic image adjacent to the reference data in a circumferential direction (a tomographic image corresponding to a scanning line adjacent to the scanning line of the reference data) is used as the target data. However, the first reference data is not be limited to the data of the tomographic image of the first scanning, and may be set arbitrarily.

Figure 6B:
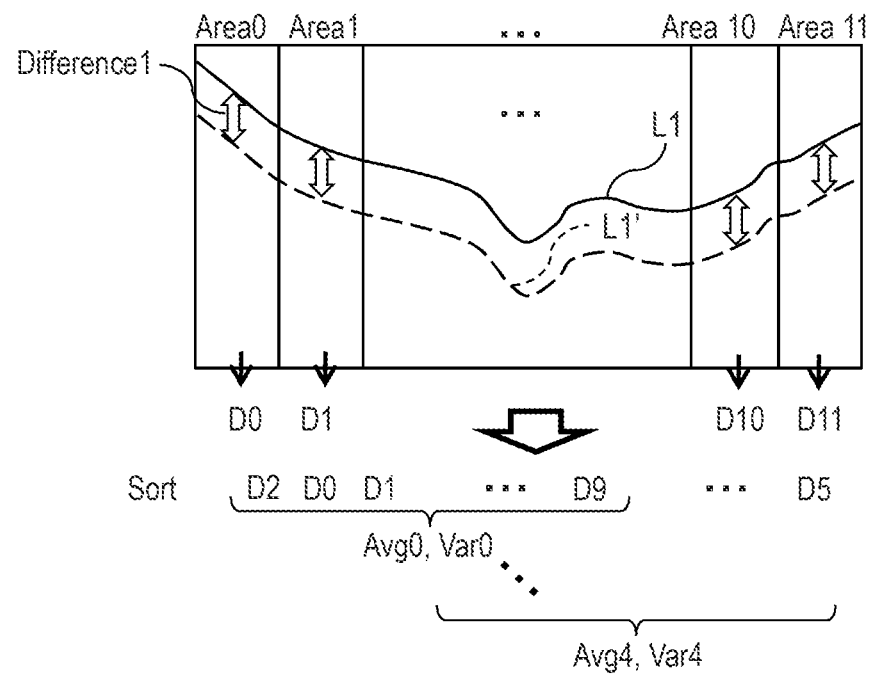
FIG. 6B is a diagram for describing an example of alignment according to Example 1.

FIG. 6B is a diagram for describing the alignment processing. FIG. 6B illustrates the boundary line L1 of the reference data, and a boundary line L1' of the data to be aligned at the same time. First, the aligning unit 1902 divides the reference data and the target data into a predetermined number of regions. In the present example, each of the reference data and the target data for the boundary line L1 is divided into 12 parts in a longitudinal direction. Here, let the divided regions be regions Area0 to Area11, respectively. Note that, although the divided regions are not drawn in the center portion of the image for simplification in FIG. 6B, the entire image is divided into the regions in practice.

Note that the number of region divisions is not limited to 12, and may be set arbitrarily. Additionally, the number of region divisions may be changed according to the image size in a transverse direction, or may be changed according to the size of the width of a boundary line detected in common. In the present example, although the sizes of boundary lines in the transverse direction in the reference data and the target data are the same for simplicity, in practice, a retinal layer may be shifted upward of a tomographic image (the direction of 0 in the z axis), and a partial region of the retinal layer may be lost from the image. In that case, a boundary line cannot be detected from the entire image. Therefore, in the alignment of boundary lines, the range in which a boundary line has been detected may be divided and aligned for the boundary line L1 of the reference data and the boundary line L1' to be aligned.

Next, the aligning unit 1902 obtains the difference in the positions in the depth direction (the Z direction) between the boundary line L1 and the boundary line L1' for each of the regions Area0 to Area11. An arrow Difference1 in the up-and-down direction in FIG. 6B represents the difference in the depth direction between the boundary line L1 and the boundary line L1'. The aligning unit 1902 obtains the difference in the positions in the depth direction between the boundary line L1 and the boundary line L1' for each data corresponding to an A-scan image in each region, averages the differences in the respective regions, and uses them as representative values D0 to D11 of the differences in the respective regions.

Next, the aligning unit 1902 sorts the representative values D0 to D11 obtained in the respective regions in decreasing order. The aligning unit 1902 selects eight values from the sorted representative values in decreasing order, and calculates an average and a variance value by using the eight selected representative values. Note that, although the number of selections is eight in the present example, the number of selections is not limited to this. The number of selections may be smaller than the number of divisions.

Here, the aligning unit 1902 repeatedly performs the calculation of the average value and the variance value for the sorted representative values by shifting the combinations to be selected one by one toward the larger representative values. In other words, when the aligning unit 1902 calculates the average value and the variance value for the smallest value to the eighth smallest value of the sorted representative values, next, the aligning unit 1902 calculates the average value and the variance value for the second smallest value to the ninth smallest value. The aligning unit 1902 performs this processing until the calculation of the average value and the variance value for the fifth smallest value to the twelfth smallest value. In the present example, since the calculation is performed by using the eight representative values of the 12 divided regions, a total of five kinds of average values and variance values are obtained.

Figure 6C:
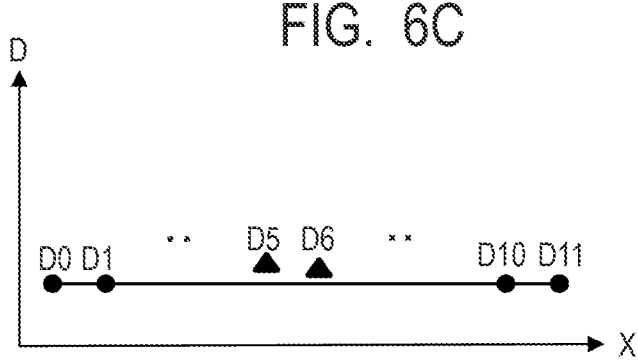
FIG. 6C is a diagram for describing an example of alignment according to Example 1.

The aligning unit 1902 obtains a shift value in the depth direction by using the eight representative values of difference at the time when the smallest variance value is calculated among the five kinds of obtained variance values. This will be described by using FIG. 6C and Math. 1. FIG. 6C is a graph in which a horizontal axis represents the center position (coordinate) of a divided region in the scanning direction, and a vertical axis represents the representative value of difference. In FIG. 6C, black dots are examples of the representative values for the combinations with which the variance value becomes the smallest, and black triangles represent examples of the representative values that are not selected as the combinations with which the variance value becomes the smallest.

Based on the equation indicated in Math. 1, the aligning unit 1902 calculates the shift value in the depth direction of each A-scan between the boundary line L1 of the reference data and the boundary line L1' of the target data by using the representative values (the black dots in FIG. 6C) for the combinations with which the variance value becomes the smallest.

$$D = ax + b \qquad \text{[Math. 1]}$$

Here, in the equation indicated in Math. 1, D is the shift value in the depth direction, and x is the position (coordinate) in the scanning direction, i.e., the A-scan position.

Additionally, a and b in Math. 1 are indicated in the following Math. 2 and Math. 3.

$$a = \frac{n \sum_{i=1}^{n} x_i D_i - \sum_{i=1}^{n} x_i \sum_{i=1}^{n} D_i}{n \sum_{i=1}^{n} x_i^2 - \left( \sum_{i=1}^{n} x_i \right)^2} \qquad \text{[Math. 2]}$$

$$b = \frac{\sum_{i=1}^{n} x_i^2 \sum_{i=1}^{n} D_i - \sum_{i=1}^{n} x_i D_i \sum_{i=1}^{n} x_i}{n \sum_{i=1}^{n} x_i^2 - \left( \sum_{i=1}^{n} x_i \right)^2} \qquad \text{[Math. 3]}$$

In Math. 2 and Math. 3, i is the number that specifies the selected representative value, xi is the center position (coordinate) of the divided region corresponding to the selected representative value in the scanning direction, and Di is the selected representative value. Note that n is the number of the selected representative values, and n is 8 in the present example.

Using the calculated shift value, the aligning unit 1902 shifts the tomographic image corresponding to the target data, and performs alignment of the tomographic image corresponding to reference data and the tomographic image adjacent to this. By dividing the region at the time of alignment, and using the values with which the variation becomes the smallest in the combinations of the difference values of the divided regions as in the present example, even when there is an error in the detection of boundary lines, the value of the region including the error in the detection of boundary lines is not used for the calculation of the shift value. Therefore, the shift value in the depth direction can be stably calculated. Note that, although the average value is used as the representative value in the depth direction of each region, the median may be used, and an arbitrary kind of representative value may be used. Further, although the variance value is calculated as the value indicating the variation, a standard deviation may be calculated, and the value may be an index with which the variation in values can be evaluated.

Regarding this processing, the aligning unit 1902 performs alignment on the data of all the adjacent tomographic images, while changing the reference data and the target data. In the present example, let the first reference data be the data of a boundary line detected from the first imaged data (for example, the data corresponding to the scanning line 1 in FIG. 5A). Additionally, let the target data be the data of a boundary line detected from the adjacent data (the data corresponding to the scanning line 2 in FIG. 5A) in the circumferential direction of the reference data. Then, when the alignment of the tomographic images corresponding to these reference data and target data is completed, next, using the data (the data corresponding to the scanning line 2 in FIG. 5A) previously used as the target data as the reference data, alignment is performed by using the data further next to it (the data corresponding to the scanning line 3 in FIG. 5A) as the target data. This processing is performed on the data of all tomographic images for one round of radial scan.

Note that, in the radial scan illustrated in FIG. 5A, when alignment is performed on the boundary line data (the data corresponding to the scanning lines 1 and 12 in FIG. 5A) in which the first scan and the last scan are adjacent to each other, the scanning directions at the time of imaging are opposite. Therefore, when performing alignment on these two-dimensional tomographic images, the alignment can be performed by reversing the left and right of the images.

Additionally, as a result of performing alignment on a plurality of tomographic images for one round, misalignment may occur between the tomographic images corresponding to the first scan and the last scan. In this case, overall modification can be performed by returning the amount of misalignment (shift value) that occurs between the data corresponding to the first scan and the last scan in the opposite direction. For example, when the amount of misalignment that occurs between the data corresponding to the first scan and the last scan is +5 pixels, and the number of sheets of radial scan is 100, the amount of misalignment is modified by +0.05 pixels for each sheet. For example, the modification amount is calculated for each scanning line, such as the amount of misalignment of a scanning line 100 is +5 pixels, the amount of misalignment of a scanning line 99 is +4.95 pixels, and the amount of misalignment of a scanning line 98 is +4.9 pixels. Then, the amount of misalignment and the modification amount obtained between adjacent tomographic images are integrated to obtain the amount of misalignment of each of the tomographic images. Based on the amount of misalignment calculated for each of the tomographic images in this manner, the aligning unit 1902 can also shift each of the tomographic images, and perform alignment of the tomographic images.

Although an example of the method of performing alignment in the depth direction is illustrated in the present example, the method is not limited to this method. For example, in the case of radial scan, all tomographic images cross in the vicinity of the center of the tomographic images. Therefore, the alignment in the depth direction may be performed by using A-scan data of the centers of the tomographic images (or including a plurality of pieces of A-scan data in the vicinity of the centers). In this case, the positions may be aligned based on the position of the first imaged tomographic image, or alignment may be performed based on a tomographic image in which the position of the retina is the lowest, but that includes the retina within the image, among a plurality of tomographic images. Further, the location may be detected at which the positions of boundary lines are most aligned when moved in the transverse direction as well as the depth direction by using the data of boundary lines as described above, or alignment in the transverse direction and the depth direction within a tomographic image surface may be performed by using the image features of the tomographic image. In the alignment using the image features, for example, a ROI (area of interest) may be set to images, and alignment according to the similarity in ROIs between adjacent tomographic images may be performed. On this occasion, a region that is smaller than the entire image, but includes a retinal layer is set as the ROI. Alternatively, feature points may be detected from images, and alignment of the feature points may be performed. Further, a one-dimensional image may be generated by projecting a two-dimensional tomographic image in the depth direction, and alignment according to the image features of the one-dimensional image and an SLO image may be performed. Note that these alignment methods are examples, and alignment of tomographic images may be performed with known arbitrary methods.

<Step S443>

In step S443, the data integrating unit 1903 arranges, in a three-dimensional spaces, tomographic images obtained by performing radial scan and alignment, and performs integration of the data on a plurality of tomographic images. The processing will be described by referring to FIG. 7A to FIG. 7C.

Figure 7A:
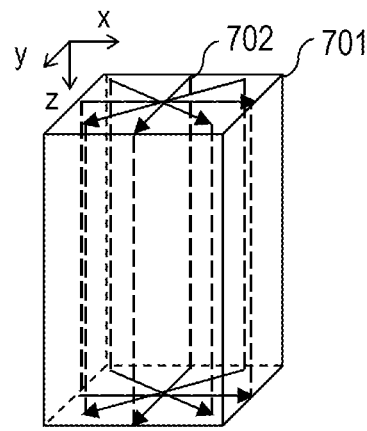
FIG. 7A is a diagram for describing an example of handling of data in the scanning state according to Example 1.

FIG. 7A illustrates an example in which a plurality of radially scanned tomographic images 702 are arranged in a three-dimensional space 701. Since the plurality of tomographic images 702 are aligned in step S442, the data integrating unit 1903 arranges the aligned tomographic image corresponding to each scanning line in the three-dimensional space. Note that the data integrating unit 1903 may arrange, in the three-dimensional space, the tomographic images before the alignment corresponding to the respective scanning lines, so as to perform misalignment modification of tomographic images based on the alignment parameters calculated in step S442.

When performing radial scan, in the center position of scanning, A-scans become dense since scanning lines become dense, and in the periphery, A-scans become sparse since scanning lines become sparse. When A-scans become dense, the tomographic images corresponding to scanning lines will cross each other, and A-scan data will be obtained in an overlapping manner at the position where the tomographic images cross each other. Therefore, the data integrating unit 1903 performs the integration processing of the overlapping A-scan data in the vicinity of the center of scan where the A-scans become dense. The processing will be described by referring to FIG. 7B and FIG. 7C.

Figure 7B:
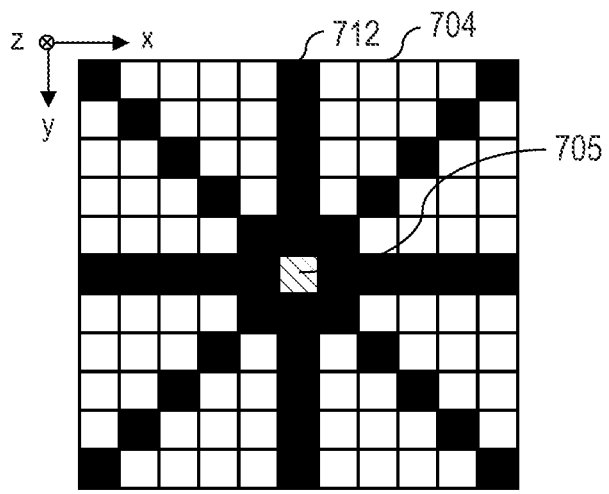
FIG. 7B is a diagram for describing an example of handling of data in the scanning state according to Example 1.
Figure 7C:
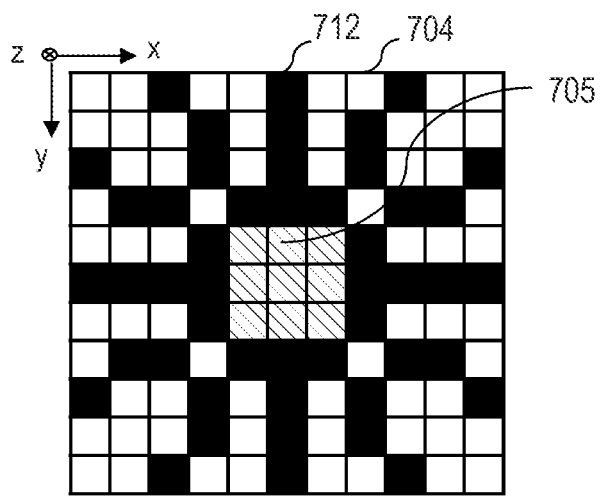
FIG. 7C is a diagram for describing an example of handling of data in the scanning state according to Example 1.

FIG. 7B and FIG. 7C are examples in which the center region of the XY surface is partially enlarged in radial scan, and FIG. 7B illustrates a case of 4 scans, and FIG. 7C illustrates a case of 6 scans. In FIG. 7B and FIG. 7C, black squares 712 indicate scanned positions, white squares 704 indicate unscanned positions, and shaded squares 705 indicate positions that has been scanned multiple times. As illustrated in FIG. 7C, when the number of times of scanning (the number of scanning lines) is increased, the region in which A-scan is performed multiple times is increased. In other words, when the number of times of scanning is increased in order to build the three-dimensional data corresponding to a more correct shape of an eye to be examined, the scanning density will be increased, and the scan data will be overlapped in the center portion.

Therefore, the data integrating unit 1903 can define a representative value by performing the integration processing of the A-scan data in the region of the squares 705 in the shaded region illustrated in FIG. 7B and FIG. 7C, and can use the representative value as the A-scan data of the region of the squares 705 in the corresponding shaded region. For example, the data integrating unit 1903 can integrate a plurality of pieces of A-scan data in the region of the squares 705 in the shaded region, and can use it as the representative value of the region. For the integration method, a method may be used that integrates data with statistical calculation that calculates the average value, the weighted average value, the median, the maximum value, or the minimum value, etc., by using all the A-scan data obtained in a corresponding region. Alternatively, a correlation value may be calculated for each obtained A-scan data, and data may be integrated with statistical calculation that calculates the average value, the weighted average value, the median, the maximum value, or the minimum value, etc., by using only the A-scan data with high correlation values.

Additionally, as the integration processing of data, the data integrating unit 1903 may select one piece of A-scan data from a plurality of pieces of A-scan data to define a representative value. As the selection method, A-scan data may be selected according to the obtained timing, such as A-scan data obtained first, A-scan data obtained in the middle, or A-scan data obtained last. Alternatively, a correlation value may be calculated for each obtained A-scan data, and A-scan data may be selected according to the result of performing the calculation, such as A-scan data with the highest average value of the correlation values, and A-scan data with the lowest variation in the correlation values.

Note that the data integrating unit 1903 may define the A-scan position for performing data integration, according to the number of scanning lines, the angle spacing, and the imaging range included in the imaging parameters, and the number of A-scans included in 1 B-scan, etc. For example, a table can be prepared that associates A-scan positions for performing integration of data with the above-described imaging parameters, and the data integrating unit 1903 can define the A-scan position by referring to the table. Note that the controlling apparatus 200 may store the number identifying each scanning line in association with the tomographic image corresponding to the scanning line, and the data integrating unit 1903 may define the A-scan position for performing integration of data, based on the number and the imaging parameters.

<Step S444>

Figure 8A:
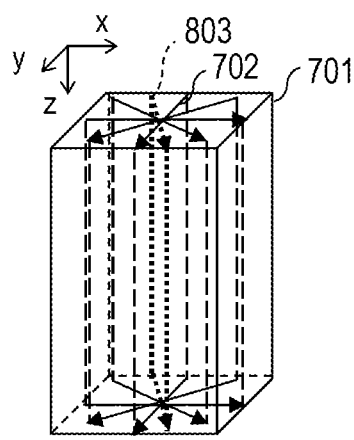
FIG. 8A is a diagram for describing an example of data generation in the scanning state according to Example 1.
Figure 8B:
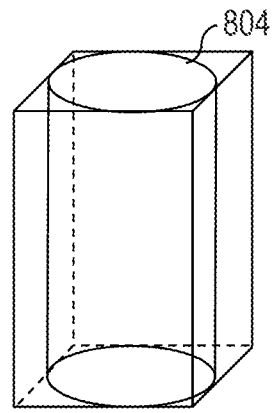
FIG. 8B is a diagram for describing an example of the data generation in the scanning state according to Example 1.
Figure 8C:
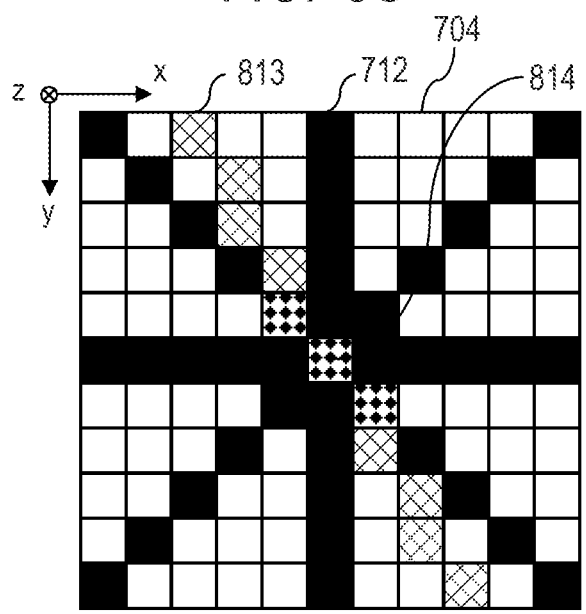
FIG. 8C is a diagram for describing an example of the data generation in the scanning state according to Example 1.

In step S444, the data generating unit 1904 builds three-dimensional data based on the data obtained by arranging/integrating, in the three-dimensional space by the data integrating unit 1903, the tomographic images obtained by radial scan. The processing will be described by referring to FIG. 8A to FIG. 8C. FIG. 8A is an example in which an estimated tomographic image 803 (estimated A-scan data) is generated for the remaining space that has not been scanned, after arranging the tomographic images obtained by actual radial scan illustrated in FIG. 7A. FIG. 8B illustrates three-dimensional data 804 generated from the tomographic images 702 obtained by scanning and the estimated tomographic image 803. FIG. 8C is an example in which the region of the center of the xy surface is partially enlarged in the radial scan in FIG. 8A, and rhombic pattern squares 813 indicate the positions of the estimated tomographic image 803 in FIG. 8A. Note that rhombic pattern squares 814 in FIG. 8C indicate the positions where the imaged A-scan data exists in the surface including the rhombic pattern squares 813.

Here, the processing will be described that generates the estimated tomographic image 803 with interpolation processing by the data generating unit 1904. With respect to the estimated tomographic image 803, the data generating unit 1904 estimates A-scan data with interpolation processing for the positions 813 where the A-scan data does not exist. When an image is estimated/generated with interpolation processing, the data generating unit 1904 performs, for example, interpolation of A-scan data along the circumferential direction.

Specifically, the data generating unit 1904 uses the distance and angle from the center to a location at which A-scan data is to be estimated to calculate a weighted average of tomographic images that are on both sides of the location and that are obtained by radial scan, and estimates A-scan data. Specifically, according to the distances from the center of the location at which the A-scan data is to be estimated to the tomographic images on the both sides in the circumferential direction, the data generating unit 1904 can generate the estimated A-scan data by calculating the weighted average of the tomographic images on the both sides. Here, as for the weighting on the tomographic images on the both sides, the weighting is performed such that the closer the distance from the location at which the A-scan data is to be estimated to the tomographic images in the circumferential direction, the greater the specific gravity of the data of the tomographic images. Additionally, as for the data in the tomographic image used for weighted averaging, for example, in the tomographic image, the A-scan data may be used that is at the position closest to the location at which the A-scan data is specified, or it may be the average value, the median, etc., of A-scan data at a plurality of positions close to the location. By repeatedly performing the interpolation processing, the data generating unit 1904 can build the three-dimensional data 804.

Figure 9A:
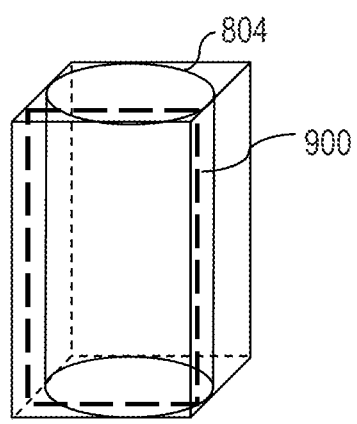
FIG. 9A is a diagram for describing an example of a tomographic image obtained by cutting an arbitrary cross section from three-dimensional data according to Example 1.
Figure 9B:
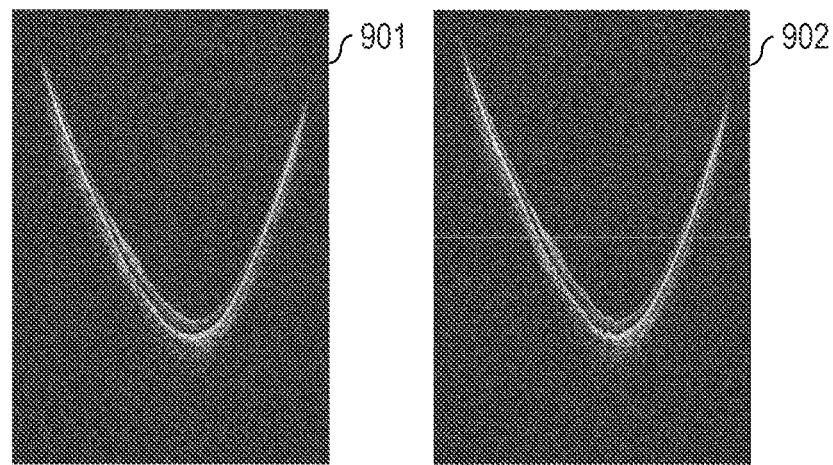
FIG. 9B is a diagram for describing an example of a tomographic image obtained by cutting an arbitrary cross section from the three-dimensional data according to Example 1.
Figure 9C:
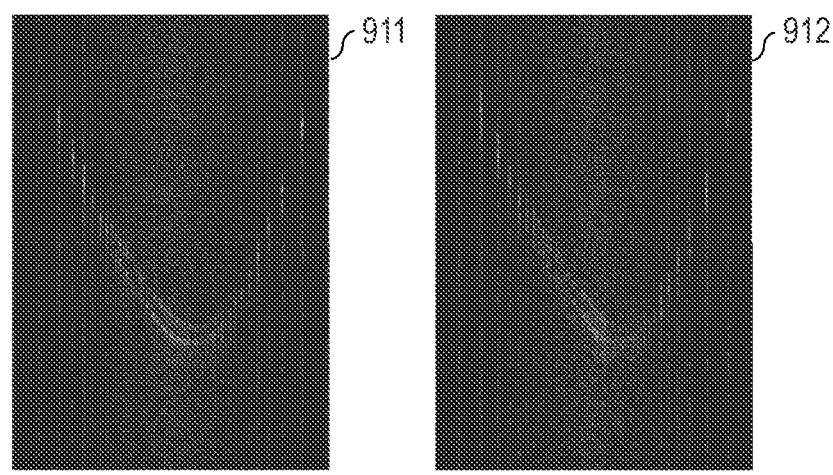
FIG. 9C is a diagram for describing an example of a tomographic image obtained by cutting an arbitrary cross section from the three-dimensional data according to Example 1.

FIG. 9A to FIG. 9C illustrate examples of tomographic images obtained by cutting arbitrary cross sections from three-dimensional data built from radially scanned tomographic images. FIG. 9A illustrates the three-dimensional data 804 generated by the three-dimensional data generation processing in step S404, and a cross section position 900 of the tomographic images illustrated in FIG. 9B and FIG. 9C.

FIG. 9B illustrates the tomographic image at the cross section position 900 of the three-dimensional data 804. In FIG. 9B, a tomographic image 901 is an example of the image generated from the three-dimensional data built by using the data for which the alignment processing has been performed in step S442. Additionally, a tomographic image 902 is an example of the image generated from the three-dimensional data built without performing the alignment processing in step S442. As illustrated in the tomographic image 902 in FIG. 9B, in a case where the three-dimensional data is built without performing the alignment processing, when the tomographic image of an arbitrary cross section is generated from the three-dimensional data, the structure of the retina is distorted. On the other hand, as illustrated in the tomographic image 901, when the tomographic image of an arbitrary cross section is generated from the three-dimensional data built by using the data for which the alignment processing has been performed, the distortion in the structure of the retina can be reduced.

Further, FIG. 9C illustrates examples of tomographic images generated from the three-dimensional data before the data generating unit 1904 performs the interpolation processing, and obtained by scanning radially 128 times. A tomographic image 911 corresponds to the tomographic image 901, and a tomographic image 912 corresponds to the tomographic image 902, respectively. As illustrated in FIG. 9C, it can be seen that, in radial scan, A-scan data is more densely obtained when the A-scan data is closer to the center portion, and the A-scan data becomes sparse when the A-scan data is in the periphery.

Additionally, the data generating unit 1904 can also perform the processing of estimating an estimated tomographic image generated by the interpolation processing to a natural (practical) tomographic image with a machine-learning model. In the present example, the data generating unit 1904 generates, by using a pre-trained learned model, a natural tomographic image from an estimated tomographic image generated by the interpolation processing. Here, referring to FIG. 10A and FIG. 10B, an example will be described in which the data generating unit 1904 according to the present example generates a natural tomographic image by using deep learning, which is one form of machine learning.

Figure 10A:
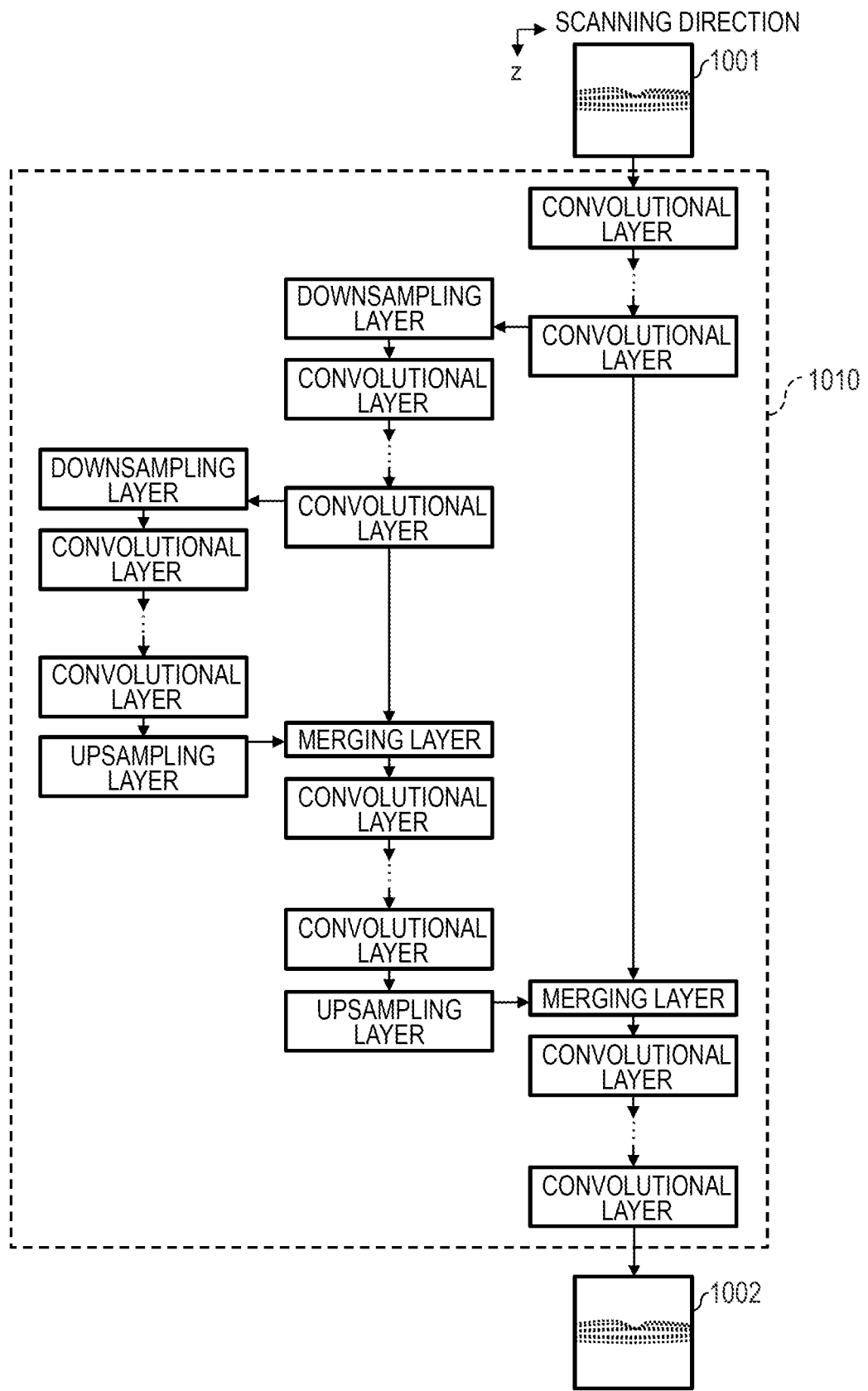
FIG. 10A is a diagram for describing a machine learning model according to Example 1.

FIG. 10A illustrates a U-net type convolutional neural network (CNN) as an example of the configuration of a deep learning model in the data generating unit 1904. A configuration 1010 illustrated in FIG. 10A is formed from a plurality of layer groups responsible for the processing that processes and outputs an input value group. Note that, as the kinds of the layers included in the configuration 1010, there are a convolution layer, a downsampling layer, an up sampling layer, and a merger layer as illustrated in FIG. 10A.

The convolutional layer is a layer that performs convolution processing on the input value group according to parameters, such as the kernel size of a set filter, the number of filters, the value of stride, and the value of dilation. Note that the number of dimensions of the kernel size of a filter may also be changed according to the number of dimensions of an image that is input.

The downsampling layer is a layer that performs processing of making the number of output value groups smaller than the number of input value groups by thinning out or combining the input value groups. There is, for example, Max Pooling processing as specific processing. The upsampling layer is a layer that performs processing of making the number of output value groups larger than the number of input value groups by duplicating the input value groups, or adding a value interpolated from the input value groups. There is, for example, linear interpolation processing as specific processing. The merger layer is a layer that performs processing of inputting, from a plurality of sources, a value group such as an output value group of a certain layer or a pixel value group forming an image, and merging them by connecting or adding them.

With such a configuration, value groups obtained by outputting the pixel value groups forming the input image 1001 through a convolution processing block, and the pixel value groups forming the input image 1001 are merged in the merger layer. Thereafter, the merged pixel value groups are shaped into an inference image 1002 in the last convolutional layer.

Note that cautions are required since, when the setting of parameters to layer groups and node groups forming a neural network are different, the degree to which the trend trained from training data can be reproduced in output data may be different. That is, since appropriate parameters are different according to the mode at the time of implementation in many cases, the appropriate parameters can be changed into preferable values when necessary.

Further, in addition to the method of changing the parameters as described above, there is a case where a CNN can achieve better characteristics by changing the configuration of the CNN. The better characteristics are, for example, high accuracy of processing, a short time of processing, or a short time required for training of a machine-learning model.

Note that the configuration 1010 of the CNN used in the present modification is a U-net type machine learning model that has the function of an encoder formed from a plurality of layers including a plurality of downsampling layers, and the function of a decoder formed from a plurality of layers including a plurality of upsampling layers. The U-net type machine learning model is configured (by using, for example, skip connection) such that the geometry information (spatial information) that is made ambiguous in the plurality of layers formed as the encoder can be used in a layer of the same dimension (mutually corresponding layer) in the plurality of layers formed as the decoder.

Note that, although not illustrated, as a variation example of the configuration of the CNN, for example, a batch normalization layer, and an activation layer using a rectifier linear unit may be incorporated after the convolutional layer.

Here, training data for the machine-learning model according to the present example will be described. In the present example, a tomographic image included in the three-dimensional data generated by the interpolation processing is used as input data, a tomographic image included in the three-dimensional data obtained by actually performing dense scanning is used as output data, and these are used as a pair of training data. The training data will be described by referring to FIG. 10B. Note that a learned model may be a pre-trained machine learning model, and learning processing may be performed in advance by using an OCT apparatus according to the example, or other apparatus, etc.

Figure 10B:
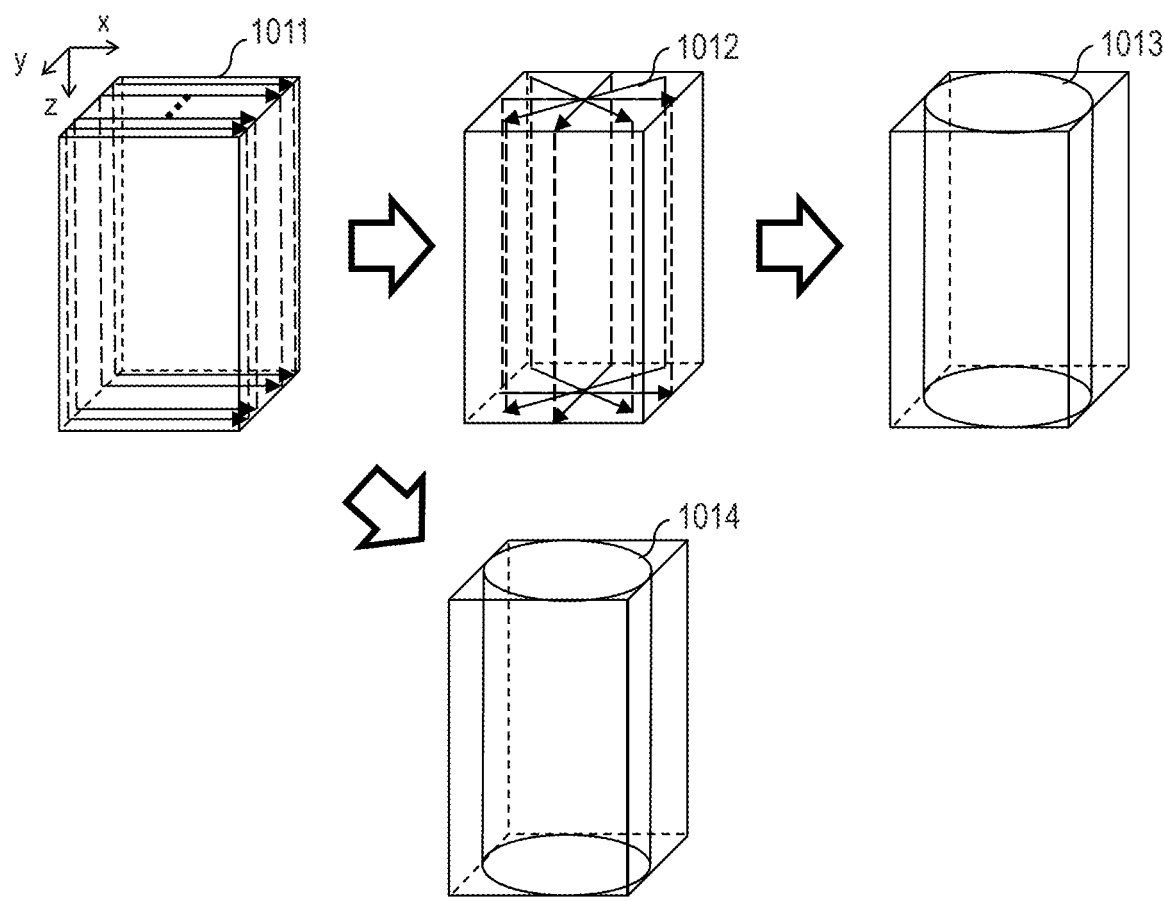
FIG. 10B is a diagram for describing training data according to Example 1.

In FIG. 10B, three-dimensional data 1011 indicates three-dimensional data imaged by raster scanning. When generating interpolation data from the three-dimensional data imaged by the raster scanning, adjacent tomographic images need to be aligned with each other. Note that, as for preparation (creation) of training data, for example, alignment of adjacent tomographic images imaged by the raster scanning may be performed by using the aligning unit 1902, or the alignment may be performed by other image processing apparatus.

Three-dimensional data 1012 indicates an example of the three-dimensional data in which the data of A-scan positions corresponding to radial scan is left, and the data that is not at the position of the radial scan is removed from the aligned three-dimensional data 1011. Therefore, when a tomographic image of an arbitrary cross section of the three-dimensional data 1012 is generated, the tomographic image will be the tomographic image 911 illustrated in FIG. 9C.

Three-dimensional data 1013 is an example of three-dimensional data generated by the interpolation processing from the three-dimensional data 1012. Additionally, three-dimensional data 1014 is obtained by extracting the data corresponding to the three-dimensional data 1013 from the three-dimensional data 1011. Here, since the three-dimensional data 1013 and the three-dimensional data 1014 are generated based on the three-dimensional data 1011, the alignment processing between the two data, i.e., the three-dimensional data 1013 and the three-dimensional data 1014, is not required. The machine learning model according to the present example learns the training data that uses, as input data, a tomographic image including interpolation data in the three-dimensional data 1013 generated in this manner, and uses, as output data, a corresponding tomographic image of the three-dimensional data 1014. Accordingly, the learned model can estimate/generate an actually imaged tomographic image from the tomographic images estimated by the interpolation processing.

Note that a tomographic image to be estimated by the interpolation processing is not limited to a tomographic image developed on the above-described radial scan. For example, 1000 A-scan tomographic images inferred with the interpolation processing after thinning out 1000 A-scan tomographic images to 500 A-scans, and the original 1000 A-scan tomographic images may be learned in pairs.

Further, the generation method of the three-dimensional data 1012, 1013, and 1014 is not limited to the above-described method. For example, the three-dimensional data 1012 may be created by extracting the three-dimensional data 1014 corresponding to the imaging range by the radial scan from the three-dimensional data 1011, and leaving the data at the A-scan positions corresponding to predetermined radial scan in the three-dimensional data 1014.

The data generating unit 1904 can build more natural three-dimensional data by replacing a tomographic image including interpolation data in the three-dimensional data estimated by the interpolation processing with a tomographic image generated from the tomographic image by using the learned model. Note that a learned model may be used that has been trained by using the three-dimensional data 1013 as the input data of training data, and the three-dimensional data 1014 as the output data. In this case, the data generating unit 1904 can build more natural (practical) three-dimensional data from the three-dimensional data estimated by the interpolation processing by using the learned model. When the construction of the three-dimensional data is completed by the data generating unit 1904, the processing proceeds to step S405.

<Step S405>

Figure 11A:
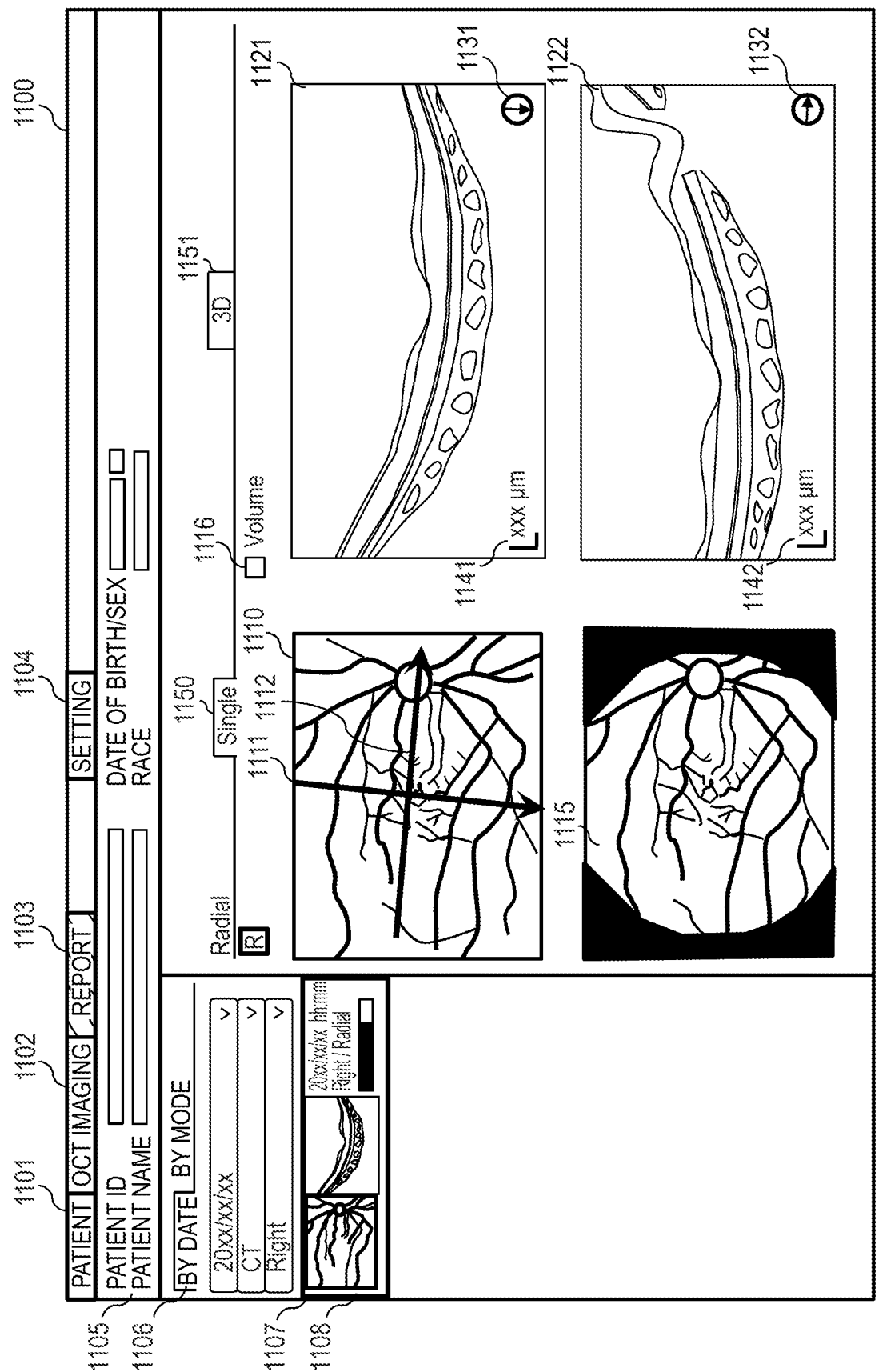
FIG. 11A illustrates an example of a user interface according to Example 1.

In step S405, the controlling unit 191 displays, on the display unit 192, the three-dimensional data generated from the tomographic images obtained by the radial scan. Examples of a display screen in the present example is illustrated in FIG. 11A and FIG. 11B. The description of a basic screen will be given by referring to FIG. 11A. FIG. 11A illustrates a display screen 1100, and the display screen 1100 is provided with a patient tab 1101, an imaging tab 1102, a report tab 1103, and a setting tab 1104. The oblique lines in the report tab 1103 represent an active state of a report screen. In the present example, an example will be described that displays the report screen for image confirmation after the imaging processing ends.

The report screen is provided with a patient information display portion 1105, an examination sorting tab 1106, an examination list 1107, and examination list 1108. The black frame of the examination list 1108 represents the selected examination, and the selected examination data is displayed on the screen. The thumbnails of a fundus image and a tomographic image are displayed in the examination list 1107 illustrated in FIG. 11A. Additionally, the report screen is provided with tabs 1150 and 1151 of view modes, a tomographic image is displayed in the report screen for the tab 1150, and three-dimensional data is displayed in the report screen for the tab 1151.

Here, the report screen for the tab 1150 will be described. A fundus image 1110 obtained by using the SLO optical system 140, a front image (En-Face image) 1115 generated by using the three-dimensional data generated from tomographic images obtained by the radial scan, a first tomographic image 1121, and a second tomographic image 1122 are displayed in the report screen. Note that the En-Face image will be described later.

Scanning positions 1111 and 1112 of the first and second tomographic images 1121 and 1122 are indicated on the fundus image 1110, and the scanning positions 1111 and 1112 indicate one cross section position scanned radially, and the cross section position orthogonally intersects with it.

Indexes 1131 and 1132 are indicated in the first and second tomographic images 1121 and 1122, and the indexes 1131 and 1132 indicate the orientations and positions of the tomographic images. Additionally, aspect ratios 1141 and 1142 are displayed in the first and second tomographic images 1121 and 1122, and these indicate the aspect ratios of the tomographic images. Specifically, the aspect ratios 1141 and 1142 indicate the lengths (for example, 200 μm), which serve as the references in the tomographic images illustrated in FIG. 11A, with the respective vertical and horizontal lines.

Further, it is assumed that, for the first tomographic image 1121 and the second tomographic image 1122, the controlling unit 191 can switch and display the images by using a user interface not illustrated. For example, when the operator rotates a mouse wheel of the input unit, the controlling unit 191 can change the scanning position 1111 of the tomographic image displayed on the fundus image 1110 clockwise or counterclockwise, and can continuously switch and display the tomographic image corresponding to the scanning position. In this case, the first and second tomographic images 1121 and 1122 may be switched together while maintaining the orthogonal positional relationship, or each of the images may be independently switched.

Next, referring to FIG. 11B, a case will be described where an arbitrary tomographic image is displayed from the three-dimensional data built based on the tomographic images obtained by the radial scan. FIG. 11B illustrates the display screen 1100 in a state where a check box 1116 is checked in order to display an arbitrary cross section from the three-dimensional data. The first tomographic image 1121 is an example of one cross section image scanned radially, and a third tomographic image 1123 is an example of the image corresponding to a cross section scanned horizontally from the built three-dimensional data.

A scanning position 1113 indicates the position of scanning corresponding to the third tomographic image 1123 on the fundus image 1110, and an index 1133 indicates the orientation and position of the third tomographic image 1123. An aspect ratio 1143 indicates the aspect ratio of the displayed tomographic image. Note that it is assumed that the third tomographic image 1123 can also be similarly switched and displayed by using the user interface not illustrated. For example, when the mouse wheel is rotated, the position (scanning position 1113) of the tomographic image displayed on the fundus image 1110 is moved up and down, and adjacent tomographic images can be continuously switched and displayed. In this case, each of the first and third tomographic images 1121 and 1123 may be independently switched.

Although not illustrated, an arbitrary cross section for the scanning position corresponding to the third tomographic image 1123 is not limited to a horizontal direction, and may be a vertical direction, or may be an oblique direction. Further, it may be an arbitrary straight line or an arbitrary curved surface specified by the operator. For example, the operator specifies arbitrary points on the fundus image 1110 with mouse operations or touch-panel operations. Since a point on the fundus image 1110 is a point of XY coordinates, the data generating unit 1904 collects a plurality of pieces of A-scan data located on a straight line or curved line connecting the specified points to generate one B-scan. The controlling unit 191 displays, on the display unit 192, a B-scan image generated by the data generating unit 1904 as the third tomographic image 1123. Note that the region for displaying the third tomographic image 1123 may be the region in which the first tomographic image 1121 is displayed.

According to the configuration described above, the OCT apparatus according to the present example can generate three-dimensional data from a plurality of tomographic images obtained by highly dense radial scan, and can display the images of arbitrary cross sections. Accordingly, the state of the entire retina can be easily grasped with the data for single-time imaging.

As described above, the OCT apparatus according to the present example includes the signal processing unit 190, the aligning unit 1902, and the data generating unit 1904. The signal processing unit 190 functions as an example of an obtaining unit that obtains a plurality of tomographic images obtained by radially scanning the measuring light on the eye to be examined, and corresponding to a plurality of locations of an eye to be examined, respectively. The aligning unit 1902 aligns the plurality of obtained tomographic images with each other at least in the depth direction of the tomographic images. The data generating unit 1904 generates three-dimensional data by using the plurality of aligned tomographic images. Note that, in the present example, a tomographic image is an intensity tomographic image, and the signal processing unit 190 may generate and obtain a tomographic image by the reconstructing unit 1901, or may obtain a tomographic image from an external apparatus, such as a server outside the controlling apparatus 200. Additionally, the signal processing unit 190 may obtain the interference signal from the external apparatus, and may generate and obtain a tomographic image from the obtained interference signal by the reconstructing unit 1901.

Additionally, the OCT apparatus further includes the data integrating unit 1903. The data integrating unit 1903 defines the pixel value of a position at which at least two tomographic images among a plurality of aligned tomographic images intersect in a three-dimensional space, by using the value obtained by integrating the pixel values of the position of the at least two tomographic images. Especially, the data integrating unit 1903 uses, as the value obtained by integrating the pixel values, the statistic value of the pixel values of the at least two tomographic images in the position at which the at least two tomographic images intersect, or one pixel value of the pixel values. The data generating unit 1904 generates three-dimensional data by using a plurality of tomographic images and the pixel value defined by the data integrating units 1903. Additionally, the data generating unit 1904 generates data between a plurality of locations corresponding to the plurality of tomographic images in the three-dimensional data by the interpolation processing using two of the plurality of aligned tomographic images.

The OCT apparatus according to the present example having such a configuration can reduce the misalignment between a plurality of pieces of data obtained by radial scan. Additionally, since the misalignment between adjacent tomographic images is reduced also when generating three-dimensional data by using a plurality of two-dimensional tomographic images, three-dimensional data with reduced misalignment between pieces of data can be generated. Accordingly, the state of the entire retina can be easily grasped with the data for single-time imaging. Additionally, by integrating and using the data obtained in an overlapping manner for the same location by radial scan, the obtained data can be efficiently utilized. Further, by interpolating data between a plurality of locations with the interpolation processing, the thickness and state of the entire retina, and the shape of the retina can be accurately grasped with single-time imaging.

Note that in the alignment processing in step S442 according to the present example, the processing is performed while changing the reference data and the target data. However, the alignment processing is not limited to this. For example, the data (tomographic image) corresponding to one scanning in radial scan may be selected as a template, and by using the template as the reference data, the position of other data may be aligned with the reference data. Additionally, for example, the data (tomographic image) corresponding to predetermined scanning, for example, four scanning per 90 degrees, in radial scan may be used as templates, and the data corresponding to scanning included in 45 degrees before and after the predetermined scanning may be aligned with the templates.

Additionally, although the alignment is performed for each A-scan in the present example, the alignment may be performed for each strip-shaped region in which predetermined A-scans are collected. In this case, the calculation of a shift value and the movement of the position of data may be performed for each region. Note that, as for the shift value calculated for each A-scan, a statistic value such as the average value of the region may be calculated, and the calculated statistic value may be used as the shift value of the region, or the shift value of predetermined A-scan included in the region may be used as the shift value of the entire region. Additionally, the calculation of the shift value may not be performed for all A-scans, and for example, the calculation of the shift value may be performed for only several discretely defined A-scans among the A-scans included in 1 B-scan, and an interpolated value of the shift value may be used for the other A-scans.

Further, the alignment may be performed for each tomographic image. In this case, the alignment may be performed by comparing only the data of a typical A-scan, such as the data of the A-scan at the center of each data (tomographic image). Additionally, a statistic value, such as the average value of the shift value calculated for each A-scan or a region in which predetermined A-scans are collected, may be calculated, and the calculated statistic value may be used as the shift amount for the entire data.

Additionally, the data to be compared when calculating the shift value is not limited to the entire data of an A-scan. For example, the data of an image of a predetermined region in the depth direction included in an A-scan may be compared. Note that the entire data of an A-scan data may be used for one of the reference data and the target data. Similarly, the data of a predetermined region in the depth direction of the data of a strip-like region in which a plurality of A-scans are collected may be compared.

Further, the alignment of radial scan may be collectively performed for a plurality of tomographic images. For example, the alignment may be collectively performed for the tomographic images for a predetermined number of times of scanning, or the alignment may be collectively performed for the tomographic images corresponding to scanning included in a predetermined angle. Note that the unit of tomographic images for which the alignment is collectively performed may be dynamically defined according to the number of the scanning lines included in radial scan, may be determined according to an instruction by the operator, or may be set in advance. Note that, in this case, the calculation of the shift value may also be performed for each unit of tomographic images. In this case, the shift value may be a statistic value, such as the average value of the shift value for each tomographic image included in the unit, or may be the shift value of a predetermined tomographic image included in the unit.

Further, in the present example, every time the shift value is calculated for 1 set of the reference data and the target data, the positions of the reference data and the target data are aligned, but the timing for aligning the positions of data is not limited to this. After calculating the shift amounts for all pieces of data included in radial scan, the positions of the pieces of data may be collectively aligned. In this case, the alignment may be performed by moving the data corresponding to each scanning line for the amount of shift value obtained by accumulating, up to the data, the shift values obtained by comparing the reference data with the target data.

Note that, in the present example, when calculating the shift value, the overall modification is performed by returning the shift value generated between the data corresponding to the first scanning and the data corresponding to the last scanning in the opposite direction. However, the processing may not be performed. Additionally, the processing may be performed not for each A-scan, but for each strip-shaped region in which a plurality of A-scans are collected, or may be performed for each tomographic image corresponding to each scanning line. Further, it may be performed for every plurality of tomographic images corresponding to a plurality of scanning lines.

Additionally, in the present example, the example has been described in which a natural (practical) tomographic image is generated for the tomographic image in the surface formed by the scanning direction of radial scan and the z axis by using the learned model. However, the image generated by using the learned model is not limited to this. For example, the data generating unit 1904 may generate a natural front image from a front image (En-Face image) in the xy surface by using the learned model. In this case, the data generating unit 1904 inputs, to the learned model, the En-Face image generated from the three-dimensional data generated by the interpolation processing, and generates a more natural En-Face image. As the training data in this case, the En-Face image generated from the three-dimensional data 1013 illustrated in FIG. 10B may be used as input data, and the En-Face image generated from the data in the corresponding depth range of the three-dimensional data 1014 may be used as the output data.

Here, an En-Face image is an image obtained by projecting the data in an arbitrary depth range of three-dimensional data onto a two-dimensional plane (xy plane). Here, the depth range for which an En-Face image is generated can be defined by two arbitrary layer boundaries included in a tomographic image of an eye to be examined. Additionally, the depth range may be defined by an offset instruction by the operator. Further, the depth range may be defined as a range including a predetermined number of pixels in a shallow direction or a deep direction based on a certain layer boundary. Additionally, an En-Face image may be one cross section image of the xy surface in three-dimensional data, etc. Note that, as a technique of projecting the data corresponding to a depth range onto a two-dimensional plane, for example, a technique can be used that uses a representative value of the data in the depth range as the pixel value on the two-dimensional plane. Here, the representative value can include a value such as the average value, the median, or the maximum value of the pixel values in the depth range. The data generating unit 1904 can generate an En-Face image, which is a front image, by projecting at least a part of the data of three-dimensional data onto the two-dimensional plane.

Note that, although it has been assumed in the present example that the data generating unit 1904 generates a more natural tomographic image and an En-Face image by using the learned model, the signal processing unit 190 may perform this processing, or a component for performing this processing may be provided. Additionally, the processing of generating a more natural image by using the learned model does not necessarily have to be performed, and the processing may be configured to be performed according to, for example, an instruction by the operator. Note that, since an En-Face image may have different features in the image in different depth ranges, a learned model may be prepared for each predetermined depth range.

Example 2

In Example 1, the example has been described in which the drive controlling unit 180 controls the X scanner 107 and the Y scanner 110 to perform radial scan. In the present example, an example will be described in which three-dimensional data is more accurately generated by performing circular scan in addition to radial scan.

Hereinafter, referring to FIG. 12A to FIG. 12C, an OCT apparatus according to the present example will be described by focusing on the differences from the OCT apparatus according to Example 1. Note that, since each component of the OCT apparatus according to the present example is the same as each component of the OCT apparatus according to Example 1, the description will be omitted by using the same reference numerals.

Figure 12A:
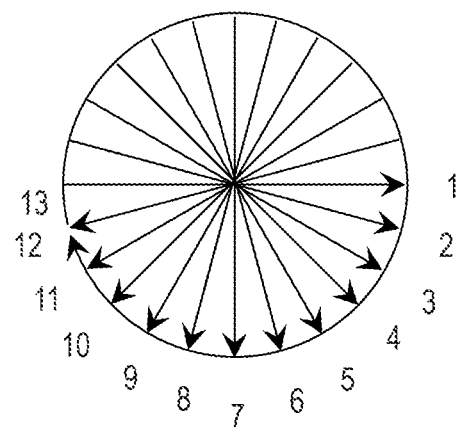
FIG. 12A is a diagram for describing an example of a scanning state according to Example 2.
Figure 12B:
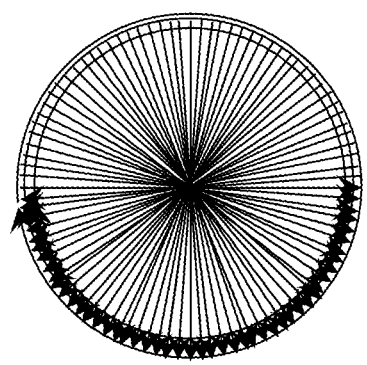
FIG. 12B is a diagram for describing an example of the scanning state according to Example 2.
Figure 12C:
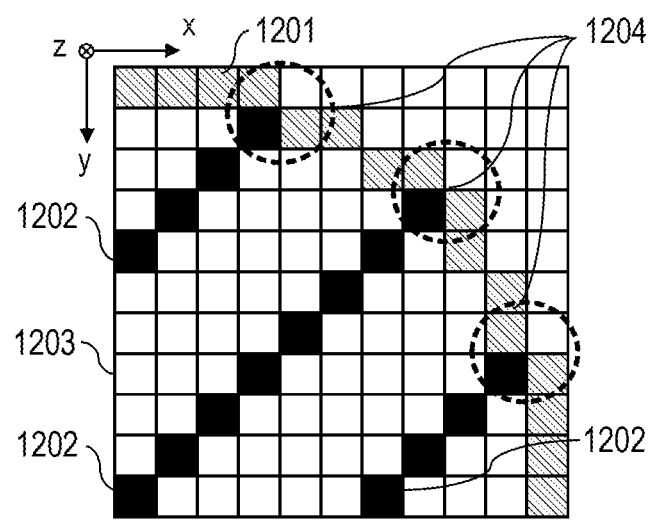
FIG. 12C is a diagram for describing an example of the scanning state according to Example 2.

FIG. 12A to FIG. 12C illustrate examples of scanning lines in which radial scan and circular scan are combined. In the figures, the arrows indicate the directions to be scanned. Note that the directions to be scanned may not be the directions illustrated in the figures, but may be the opposite directions. FIG. 12A illustrates 12 radial scan lines and one circular scan line for convenience of description.

Note that, when aiming at building three-dimensional data from radial scan, it is better to set scan lines densely as illustrated in FIG. 12B, and a number n of radial scan lines may be set to, for example, 90 or more. Further, when circular scan is used not only for alignment, but is also used for building three-dimensional-data, a number m of circular scan lines can also be set to, for example, 2 or more.

When combining radial scan and circular scan, circular scan may be performed after performing radial scan, or radial scan may be performed after performing circular scan. Alternatively, circular scan may be performed while performing radial scan, and the timing for performing a different scan pattern is not uniquely limited.

Comparing with the three-dimensional-data generation processing according to Example 1, the three-dimensional-data generation processing according to the present example is different in the alignment processing by the aligning unit 1902, and the integration processing of A-scan data by the data integrating unit 1903. Therefore, these kinds of processing will be described in the present example.

In the present example, in the alignment processing according to step S422, first, the data integrating unit 1903 arranges, in the three-dimensional space, the A-scan data obtained by circular scan and the A-scan data obtained by radial scan. Thereafter, the aligning unit 1902 performs alignment of the radial scan based on the circular scan. The alignment processing will be described by referring to FIG. 12C. FIG. 12C illustrates an enlarged example of a partial region of the XY surface in the circular scan and the radial scan. In FIG. 12C, shaded squares 1201 indicate the positions of the circular scan, black squares 1202 indicate the positions of the radial scan, white squares 1203 indicate unscanned positions, and dotted circles 1204 indicate the locations where the circular scan and the radial scan contact with each other.

The aligning unit 1902 performs alignment of A-scan data based on the location (circle 1204) where the circular scan and the radial scan contact with each other. The alignment parameter obtained in the location can be used as the alignment parameter (shift value) for an entire tomographic image. Since a continuous surface is imaged in a short time in the circular scan, almost no misalignment is seen in one image. Therefore, in the present example, the aligning unit 1902 performs alignment for a plurality of times of radial scan, based on the data of the circular scan. The alignment by the aligning unit 1902 according to the present example may be performed based on boundary line data detected by the detecting unit 1905, or may be performed based on an image feature amount. As indicated by the circles 1204, when there are a plurality of locations (A-scan positions) where the circular scan and the radial scan contact with each other, the alignment may be performed with data obtained by averaging the data of the plurality of locations, or the alignment may be performed by using any one piece of the data. Specifically, in the example in FIG. 12C, the data obtained by averaging the data of two pixel positions (A-scan positions) of the shaded squares 1201 contacting the edges of the black square 1202, and the data of the edges of the black square 1202 may be aligned.

Additionally, the radial scan corresponding to one scanning line contacts the circular scan at both ends. When performing alignment of the radial scan by using alignment results of both edges, the aligning unit 1902 may use the average value of the alignment parameters of both ends, or may use a result with a higher similarity of A-scan data of the contacting portions. Alternatively, when there is a difference between the alignment parameters of both ends, the aligning unit 1902 may perform alignment of an image obtained by the radial scan by smoothly modifying the image such that the parameters (the positions in the depth direction) of both ends match. For example, an image can be modified by accumulatively (gradually) moving each A-scan data from one end of the image in the depth direction for the value obtained by dividing the difference between the alignment parameters of both ends by the number of A-scans included in one scanning.

Although the example of performing the alignment of the radial scan based on the circular scan has been described in the present example, the alignment is not limited to this. For example, similar to Example 1, after performing the alignment of the radial scan first, the alignment of the radial scan may be performed with respect to the circular scan.

Next, the arrangement/integration processing of data according to step S443 by the data integrating unit 1903 will be described. The data integrating unit 1903 performs the integration processing of overlapping A-scan data in the vicinity of the center where A-scan becomes dense, and in the periphery locations where the circular scan and the radial scan overlap with each other, and arranges an aligned tomographic image corresponding to each scanning line in the three-dimensional space. Note that the data integrating unit 1903 may arrange a tomographic image before the alignment corresponding to each scanning line in the three-dimensional space, so as to perform the misalignment modification of the tomographic image based on the alignment parameter calculated in step S442. Here, as for the vicinity of the center, since the processing is the same as that according to Example 1, the description will be omitted.

As the integration processing of the data in the periphery locations where the circular scan and the radial scan overlap with each other, the data integrating unit 1903 selects, for example, the A-scan data obtained by the circular scan, and uses the A-scan data as the representative value of the locations for which the integration processing of data is to be performed. This is because, as described above, almost no misalignment is seen in one image, since a continuous surface is imaged in a short time in the circular scan. Additionally, since the alignment processing is completed by the aligning unit 1902, as the integration processing of the data in the periphery locations where the circular scan and the radial scan overlap with each other, the data integrating unit 1903 may define the representative value by integrating the A-scan data of the circular scan and the A-scan data of the radial scan. As the integration method, the data integrating unit 1903 may perform data integration with a statistical calculation that calculates the average value, the weighted average value, the median, the maximum value, or the minimum value by using the overlapping A-scan data. Additionally, the data integrating unit 1903 may calculate a correlation value for each overlapping A-scan data, and may perform data integration with a statistical calculation that calculates the average value, the weighted average value, the median, the maximum value, or the minimum value by using only the A-scan data with high correlation values.

Here, the alignment and data integration using the data corresponding to the radial scan including a plurality of scanning lines, and the data corresponding to one circular scan has been described. However, the alignment method for the scanning combining the radial scan and the circular scan is not limited to this. As illustrated in FIG. 12B, a plurality of times of radial scan and a plurality of times of circular scan may be combined. When performing a plurality of times of circular scan, the diameter size of each circle can be changed in the region overlapping with the range of the radial scan.

Next, an example will be described in which the data generating unit 1904 according to the present example generates an estimated tomographic image (estimated A-scan data) by the interpolation processing. Although the example of generating an estimated tomographic image by using only the radial scan has been described in Example 1, here, an example will be described in which the radial scan and the circular scan are used. Particularly, an example will be described in which the data generating unit 1904 estimates A-scan data with interpolation for a position (white square 1203) where the A-scan data does not exist and that is inside the circular scan (shaded squares 1201).

When generating an estimated tomographic image for the position by the interpolation processing, the data generating unit 1904 performs interpolation of data along, for example, the circumferential direction and the normal direction. More specifically, the data generating unit 1904 estimates A-scan data by using the distance and angle from the center of the location for which the A-scan data is to be estimated to calculate the weighted average of the tomographic images of the radial scan of both sides (in the circumferential direction) of the location, and the tomographic image of the circular scan in the normal direction orthogonal to the circumferential direction. Specifically, the data generating unit 1904 can generate estimated A-scan data by calculating a weighted average according to the distance from the location for which the A-scan data is to be estimated to the specified tomographic images on both sides in the circumferential direction, and the distance to the specified tomographic image of the circular scan in the normal direction. Here, as for the weighting, the weighting is performed such that the closer the distance from the location for which the A-scan data is to be estimated, the greater the specific gravity of the data of the tomographic image. Additionally, as the data in a tomographic image used for the weighted averaging, for example, in the tomographic image, the A-scan data of a position closest to the location for which the A-scan data is specified may be used, or it may be the average value, the median, etc., of the A-scan data of a plurality of positions close to the location. By repeatedly performing these kinds of interpolation processing, the data generating unit 1904 can build three-dimensional data. Note that, since the sub sequent processing is the same as that in Example 1, the description will be omitted.

As described above, the signal processing unit 190 according to the present example further obtains the tomographic image corresponding to at least one location of the eye to be examined, which is obtained by scanning the measuring light in a circle on the eye to be examined. Additionally, the aligning unit 1902 performs alignment of a plurality of tomographic images obtained by scanning the measuring light in a radial manner, based on the tomographic image obtained by scanning the measuring light in a circle.

According to the configuration described above, the OCT apparatus according to the present example performs the alignment for a plurality of tomographic images obtained by the scanning in a radial manner, based on the tomographic image obtained by the scanning in a circle that images a continuous surface in a short time. Therefore, the plurality of tomographic images obtained by the radial scan can be accurately aligned. Therefore, more correct three-dimensional data can be generated by generating the three-dimensional data from the aligned tomographic images. Accordingly, the thickness and state of the entire retina, and the shape of the retina can be more accurately obtained with single-time imaging.

Example 3

In Examples 1 and 2, the example has been described in which the drive controlling unit 180 controls the X scanner 107 and the Y scanner 110 to perform the radial and circular scan to obtain the tomographic images. In the present example, in addition to obtaining the tomographic images by these kinds of scanning, a motion contrast image is generated. Hereinafter, referring to FIG. 13 to FIG. 14B, the OCT apparatus according to the present example will be described by focusing on the differences from the OCT apparatus according to Example 1. Since each component of the OCT apparatus according to the present example is the same as each component of the OCT apparatus according to Example 1, except that a motion contrast image generating unit 1906 is further provided in the signal processing unit 190, the description will be omitted by using the same reference numerals.

Figure 13:
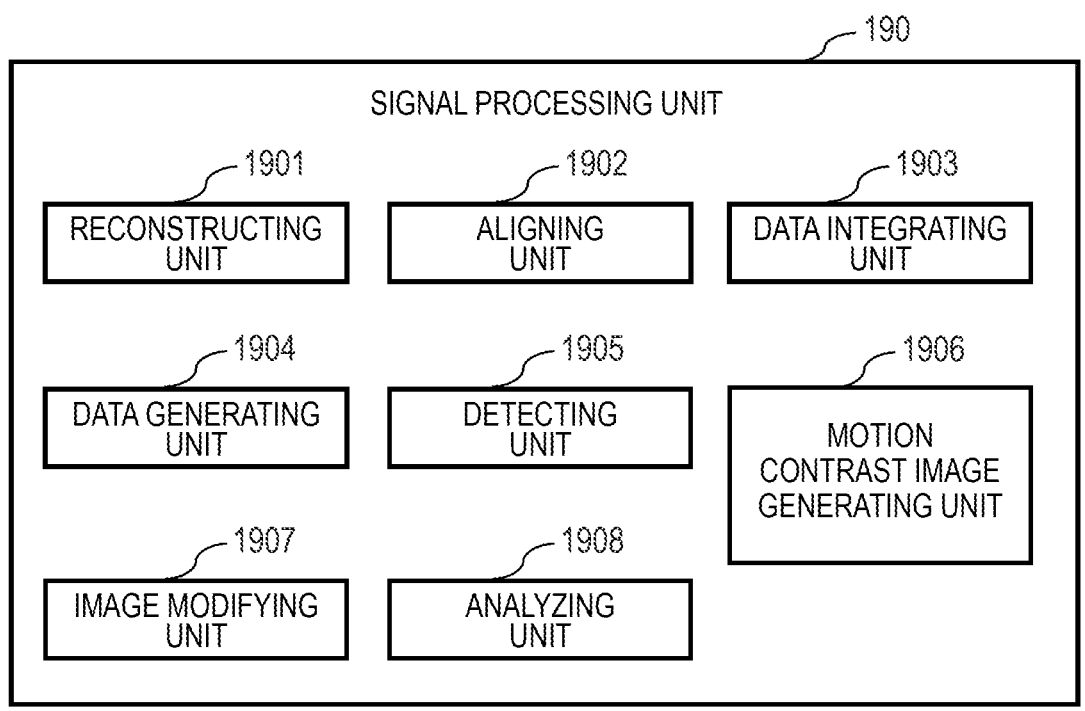
FIG. 13 illustrates an example of a schematic configuration of a signal processing unit according to Examples 3 to 5.

FIG. 13 illustrates a schematic configuration example of the configuration of the signal processing unit 190 according to Examples 3 to 5. The signal processing unit 190 according to the present example is provided with the motion contrast image generating unit 1906, in addition to the reconstructing unit 1901, the aligning unit 1902, the data integrating unit 1903, the data generating unit 1904, and the detecting unit 1905. Note that, although an image modifying unit 1907 and an analyzing unit 1908 are additionally illustrated in FIG. 13, these will be described in Examples 4 and 5.

The motion contrast image generating unit 1906 generates motion contrast data based on a generated tomographic image, and generates a motion contrast image corresponding to the tomographic image. As described above, a motion contrast image is data obtained by repeatedly imaging the same cross section of a measuring object with the OCT, and detecting the changes in the measuring object over time during the imaging. A motion contrast image can be obtained by, for example, calculating the changes over time of the phase, vector, or intensity of a complex OCT signal from differences, ratios, or correlation. The generation method of motion contrast data according to the present example will be described later.

Figure 14A:
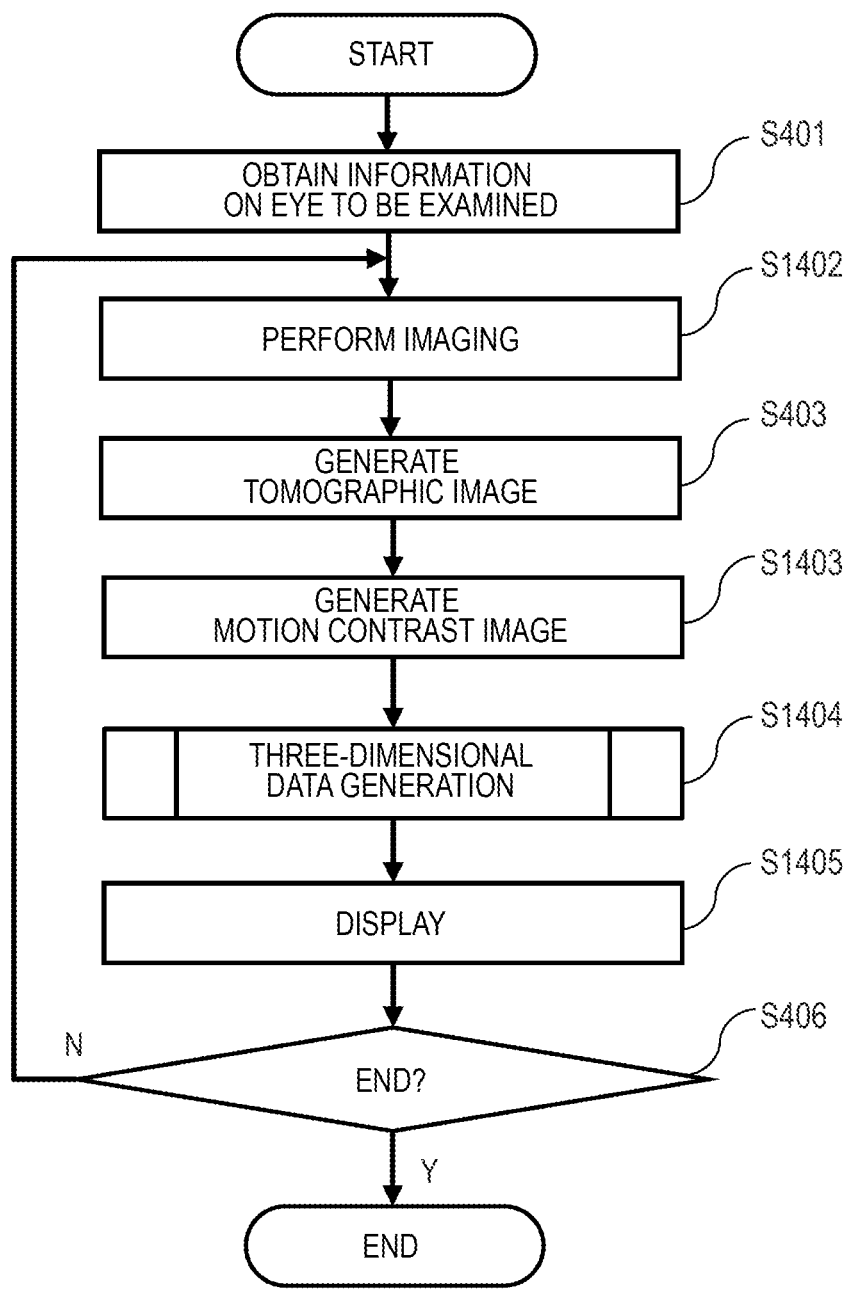
FIG. 14A is a flowchart illustrating an example of a flow of processing according to Example 3.
Figure 14B:
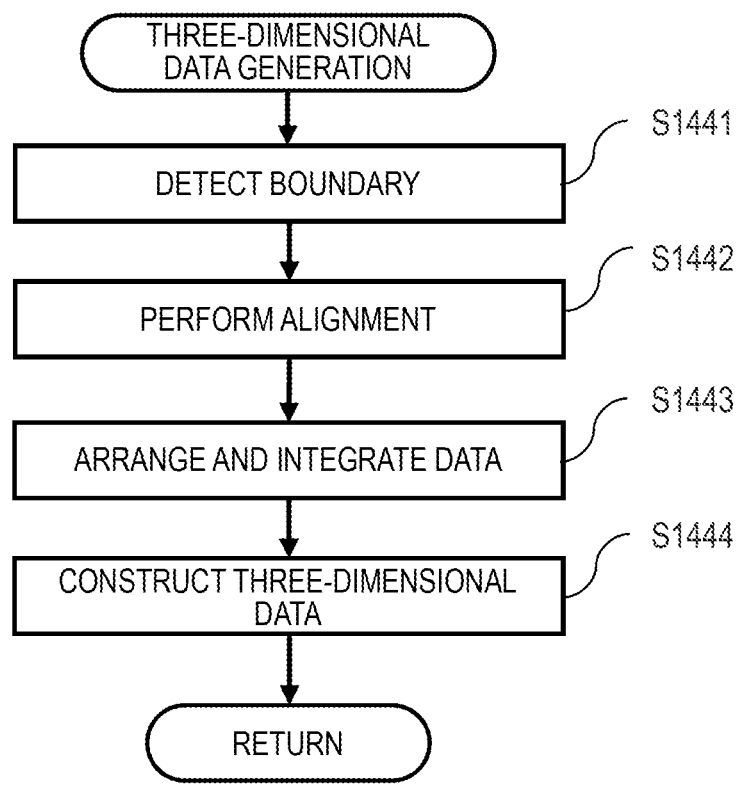
FIG. 14B is a flowchart illustrating an example of a flow of three-dimensional data generation processing according to Example 3.

Next, referring to FIG. 14A and FIG. 14B, a series of operational processing and three-dimensional-data generation processing according to the present example will be described. FIG. 14A is a flowchart illustrating a flow of the series of operational processing according to the present example, and FIG. 14B is a flowchart illustrating a flow of the three-dimensional data generation processing according to the present example. In the present example, for simplicity, a case will be described where the radial scan is performed as in Example 1. However, the circular scan may be combined as in Example 2. As for the series of operational processing according to the present example, since the eye to be examined information obtaining processing in step S401, the tomographic image generation processing in step S403, and the end determination process in step S406 are the same as each processing according to Example 1, the description will be omitted. Hereinafter, imaging processing in step S1402, motion contrast image generation processing in step S1403, three-dimensional data generation processing in step S1404, and display processing in step S1405 according to the present example will be described.

When the eye to be examined information is obtained in step S401, the processing proceeds to step S1402. In step S1402, in order to generate a motion contrast image from a tomographic image, the same scanning line is repeatedly scanned a plurality of times (at least twice or more) at the time when the drive controlling unit 180 controls the X scanner 107 and the Y scanner 110 to perform radial scan.

In step S403, the reconstructing unit 1901 generates a plurality of tomographic images for each scanning line, based on the interference signal obtained by repeatedly scanning the same scanning line. Note that, when generating a tomographic image used for generation of three-dimensional data, the reconstructing unit 1901 may generate a tomographic image obtained by additive averaging a plurality of tomographic images generated for the same scanning line. Additionally, one tomographic image of a plurality of tomographic images may be used as the tomographic image to be used for generation of three-dimensional data. When a plurality of tomographic images are generated, the processing proceeds to step S1403.

In step S1403, the motion contrast image generating unit 1906 generates a motion contrast image (motion contrast cross section image) based on the plurality of tomographic images generated for the same scanning line. First, the motion contrast image generating unit 1906 modifies the misalignment between the plurality of tomographic images that have been imaged in the same range (the same scanning line) of the eye to be examined. The modification method of the misalignment may be an arbitrary method. For example, the motion contrast image generating unit 1906 images the same range M times, and performs alignment for the tomographic images corresponding to the same location by utilizing a feature such as the fundus shape. Specifically, one of the M tomographic images is selected as a template, the similarity with the other tomographic images is obtained while changing the position and angle of the template, and the amount of misalignment with the template is obtained. Thereafter, the motion contrast image generating unit 1906 modifies each tomographic image based on the obtained amount of misalignment.

Next, the motion contrast image generating unit 1906 obtains a decorrelation value M (x, z) with the equation indicated in Math. 4 between two tomographic images in which the imaging time for each of the tomographic images is continuous to each other. Note that the two tomographic images used at the time of obtaining the decorrelation value may be tomographic images that have been imaged within a predetermined imaging time, and the imaging times do not need to be continuous to each other.

$$M(x, z) = 1 - 2 \times \frac{A(x, z) \times B(x, z)}{A(x, z)^2 + B(x, z)^2} \qquad \text{[Math. 4]}$$

Here, A (x, z) represents the intensity at a position (x, z) in a tomographic image A, and B (x, z) represents the intensity at the same position (x, z) in a tomographic image B. Note that a position coordinate x represents a position in the scanning direction (the transverse direction of a tomographic image), a position coordinate z represents a position in the depth direction (the longitudinal direction of the tomographic image), and the position coordinate x is not limited to a position in an x axial direction.

The decorrelation value M (x, z) has a value of 0 to 1, and the greater the difference between the two intensities, the larger the value of M (x, z). When M repeatedly obtained at the same position is 3 or more, the motion contrast image generating unit 1906 can obtain a plurality of decorrelation values M (x, z) at the same position (x, z). The motion contrast image generating unit 1906 can generate a final motion contrast image by performing statistical processing, such as maximum value operation and averaging operation of the plurality of obtained decorrelation values M (x, z). Note that, when the number M of repetitions is 2, the statistical processing, such as maximum value operation and averaging operation, is not performed, and the decorrelation value M (x, z) of the two tomographic images A and B serves as the value of motion contrast data at the position (x, z). The motion contrast image generating unit 1906 can generate a motion contrast image corresponding to a tomographic image by generating motion contrast data for each pixel position of the tomographic image, and arranging the motion contrast data to the corresponding pixel position.

The calculation equation of the motion contrast data indicated in Math. 4 tends to be sensitive to the influence of noise. For example, when there is noise in the non-signal portions of a plurality of tomographic images, and the values differ from each other, the decorrelation value will become higher, and the noise will also be superimposed on a motion contrast image. In order to avoid this, as the pre-processing, the motion contrast image generating unit 1906 can also consider the data of a tomographic image that is less than a predetermined threshold value to be noise, and can replace the data with zero. Accordingly, the motion contrast image generating unit 1906 can generate a motion contrast image with reduced influence of noise, based on the generated motion contrast data.

In step S1404, the signal processing unit 190 generates an intensity three-dimensional data based on tomographic images, and the three-dimensional data of motion contrast. The generation processing of the three-dimensional data will be described by referring to the flowchart in FIG. 14B. In the flowchart in FIG. 14B, since step S1441 is the same as step S441 in Example 1, the description will be omitted. In step S1441, when the detecting unit 1905 detects retinal boundary lines, the processing proceeds to step S1442.

In step S1442, the aligning unit 1902 performs the alignment of adjacent tomographic images. Note that the aligning unit 1902 performs the alignment described in Example 1 for the alignment in step S1442, and calculates the alignment parameter of the tomographic image corresponding to an adjacent scanning line in the radial scan. Additionally, since a motion contrast image is generated from a tomographic image, the alignment parameter obtained by using the tomographic image can be applied.

In step S1443, the data integrating unit 1903 arranges, in the three-dimensional space, tomographic images obtained by scanning in a radial manner, and performs integration of the data from the plurality of tomographic images. The data arrangement/integration in step S1443 may be performed in the same manner as the processing described in Example 1. Note that the data integrating unit 1903 can also apply, to a motion contrast image, the same processing as the integration processing performed on the tomographic image in each A-scan.

In step S1444, the data generating unit 1904 builds three-dimensional data based on the data obtained by arranging/integrating, in the three-dimensional space by the data integrating unit 1903, the tomographic images obtained by scanning in the radial manner and the motion contrast image. The building of the three-dimensional data in step S1444 may be performed by the same processing as the processing described in Example 1. Note that the data generating unit 1904 can also generate an estimated motion contrast image by the interpolation processing for a motion contrast image. Additionally, as in the processing described in Example 1, the data generating unit 1904 may perform the processing of generating a natural motion contrast image from a motion contrast image generated by interpolation by using a learned model.

Note that, for the training data for the learned model for generating a natural motion contrast image from a motion contrast image, the data generated by using the motion contrast image for the training data described in Example 1 can be used.

In step S1405, the controlling unit 191 displays, on the display unit 192, the tomographic image obtained by the radial scan, and the three-dimensional data generated from the motion contrast image. As in the example described for FIG. 11A, the image displayed on the display unit 192 can be the radially scanned tomographic images and the motion contrast image. Note that, although the motion contrast image can be displayed as is, a value equal to or more than a threshold value can be displayed by being superimposed on a tomographic image.

Additionally, as in the example described for FIG. 11B, the controlling unit 191 can display, on the display unit 192, an arbitrary tomographic image and a motion contrast image from the three-dimensional data built from the radial scan. Note that a value equal to or more than the threshold value can be displayed by being superimposed on a tomographic image, also for the motion contrast image of an arbitrary position.

Additionally, when a motion contrast image is being imaged, an OCTA image, which is a motion contrast front image of motion contrast data projected onto a two-dimensional plane, can also be generated and displayed. As for the generation of an OCTA image, the data generating unit 1904 can project, onto a two-dimensional plane, the motion contrast image corresponding to the range between a depth range upper end and a depth range lower end that are specified in the three-dimensional data of the motion contrast image to generate the OCTA image.

Specifically, based on the motion contrast image corresponding to the range between the depth range upper end and the depth range lower end that are specified in the three-dimensional data of the motion contrast image, processing, such as average intensity projection (AIP) or maximum intensity projection (MIP), is performed on the motion contrast image within the range. Accordingly, the data generating unit 1904 can generate the OCTA image, which is the front image of the motion contrast image. Note that the projection method at the time of generating the OCTA image is not limited to a projection method of the average value or the maximum value. The data generating unit 1904 may generate the OCTA image by using values, such as the minimum value, the median, the variance, the standard deviation, or the sum total.

The controlling unit 191 displays, on the display unit 192, the OCTA image generated by the data generating unit 1904. The OCTA image may be displayed by being superimposed on the fundus image 1110, or may be displayed by being switched with the En-Face image 1115.

As described above, the OCT apparatus according to the present example further includes the motion contrast image generating unit 1906 that generates a motion contrast image by using a plurality of tomographic images. Additionally, the signal processing unit 190 obtains a tomographic image group obtained by scanning the same location in a predetermined time period for a plurality of locations, and the motion contrast image generating unit 1906 generates a motion contrast image by using the obtained tomographic image group. Further, the aligning unit 1902 aligns a plurality of motion contrast images corresponding to a plurality of tomographic images with each other, and the data generating unit 1904 generates three-dimensional data by using the plurality of aligned motion contrast images. Additionally, the data generating unit 1904 generates the OCTA image, which is the motion contrast front image, from the three-dimensional data generated by using the motion contrast data. Note that the signal processing unit 190 may obtain the motion contrast image from an external apparatus, such as a server outside the controlling apparatus 200.

According to the configuration described above, in the present example, a plurality of tomographic images obtained by highly dense radial scan and a motion contrast images can be generated, and the misalignment of the motion contrast image can be reduced. Additionally, three-dimensional data can be generated from the aligned motion contrast image, and an arbitrary cross section can also be displayed. Accordingly, the state of the entire retina and the state of a blood vessel can be easily grasped with the data for single-time imaging.

Additionally, although the motion contrast data is obtained by calculating the decorrelation value of two values in the above-described method, the motion contrast data may be obtained based on the difference between the two values, or the motion contrast data may be obtained based on the ratio of the two values. In addition, the motion contrast data may be obtained based on the variance value of pixel values (intensity values) of a tomographic image. Further, in the above, although the final motion contrast data is obtained by obtaining the average value of a plurality of obtained decorrelation values, a plurality of decorrelation values, differences, the maximum value and the median of ratios, etc., may be used as the final motion contrast data.

Additionally, in the present example, the alignment, etc., for the motion contrast data obtained by the radial scan as in Example 1 has been described. On the other hand, for the alignment, etc., for the motion contrast data obtained by the radial scan and the circular scan as in Example 2, each processing may be performed as in Example 2. Note that, for the generation processing of motion contrast data and the generation processing of an OCTA image, those described in the present example can be applied.

Example 4

In Examples 1 to 3, the example has been described in which the drive controlling unit 180 controls the X scanner 107 and the Y scanner 110 to perform scanning in the radial manner, and further in the circle to obtain the tomographic images and the motion contrast image. Here, a tomographic image obtained by a common OCT apparatus does not correctly display a spatial shape. This will be described by referring to FIG. 15.

Figure 15:
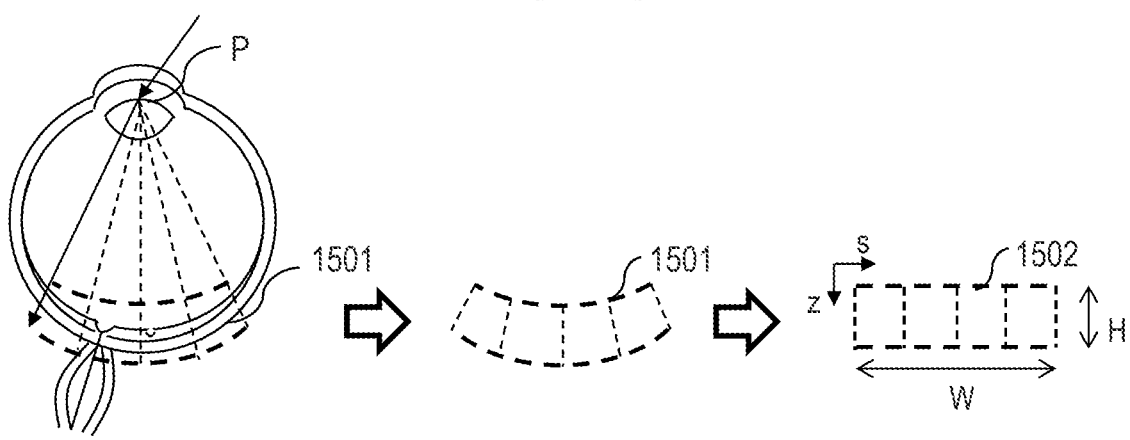
FIG. 15 illustrates an example of measuring light incident on an eye to be examined and tomographic image data according to Example 4.

FIG. 15 is a diagram for describing the display of a tomographic image obtained by a common OCT apparatus. Generally, a tomographic image is generated by arranging the data corresponding to the angle of a scan mirror in parallel. In FIG. 15, a point P indicates a pivot point, and light beam always passes through the point P in the center portion of a pupil. Here, the pivot point is a point corresponding to an incident point at which the measuring light is incident on the eye to be examined, and is a point conjugate with a scanning unit (scan mirror) of the measuring light. In FIG. 15, imaged data 1501 indicates an example of data corresponding to the angle of the scan mirror, and image data 1502 is an example of arranging and displaying the imaged data 1501 in parallel. That is, in a tomographic image imaged by the common OCT apparatus, the imaged data 1501 having a substantially fan-shape is displayed by being arranged in parallel as in the image data 1502. Therefore, the image data 1502 has a scanning distortion with respect to the actual shape of the eye to be examined.

Further, in the common OCT apparatus, when displaying a tomographic image, even in a case where the range (imaging range) to be scanned is different, the tomographic image is displayed by using the same aspect ratio. For example, even when there are tomographic images obtained by scanning two kinds of different ranges, i.e., a width W is 20 mm and a depth H is 5 mm, and the width W is 15 mm and the depth H is 5 mm, for the image data 1502, these tomographic images are displayed with the same aspect ratio in a screen region set to the display screen. In order to display a tomographic image close to an actual shape, it is necessary to set the pixel size in the transverse direction (s) and the longitudinal direction (z) to 1:1. Here, s for the transverse direction of a tomographic image indicates the direction along the scanning direction.

In the examples illustrated in FIG. 11A and FIG. 11B, as indicated by the aspect ratios 1141, 1142, and 1143, the aspect ratios of the tomographic images are not 1:1, and the depth direction is displayed stretched more than the transverse direction. This is because the scanning range (s) at the time of imaging can be imaged more widely than the depth range (z) in many cases, and when a tomographic image is displayed on a screen with a 1:1 aspect ratio, an inner retinal layer will be displayed thinly. Therefore, in order to pay attention to the structure of the inner retinal layer rather than the actual shape, there is an aspect ratio distortion with respect to the actual shape in a tomographic image obtained by and displayed on a common OCT apparatus.

Therefore, in the present example, modification processing is performed on tomographic images and motion contrast images obtained by an OCT apparatus, and three-dimensional data including three-dimensional tomographic images close to the actual shape and three-dimensional motion contrast images close to the actual shape is generated and displayed. Hereinafter, referring to FIG. 13 and FIG. 16 to FIG. 17B, the OCT apparatus according to the present example will be described by focusing on the differences from the OCT apparatus according to Example 3. Since each component of the OCT apparatus according to the present example is the same as each component of the OCT apparatus according to Example 3, except that the image modifying unit 1907 is further provided in the signal processing unit 190, the description will be omitted by using the same reference numerals.

FIG. 13 illustrates a schematic configuration example of the configuration of the signal processing unit 190 according to Examples 3 to 5. The signal processing unit 190 according to the present example is provided with the image modifying unit 1907, in addition to the reconstructing unit 1901, the aligning unit 1902, the data integrating unit 1903, the data generating unit 1904, the detecting unit 1905, and the motion contrast image generating unit 1906. Note that, although the analyzing unit 1908 is additionally illustrated in FIG. 13, this will be described in Example 5.

The image modifying unit 1907 performs actual shape modification processing on tomographic images and motion contrast images. Here, the actual shape modification processing is the processing of modifying the above-described scanning distortion with respect to the actual shape of the eye to be examined.

Figure 16:
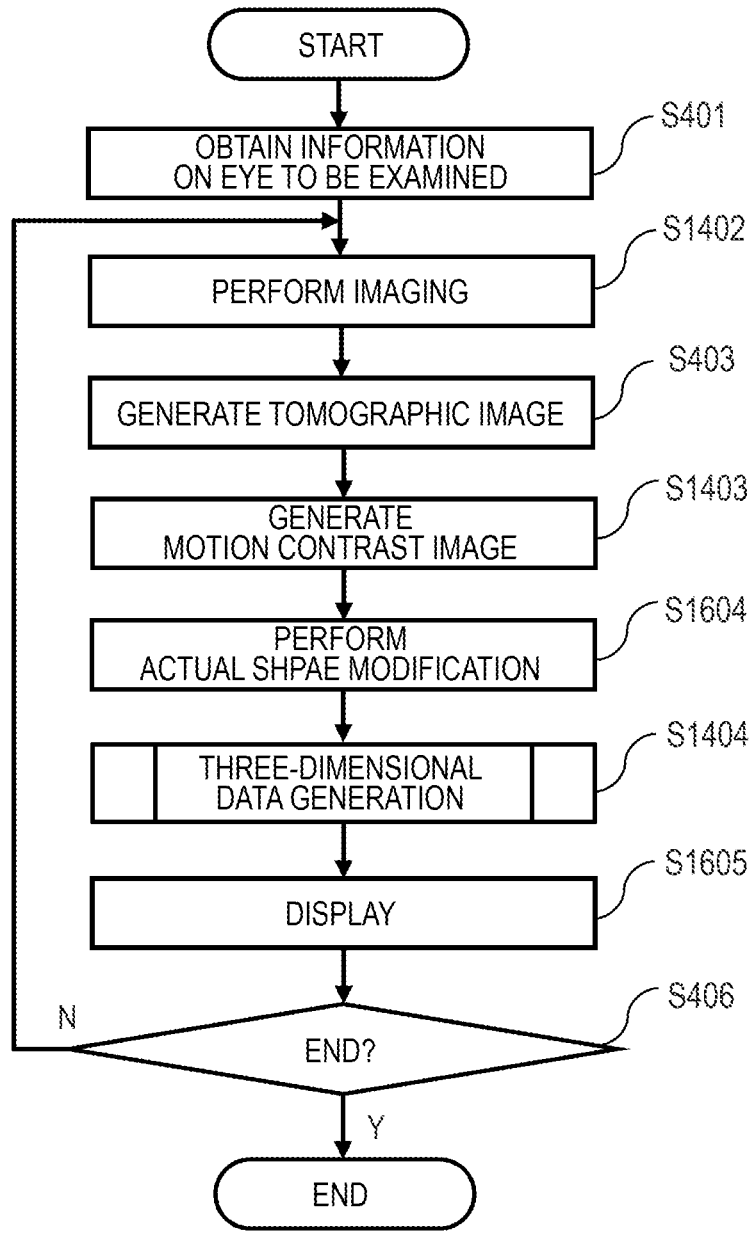
FIG. 16 is a flowchart illustrating an example of a flow of processing according to Example 4.

Next, referring to FIG. 16 to FIG. 17B, a series of operational processing according to the present example will be described. The series of operational processing according to the present example is the same as the series of operational processing according to Example 3, except that the actual shape modification processing is performed after the motion contrast generation processing, and an image after actual shape modification is displayed. Therefore, for the same processing as the processing in Example 3, the description will be omitted by using the same reference numerals. In step S1403, when the motion contrast image generating unit 1906 generates a motion contrast image, the processing proceeds to step S1604.

In step S1604, the image modifying unit 1907 performs the actual shape modification processing on the generated tomographic images and motion contrast image. The image modifying unit 1907 may use a known arbitrary method for the actual shape modification processing. The image modifying unit 1907 may use, for example, the actual shape modification methods as described in Japanese Patent Application Laid-Open No. 2012-148003, Japanese Patent Application Laid-Open No. 2012-147976, and Japanese Patent Application Laid-Open No. 2018-175258. Hereinafter, some examples of these kinds of actual shape modification processing will be described.

[Actual Shape Modification]

As described above, the shape of a fundus illustrated in a tomographic image is different from the shape of the fundus Ef in an actual eyeball. Specifically, although a normal tomographic image is generated by arranging the data corresponding to the angle of the scan mirror in parallel, these image data is actually the image data to be represented on polar coordinates centering on the center (pivot point) of scanning.

Therefore, in a first example of the actual shape modification processing, a tomographic image is modified by rearranging the data included in the tomographic image generated by arranging the data in two-dimensional coordinates on the polar coordinates centering on the pivot point. Especially, a tomographic image of the eye to be examined close to an actual shape is generated by modifying the tomographic image by using the optical information of the eye to be examined (the refractive index of a refraction element, and the relationship of the scanning angle with respect to the incident angle, etc.), and an optical path length. More specifically, the value obtained by dividing the optical distance from the pivot point to the retinal layer with the refractive index of the refraction element in the eye to be examined, and the angle formed by the line segment connecting a retina arrival point (irradiation position) of the measuring light in the fundus Ef to the pivot point, and a measuring light axis are obtained. Thereafter, using the obtained value and angle as parameters, the tomographic image is modified by using the polar coordinates having the pivot point as the origin. Note that, hereinafter, it is assumed that the brightness (pixel value) of a point on a B-scan image is represented by Image ($\theta i$, hj) by using an angle $\theta i$ of the scan mirror, and a difference hj between the retina and the optical path length of a reference optical system as the parameters.

Figure 17A:
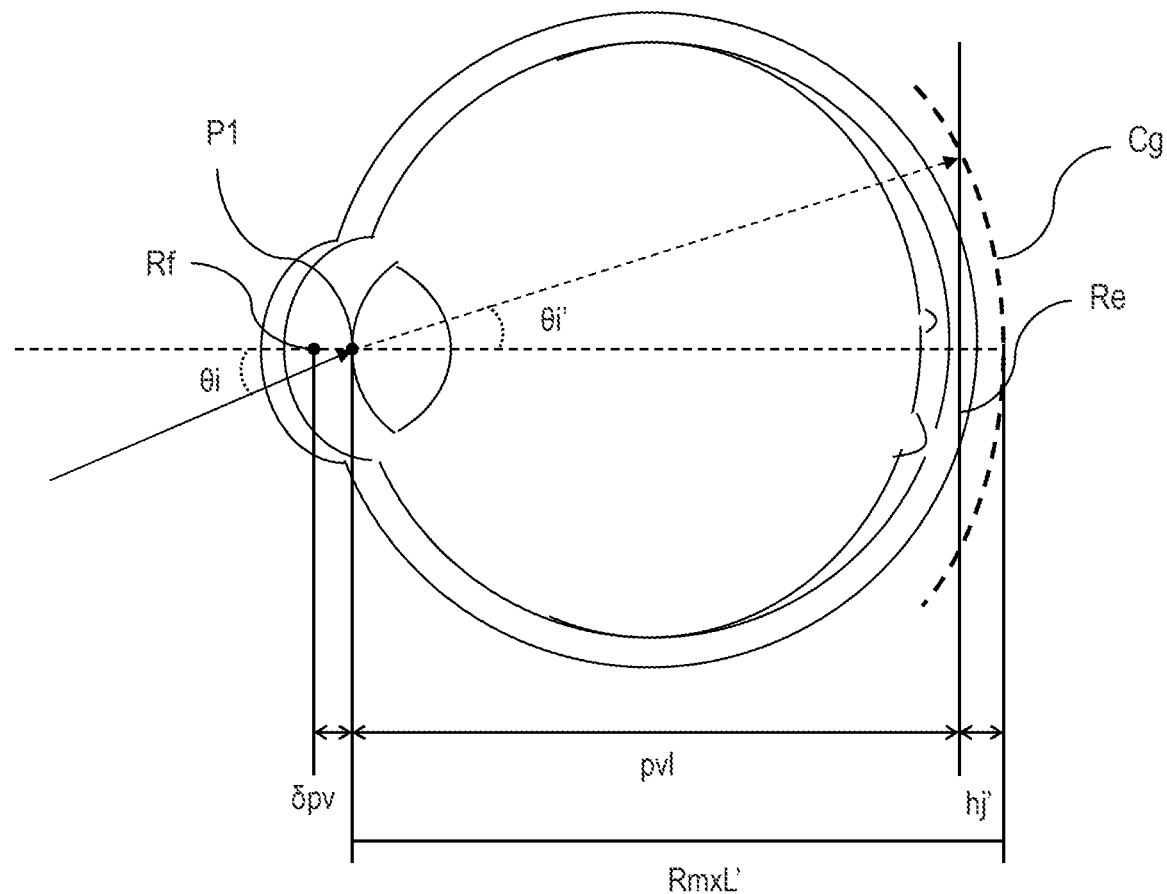
FIG. 17A is a diagram for describing actual shape modifying processing according to Example 4.

Hereinafter, the first example of the actual shape modification processing will be described by referring to FIG. 17A. In the example, the distance from a pivot point P1 to a coherence gate position Cg is RmxL, and the distance from the coherence gate position Cg to a retina Re is hj, and by dividing these with a refractive index Nvit of a vitreous body, the respective real distances (RmxL', hj') in the eye to be examined are calculated. In this case, a distance pvl from the pivot point P1 to a retina surface Re, corresponding to the ocular axial length of the eye to be examined, can be calculated as pvl=RmxL'−hj'.

Additionally, the angle $\theta i'$ formed by the line segment connecting the retina arrival point of the measuring light in the fundus Ef to the pivot point P1, and the measuring light axis is calculated. When the pivot point P1 matches a posterior principal plane of the eye to be examined, the angle $\theta i'$ can be $\theta i'$=a sin {(sin $\theta i$)/Nvit}.

On the other hand, when the pivot point P1 is different from the posterior principal plane, the angle $\theta i'$ is calculated by using a distance $\delta pv$ between the pivot point P1 and the posterior principal plane. In this case, when the focal point distance of the eye is feye, the distance from a corneal apex to an anterior principal point is ol, and the distance from the corneal apex to an imaging position (scan mirror conjugation position) of the pivot is inpv, $\delta pv$=(1/feye−1/(ol−ipv))^(−1)×Nvit. Note that the imaging position of the pivot corresponds to the pivot point.

The line segment connecting the arrival position of the measuring light on a coherence gate surface to a posterior principal point Rf of the eye to be examined, and the light passing through an iris surface and the pivot point P1 intersect on a surface that passes through a point at which an optical axis (eye axis) intersects the retina Re, and that is perpendicular to the optical axis. Therefore, when the distance between the pivot point P1 and the posterior principal point Rf is $\delta py$, the angle $\theta i'$ can be represented as $\theta i'$=a tan(($\delta pv$+pvl)×tan(ref$\theta i$)/pvl). Here, ref$\theta i$=a sin(sin($\theta i$)/Nvit).

By using the distances RmxL' and hj' and the angle $\theta i'$ calculated in this manner, the image data representing the actual shape with respect to orthogonal x and z coordinates can be represented as Image (x, z). Here, x=(RmxL'−hj')×sin($\theta i'$), and z=RmxL'−{(RmxL'−hj')×cos($\theta i'$)}.

With this processing, a tomographic image close to the actual shape of the eye to be examined can be generated. Note that, in the above-described processing, although it is assumed that the distance from the pivot point to the retina surface, corresponding to the ocular axial length of the eye to be examined, is obtained based on the optical path length of the reference light, the ocular axial length may be obtained by a separate apparatus.

Additionally, in a second example of the actual shape modification, based on a working distance that is the distance between a corneal surface of the eye to be examined and an objective lens surface, the position in the depth direction for each A-scan image in a B-scan image is modified. When the working distance is changed by a distance g, a distance f(g) from a rotation center (pivot point) of the measuring light seen from the retina to the retina, and a scanning angle $\theta(g)$ are changed. Here, the distance g indicates the distance from the design value of the working distance. On the other hand, since a scanning range W is almost unchanged, the scanning angle $\theta(g)$ seen from the retina has the relationship as the following equation.

$$f(g)\sin\left(\frac{\theta(g)}{2}\right) = \frac{W}{2} \qquad \text{[Math. 5]}$$

Here, when performing B-scan on the eye to be examined, the locus of the coherence gate position draws a fan-shaped arc. Therefore, in a case where a j-th A-scan in a B-scan is performed, when the coherence gate position corresponding to the A-scan is projected onto the z axis, an amount of change d(g) will be generated in the z axial direction with respect to the coherence gate position on the z axis. In this case, the amount of change d(g) can be calculated by the following equation.

$$d_j(g) = L(g)\left(1 - \cos\left(\frac{\theta(g)}{N-1}\left(\frac{N-1}{2} - j\right)\right)\right) \qquad \text{[Math. 6]}$$

Here, it is assumed that a scanner is rotated by $\theta(g)/(N-1)$ by using the scanning angle $\theta(g)$ in the case where the working distance is different from the design value by the distance g. Additionally, j is an integer satisfying N−1, and N is an A-scan number in a main scanning direction.

By multiplying the thus obtained dj(g) by a refractive index $n_h$ of the refraction element in the eye to be examined, and thereafter dividing by a pixel resolution, the modification value in the z axial direction for each A-scan position can be calculated.

Additionally, when alignment eccentricity of the measuring light occurs with respect to the eye to be examined, due to the alignment eccentricity, the incident angle of the measuring light on the retina and the optical path length of the measuring light are changed. For such a case, a third example of the actual shape modification processing that reduces the distortion of a tomographic image will be described. In the example, first, an amount of alignment eccentricity ox is obtained. The amount of alignment eccentricity δx can be obtained with a known arbitrary method. For example, the amount of alignment eccentricity δx may be obtained based on a cornea bright spot that appears in the anterior ocular segment image, or the amount of alignment eccentricity δx may be obtained based on the pattern of the iris of the eye to be examined in the anterior ocular segment image. Additionally, the amount of alignment eccentricity δx may be obtained based on the amount of movement of a motorized stage.

Then, by using the amount of alignment eccentricity δx, and the distance pvl from the pivot point to the retina surface, corresponding to the ocular axial length of the eye to be examined, an incident angle change amount δθ of the measuring light with respect to the retina due to the alignment eccentricity is obtained. Here, the incident angle change amount δθ can be obtained as δθ≈δx/pvl.

Additionally, the incident angle θi of the measuring light on the eye to be examined is obtained from the information on the angle of the scan mirror, and an optical path length change amount δz of the measuring light due to the alignment eccentricity is obtained from the amount of alignment eccentricity δx and the incident angle θi. Here, the optical path length change amount δz can be obtained as δz=δx×sin θi.

Based on the thus obtained incident angle change amount δθ and optical path length change amount δz, the actual shape modification can be performed on a tomographic image. More specifically, based on the optical path length change amount δz, the pixel position corresponding to each A-scan position can be moved in the depth direction. Additionally, based on the incident angle change amount δθ, the pixel position corresponding to each A-scan position can be rotated. Accordingly, the optical path length change amount δz caused by the alignment eccentricity, and the distortion of a tomographic image based on the incident angle change amount δθ can be reduced. Additionally, the actual shape modification processing described in the first example can also be performed on a tomographic image on which such modification of alignment eccentricity has been performed.

With these kinds of processing, the image modifying unit 1907 can modify the scanning distortion for the actual shape in a tomographic image. Particularly, in the second example, the differences in the shape of tomographic images due to the differences in the working distance between the eye to be examined and the objective lens can be modified, and in the third example, the distortion of a tomographic image due to the eye to be examined and the alignment eccentricity can be modified. Additionally, the actual shape modification processing can also be performed on a motion contrast image with the same processing.

Note that, in the above-described examples, the method for actual shape modification for tomographic images obtained by scanning in the x axial direction has been described. On the other hand, when performing radial scan, scanning is performed by deflecting the measuring light to the x axial direction and the y axial direction by the X scanner 107 and the Y scanner 110 according to the scanning direction as described above. Therefore, the actual shape modification processing can be performed by performing the same processing by using, for the scanning angle θ, a merged angle considering the scanning angle in the x axial direction and the scanning angle in the y axial direction. Note that, depending on the configurations/arrangements of the X scanner 107 and the Y scanner 110, the respective pivot points of the measuring light may be different from each other. Therefore, when performing the actual shape modification processing by using the merged angle considering the scanning angle in the x axial direction and the scanning angle in the y axial direction, the processing can be performed based on a pivot point closer to the corneal side (apparatus side) of the pivot points for the X scanner 107 and the Y scanner 110. Note that the position of the pivot point may be obtained from the apparatus configuration, or may be obtained according to an actual measurement value.

Additionally, the above-described method of actual shape modification may be applied as is to the scanning that deflects the measuring light only to the x axial direction or the y axial direction by the X scanner 107 and the Y scanner 110. However, for the scanning that deflects the measuring light only to the y axial direction, the modification can be performed in consideration of the position of the pivot point by the Y scanner 110 as described above.

When the actual shape modification processing ends, the processing proceeds to step S1404. In step S1404, as in Example 3, three-dimensional data is generated by the data generating unit 1904, etc. On this occasion, the three-dimensional data close to the actual shape of the eye to be examined can be generated by performing the processing based on tomographic images after the actual shape modification and motion contrast images. Note that, when the data generating unit 1904 performs the processing by using the above-described learned model, tomographic images included in the three-dimensional data formed by tomographic images on which the actual shape modification has been performed are used as training data. Accordingly, the three-dimensional data using the tomographic images after the actual shape modification can be input to the learned model to generate more natural three-dimensional data close to the actual shape.

When the three-dimensional data generation processing ends, the processing proceeds to step S1605. In step S1605, the controlling unit 191 displays, on the display unit 192, a tomographic image, etc., by using the generated three-dimensional data, etc. As described above, since the three-dimensional data is data close to the actual shape of the eye to be examined, the controlling unit 191 can display, on the display unit 192, an image close to the actual shape of the eye to be examined for a tomographic image arbitrarily cut from the three-dimensional data and a motion contrast image. Accordingly, the operator can confirm images with reduced scanning distortion.

Additionally, the controlling unit 191 can set the aspect ratio of length and width for tomographic images and motion contrast images to 1:1, and can display these images. Accordingly, the operator can confirm images with reduced aspect ratio distortion. Note that, although a screen example is not illustrated, the controlling unit 191 can display tomographic images and motion contrast images on the same screen as the display screen 1100 illustrated in FIG. 11A and FIG. 11B.

Figure 17B:
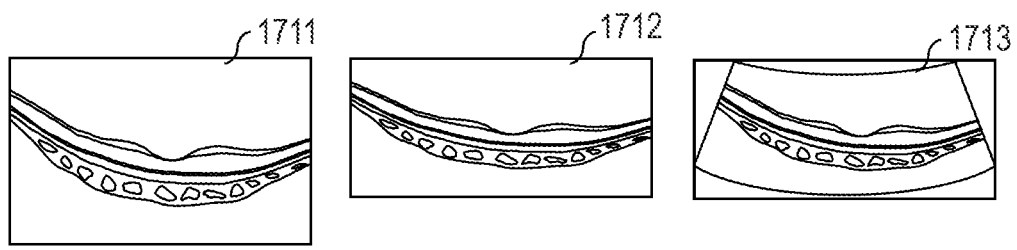
FIG. 17B is a diagram for describing the actual shape modifying processing according to Example 4.

FIG. 17B illustrates examples of tomographic images in which the scanning distortion and the aspect ratio distortion have been reduced by the above-described processing. In FIG. 17B, a tomographic image 1711 displayed by a common OCT apparatus, and a tomographic image 1712 obtained by modifying the aspect ratio of the pixels for the tomographic image 1711 to 1:1 are illustrated. Additionally, in FIG. 17B, a tomographic image 1713 obtained by reducing the aspect ratio distortion and the scanning distortion for the tomographic image 1711 is illustrated. By presenting such images, the operator can confirm images of the eye to be examined close to the actual shape of the eye to be examined.

As described above, the OCT apparatus according to the present example further includes the image modifying unit 1907. The signal processing unit 190 obtains a plurality of tomographic images obtained by radially scanning the measuring light on the eye to be examined, and corresponding to a plurality of locations of the eye to be examined, respectively, and the imaging parameter corresponding to each tomographic image. By using the obtained imaging parameter, the image modifying unit 1907 modifies the shape of a tomographic image corresponding to the imaging parameter. Additionally, the aligning unit 1902 aligns a plurality of shape-modified tomographic images with each other. In the present example, the imaging parameter includes at least one of the scanning information of the measuring light, the distance between the eye to be examined and the objective lens, and the amount of eccentricity of the eye to be examined with respect to the optical axis of the measuring light. Here, the scanning information of the measuring light may include the positions and lengths of the scanning lines of the radial scan, the angle of the scanning unit, etc. Additionally, for the imaging parameter, the imaging parameter set by the controlling unit 191 may be obtained, the imaging parameter may be obtained from an external apparatus of the controlling apparatus 200, or the imaging parameter may be obtained as an actual measurement value between the OCT apparatus and the eye to be examined.

For example, the image modifying unit 1907 modifies the shape of a tomographic image by using the scanning information of the measuring light, the position in the eye to be examined that is conjugate with the scanning unit scanning the measuring light, and the refractive index of the refraction element in the eye to be examined. Additionally, the image modifying unit 1907 may modify the shape of a tomographic image by using at least one of the distance between the eye to be examined and the objective lens, and the amount of eccentricity of the eye to be examined with respect to the optical axis of the measuring light.

According to the configuration described above, the OCT apparatus according to the present example can reduce the misalignment for a plurality of tomographic images close to an actual shape, by performing the actual shape modification processing on the plurality of tomographic images obtained by highly dense radial scan. Additionally, three-dimensional data can be generated by using the plurality of tomographic images for which the misalignment has been reduced, and an arbitrary cross section can be displayed. Accordingly, the operator can grasp the state of the entire retina as an image close to the actual shape. Therefore, the thickness and state of the entire retina, and the shape of the retina can be more accurately grasped with single-time imaging.

Note that the image modifying unit 1907 may modify the shape for a motion contrast image, and the aligning unit 1902 may perform the alignment for a plurality of motion contrast images. In this case, the misalignment can be reduced for the plurality of motion contrast images close to the actual shape, the three-dimensional data can be generated by using the plurality of motion contrast images for which the misalignment has been reduced, and an arbitrary cross section can be displayed. Accordingly, the operator can grasp the state of a blood vessel, etc., as an image close to the actual shape.

Note that, in the present example, although the example has been described in which the three-dimensional data generation processing is performed on the tomographic images and the motion contrast image on which the actual shape modification processing has been performed by the image modifying unit 1907, it is not limited to this. The image modifying unit 1907 can also perform the actual shape modification processing on the tomographic images and the motion contrast image, after performing the three-dimensional data generation.

Additionally, although the above-described method for actual shape modification processing has been described for performing the actual shape modification on two-dimensional tomographic images or motion contrast images, the same actual shape modification processing may be performed on three-dimensional data. Note that it is assumed that the brightness (pixel value) of a point on a three-dimensional image is represented by Image ($\theta xi$, $\theta yi$, hk) by using parameters, i.e., a scanning angle $\theta xi$ of the X scanner 107, a scanning angle $\theta yi$ of the Y scanner 110, and hk that is the difference between the retina and the optical path length of the reference optical system. In this case, the actual shape modification processing (step S1604) can be performed after the three-dimensional data generation processing (step S1404).

Here, it is assumed that the distance from the pivot point for the X scanner 107 to the coherence gate position is Rmxl, and the distance from the pivot point for the Y scanner 110 to the coherence gate position is Rmyl. In this case, the image data representing an actual shape with respect to orthogonal x, y, and z coordinates can be represented as Image (x, y, z), based on the same principle as the processing for the above-described two-dimensional tomographic images, etc. Here, $x=(RmxL'-hk')\times\cos(\theta yj')\times\sin(\theta xi')$, $y=(RmyL'-hk)\times\cos(\theta xi')\times\sin(\theta yj')$, and $z=RmxL'-\{(RmxL'-hk')\times\cos(\theta xi')\times(\theta yj')\}$.

Note that, although the differences from Example 3 has been mainly described in the present example, the actual shape modification processing according to the present example can also be applied to the OCT apparatuses according to Examples 1 and 2. Additionally, although the modification of the scanning distortion by the actual shape modification, and the modification of the aspect ratio distortion at the time of displaying are both performed in the present example, only one of them may be performed.

Example 5

In Examples 1 to 4, the examples has been described in which the tomographic images and the motion contrast image are obtained by scanning in the radial manner, and further in the circle, and the image modifying unit 1907 generates the three-dimensional data from the tomographic images and the motion contrast image on which the actual shape modification processing has been performed. In the present example, an example of performing analysis processing on these tomographic images or motion contrast image will be described.

Hereinafter, referring to FIG. 13 and FIG. 18 to FIG. 19B, an OCT apparatus according to the present example will be described by focusing on the differences from the OCT apparatus according to Example 4. Since each component of the OCT apparatus according to the present example is the same as each component of the OCT apparatus according to Example 4, except that the analyzing unit 1908 is further provided in the signal processing unit 190, the description will be omitted by using the same reference numerals.

FIG. 13 illustrates the schematic configuration example of the configuration of the signal processing unit 190 according to Examples 3 to 5. The signal processing unit 190 according to the present example is provided with the analyzing unit 1908, in addition to the reconstructing unit 1901, the aligning unit 1902, the data integrating unit 1903, the data generating unit 1904, the detecting unit 1905, the motion contrast image generating unit 1906, and the image modifying unit 1907.

The analyzing unit 1908 performs image analysis processing on tomographic images, motion contrast images, and three-dimensional data. The analyzing unit 1908 can, for example, measure the curvature of a boundary line and the thickness of the retina from a tomographic image and a three-dimensional tomographic image, and measure the blood vessel density and the vessel shape from a motion contrast image and a three-dimensional motion contrast image.

Next, referring to FIG. 18 to FIG. 19B, a series of operational processing according to the present example will be described. The series of operational processing according to the present example is the same as the series of operational processing according to Example 4, except for performing the analysis processing after the three-dimensional data generation processing, and displaying an analysis result, etc. Therefore, the same reference numerals will be used for the same processing as the processing in Example 4, and the description will be omitted. In step S1404, when the data generating unit 1904 generates three-dimensional data, the processing proceeds to step S1805.

In step S1805, the analyzing unit 1908 performs the image analysis processing on tomographic images, motion contrast images, and three-dimensional data, according to predefined settings or an instruction by the operator. As described above, the analyzing unit 1908 can analyze, for example, the curvature of a boundary line, the thickness of the retina, the blood vessel density, and the vessel shape. Note that the analyzing method may be a known arbitrary method.

As an example, a case will be described where the analyzing unit 1908 measures the curvature of the retina by using a tomographic image. In a tomographic image, the curvature of a boundary line of the layer (RPE) that is the target of shape analysis is calculated, with x coordinate on a horizontal axis, and z coordinate on a vertical axis. Here, although the x coordinate is on the horizontal axis, the coordinate is not limited to that along the x axis, and merely indicates the coordinate in the transverse direction of a tomographic image. A curvature κ can be obtained according to the equation in Math. 7 for each point of a boundary line. Whether it is convex upward or convex downward is found from the sign of the curvature κ, and the bending condition of a shape is found from the numerical magnitude. For example, in a case where it is assumed that + is convex upward, and − is convex downward, when the signs of the curvature are in a − region, a + region, and a − region in each tomographic image, a W shape is formed.

$$\kappa = \frac{\frac{d^2z}{dx^2}}{\left(1 + \left(\frac{dz}{dx}\right)\right)^{\frac{3}{2}}}$$ [Math. 7]

Note that, here, the case has been illustrated where the curvature is calculated with a boundary line in a tomographic image. However, the curvature calculation is not limited to this, and the three-dimensional curvature of a boundary line in the layer that is the target of shape analysis may be calculated from three-dimensional data.

Additionally, after the shape analysis of an analysis target, the analyzing unit 1908 can create a curvature map as an analysis map based on analysis results. In the curvature map, for example, the color of a location where the curvature per unit area is large can be expressed in darker colors, and the color of a location where the curvature per unit area is small can be expressed in lighter colors. Note that the colors set to the curvature map can be changed according to whether it is positive or negative based on a curvature value 0. Therefore, whether the retina shape is smooth, and whether the retina shape has an upward convex shape or a downward convex shape can be grasped by looking at the curvature map. Note that, in the analysis map, not only can the analysis results be expressed in colors, but also the numerical values of the analysis results can be displayed.

Figure 19A:
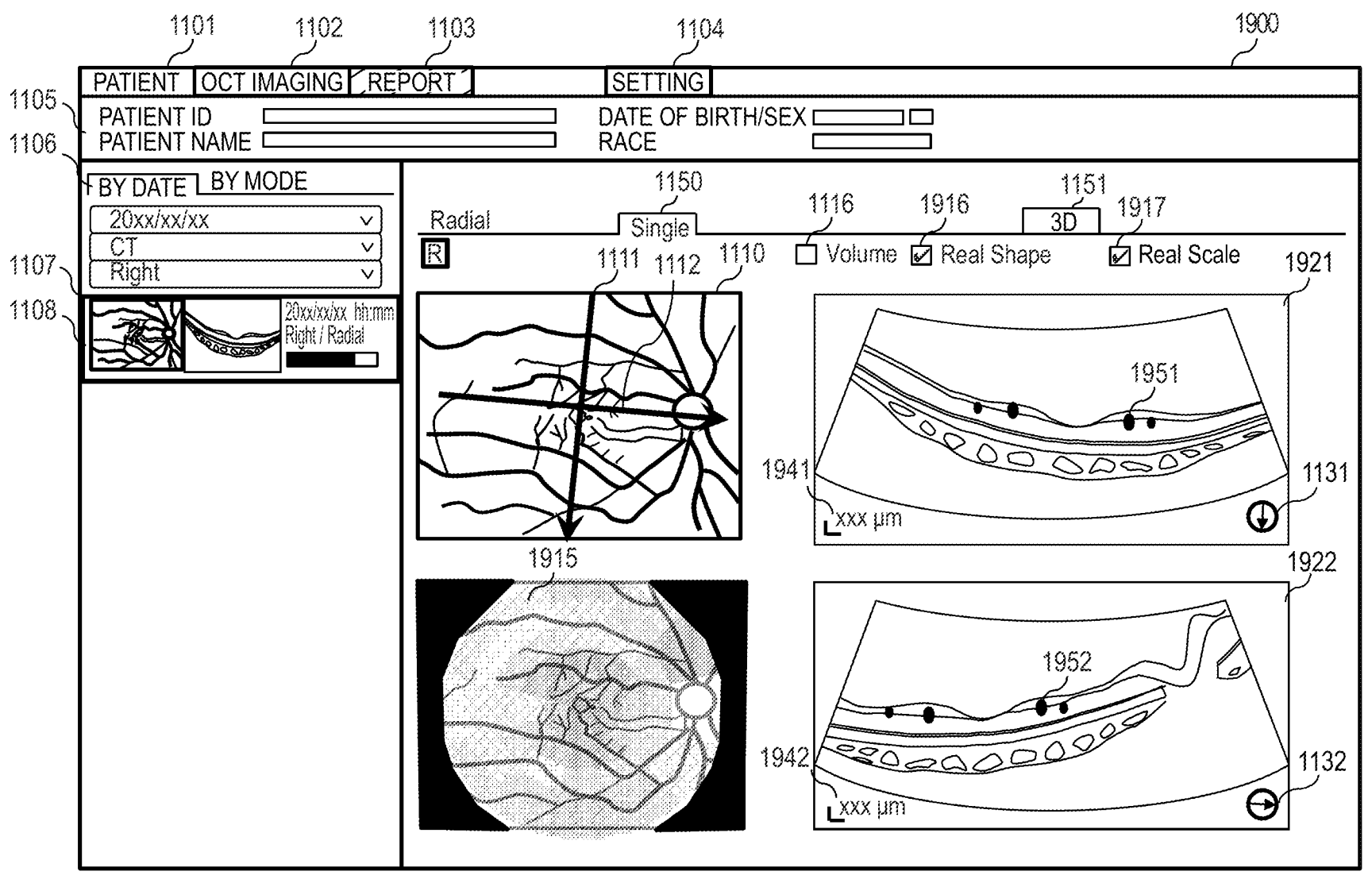

In step S1806, the controlling unit 191 displays, on the display unit 192, tomographic images, motion contrast images, three-dimensional data, and various map images serving as analysis results, etc. Regarding this, examples of a display screen 1900 according to the present example are illustrated in FIG. 19A and FIG. 19B. Note that, in FIG. 19A and FIG. 19B, the same reference numerals are used for the same items as the items illustrated in FIG. 11A and FIG. 11B, and the description will be omitted.

An analysis map 1915, check boxes 1916 and 1917, tomographic images 1921 and 1922, and aspect ratios 1941 and 1942 are illustrated in the display screen 1900 illustrated in FIG. 19A. The check box 1916 is the indication of a selecting unit for selecting whether or not to apply the actual shape modification processing for reducing the scanning distortion by the image modifying unit 1907. Additionally, the check box 1917 is the indication of a selecting unit for selecting whether or not to apply the aspect ratio distortion modification processing by the controlling unit 191. Note that the selecting unit to be displayed need not be the check box, and may be an arbitrary object, such as a right-click menu display or a list selection.

The tomographic images 1921 and 1922 are tomographic images in the case where the actual shape modification processing and the aspect ratio modification processing have been performed, respectively. Additionally, motion contrast images 1951 and 1952 are displayed in the tomographic images 1921 and 1922 in an overlapping manner. When the check box 1916 is selected, the image modifying unit 1907 may perform the actual shape modification processing on both the tomographic images and the motion contrast images as illustrated in the figure. Since the aspect ratios 1941 and 1942 indicate the aspect ratios of the displayed tomographic images, and the aspect ratio distortion is modified in the tomographic images 1921 and 1922, the aspect ratios are 1:1. Note that a selecting unit for selecting whether or not to apply the modification processing may be provided for each tomographic image.

The analysis map 1915 is a map image indicating the analysis results generated by the analyzing unit 1908. The map image may be, for example, the above-described curvature map, a layer thickness map, or a blood vessel density map. Note that, in the analysis map 1915, the values and colors are changed depending on whether or not the check box 1916 (RealShape) is checked. On the other hand, there is no change in the values and colors depending on whether or not the check box 1917 (RealScale) is checked. This is because the aspect ratio distortion is a problem in the display of a tomographic image, and when calculating an analysis value in a common OCT apparatus, the calculation is performed with numerical values not related to the aspect ratio in terms of calculation. On the other hand, since the shape of a tissue appearing in a tomographic image is changed depending on whether or not there is the actual shape modification processing, the analysis result is changed depending on whether or not the check box 1916 is checked. Therefore, for example, when performing analysis on the shape of the retina, in order to obtain a more correct analysis result, the actual shape modification processing can be performed. Note that, for the analysis processing, not only the curvature, but also the retina thickness, the blood vessel density, and the vessel shape, etc., can be each analyzed with respect to the data on which the actual shape modification processing has been performed.

Figure 19B:
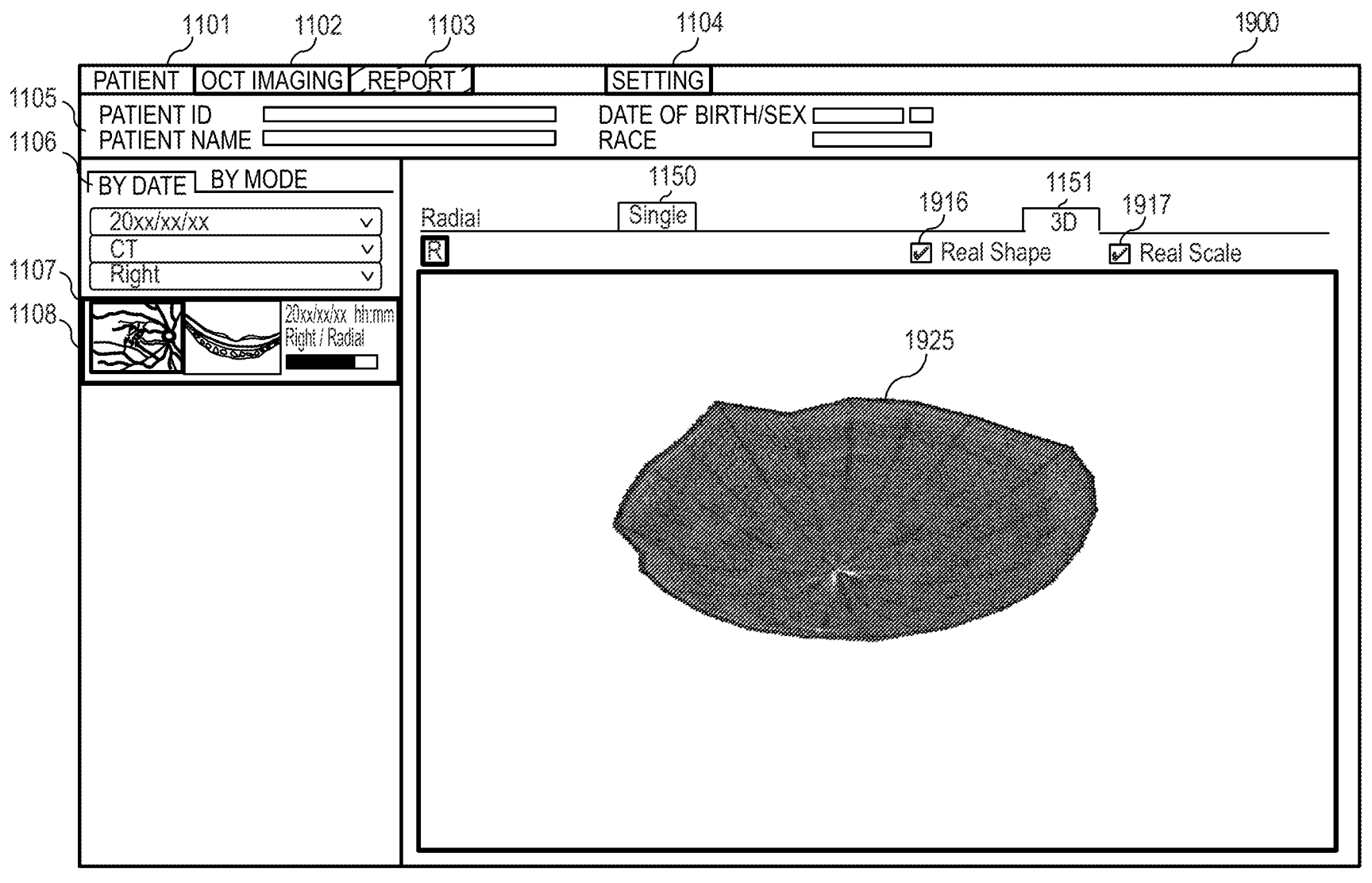

The display screen 1900 indicated in FIG. 19B is an example of the display screen that displays three-dimensional data. Three-dimensional volume data 1925 to which the actual shape modification processing and the aspect ratio modification processing have been applied is shown in the display screen 1900 illustrated in FIG. 19B. In FIG. 19B, an example of the case of displaying, for example, only the RPE layer is illustrated. Note that the above-described curvature value may be expressed with a color for the displayed three-dimensional data. That is, the analysis map 1915 may be simultaneous expression of the shape and color of the three-dimensional volume data 1925, instead of a two-dimensional plane.

As described above, the OCT apparatus according to the present example further includes the analyzing unit 1908 that performs the image analysis on the aligned tomographic images. According to such a configuration, the OCT apparatus according to the present example can perform the modification processing on a plurality of tomographic images obtained by highly dense radial scan, and motion contrast images, and can perform analysis on the data on which the modification has been performed. Accordingly, the operator can quantitatively grasp the state of the entire retina and the state of a blood vessel as numerical values close to the actual shape.

When the actual shape modification is performed on tomographic images and motion contrast images, more detailed analysis of the fundus shape can be performed. By generating a tomographic image and a motion contrast image close to the actual shape of the eye to be examined, for example, the analysis of the curvature radius and the layer thickness of the retinal layer in image diagnosis can be more appropriately performed.

Note that, although the differences from Example 4 has been mainly described in the present example, the actual shape modification processing according to the present example can also be applied to the OCT apparatuses according to Examples 1 to 3. Additionally, in the present example, although the analysis processing is performed on the images on which the actual shape modification processing has been performed, the target on which the analysis processing is to be performed is not limited to this. The analyzing unit 1908 may perform the analysis processing on tomographic images, motion contrast images, and three-dimensional data on which the actual shape modification processing has not been performed. Even in this case, the operator can quantitatively grasp the state of the entire retina and the state of a blood vessel.

[Modification 1]

In the above-described various examples, the examples have been described in which the three-dimensional data is generated from the tomographic images obtained by radially scanning the measuring light, or the tomographic images obtained by scanning in the radial manner and in the circle. On the other hand, correct three-dimensional data may be generated by combining tomographic images obtained by horizontally and vertically scanning (raster scanning) the measuring light, and tomographic images obtained by scanning the measuring light in the radial manner or in the circle. In this case, alignment can be performed by using, for the tomographic images obtained by horizontally and vertically scanning the measuring light, at the intersecting position, tomographic images obtained by other scanning. Note that the alignment processing, the data integration processing, the image interpolation processing in a case where the A-scan intervals in the main scanning direction and the sub-scanning direction are not isotropic, etc., can be performed similarly to the processing described in the above-described examples.

[Modification 2]

In the above-described various examples, the examples have been described in which the three-dimensional data is generated from the tomographic images obtained by radially scanning the measuring light, or the tomographic images obtained by scanning in the radial manner and in the circle. On the other hand, the three-dimensional data does not necessarily have to be generated and displayed, and data to be displayed may be densely imaged and radially scanned images. In other words, the check box 1116 may not be provided in the above-described examples. However, the three-dimensional data may be internally generated for analysis, etc., without being displayed. The generated three-dimensional data does not necessarily have to be saved, and may be generated at each execution.

[Modification 3]

In the above-described various examples, the examples have been illustrated in which the tomographic image as if it is actually imaged is generated from the tomographic image generated with interpolation by using the machine learning. On the other hand, the interpolation processing itself may be performed on three-dimensional data by using a machine learning model. For example, images can be generated by using generative adversarial networks (GAN). A GAN is formed by two neural networks, a generator and a discriminator. The generator intends to generate data similar to training data, and the discriminator discriminates whether data comes from training data or from generated models. In this case, learning is performed for a generation model such that, when a tomographic image of an arbitrary cross section position of three-dimensional data built from radial scan data, as illustrated by the tomographic image 911 in FIG. 9C, is input, a tomographic image as if it is actually imaged is generated. Accordingly, the data generating unit 1904 may generate, by using the learned model, three-dimensional data directly from a plurality of tomographic images obtained by radial scan, without performing the interpolation processing by itself.

Additionally, for the above-described CNN, the data corresponding to predetermined radial scan of three-dimensional data obtained by actual imaging may be used as input data for training data, and the output data may be the entire three-dimensional data obtained by actual imaging. Also in this case, the interpolation processing itself can be performed on the three-dimensional data by using the learned model. Note that, in this case, the data outside the imaging range of radial scan (outside the cylindrical range) can be deleted from the training data.

[Modification 4]

In the above-described various examples, overlapping processing may be performed by using radially scanned tomographic images imaged at a plurality of different times, and motion contrast images. For example, the alignment is performed on radially scanned tomographic images imaged for the same location at a plurality of different times. As the method for the alignment of a plurality of pieces of data imaged at different times, three-dimensional data is generated from radial scan by using any one method of the above-described methods. The alignment is performed by using the data of a characteristic XY surface in a plurality of pieces of three-dimensional data. In the alignment within the XY surface, the alignment may be performed in consideration of not only XY shift, but also rotation and distortion. Further, the alignment is performed also in a depth direction Z. In the depth direction Z, the alignment may be performed in B-scan units or A-scan unit. Thereafter, three-dimensional data with reduced noise can be generated by performing the overlapping processing. Note that, for example, additive averaging processing may be used for the overlapping processing.

[Modification 5]

In the above-described various examples, it may be enabled to output the aligned three-dimensional data in a format that can be printed with a 3D printer. For example, aligned tomographic images and motion contrast images, or aligned and thereafter actual shape-modified tomographic images and motion contrast images can be output in a RAW format, can be output in a format after surface rendering, or can be output in an STL (Standard Triangulated Language or Stereolithography) format, so as to allow printing with a 3D printer.

[Modification 6]

Note that, in Example 2, the alignment processing is performed on the tomographic images obtained by radial scan, based on the tomographic image obtained by circular scan. Here, the aligning unit 1902 may be configured so as to be able to switch the tomographic image used as the reference between a tomographic image (first tomographic image) obtained by the radial scan, and a tomographic image (second tomographic image) obtained by the circular scan. In this case, the aligning unit 1902 may switch between these kinds of alignment processings according to an instruction by the operator.

With such a configuration, when performing the alignment processing based on a tomographic image obtained by radial scan, since it is assumed that the intersecting position with other radial scan lines serves as the reference for alignment, it is considered that the accuracy of the alignment of the data in the center portion of the tomographic image becomes high. Therefore, when the center of the imaging range is set to the macular area, etc., since the data in the vicinity of the target (the macular area, etc.) to be examined is accurately aligned, it can be expected that the target such as the macular area can be more correctly confirmed.

On the other hand, when performing the alignment processing based on a tomographic image obtained by circular scan, since it is assumed that the intersecting position with the circular scan line serves as the reference for alignment, it is considered that the accuracy of alignment of the data in the periphery (end) of the tomographic image becomes high. Therefore, since the data of, for example, a blood vessel around the macular area is accurately aligned, it is expectable that the target such as the blood vessel can be more correctly confirmed.

As described above, the signal processing unit 190 according to the present modification obtains a plurality of first tomographic images obtained by radially scanning the measuring light on the eye to be examined, and corresponding to a plurality of locations of the eye to be examined, respectively. Additionally, the signal processing unit 190 obtains a second tomographic image obtained by scanning the measuring light in the circle on the eye to be examined, and corresponding to at least one location of the eye to be examined. In addition, the aligning unit 1902 aligns the plurality of first tomographic images and the second tomographic image with each other at least in the depth direction of the tomographic images. Especially, the aligning unit 1902 switches between the alignment based on the plurality of first tomographic images, and the alignment based on the second tomographic image, according to an instruction by the operator. With this configuration, since the aligning unit 1902 can switch the alignment processing, it can be expected that more correct three-dimensional data can be generated according to the target to be examined.

[Modification 7]

In the above-described various examples, data is generated by the interpolation processing for positions other than the tomographic images obtained by imaging and the motion contrast images. On the other hand, for example, the interference signal may be obtained also in a return period of the measuring light of the X scanner 107 and the Y scanner 110, and the data generating unit 1904 may use a tomographic image based on the interference signal, etc., as the data for interpolation. Here, the return period is a period for changing the angle of each scanner for moving the measuring light to the starting position for the next scanning line, after scanning the measuring light along a desired scanning line. Note that a thinned-out tomographic image obtained in the return period may be used as the data for interpolation.

In the above-described various examples, the aligned tomographic images, the motion contrast images, the three-dimensional data, the En-Face images, the OCTA images, and the analysis results are displayed on the display unit 192. On the other hand, the controlling apparatus 200 may be configured to transmit these pieces of data and analysis results to an external apparatus.

Additionally, in the above-described various examples, the SS-OCT optical system is used as the OCT optical system 100. However, as described above, OCT optical systems of other format may be used. For example, as the OCT, an SD-OCT may be used that uses an SLD as a light source, and performs imaging on interference light by using a spectroscope. Additionally, the present invention can also be applied to a Line-OCT (or an SS-Line-OCT) using line light. In addition, the present invention can also be applied to a Full Field-OCT (or an SS-Full Field-OCT) using area light. Further, the present invention can also be applied to the adaptive optics OCT (AO-OCT) using an adaptive optics system, or the polarization sensitive OCT (PS-OCT) for visualizing the information on polarization phase difference and depolarization.

Here, when using an optical system for the SD-OCT, since a spectroscope used for imaging disperses interference light in space by a diffraction grating, interference light crosstalk easily occurs between adjacent pixels of a line sensor. The interference light from a reflecting surface located at the depth position Z=Z0 is vibrated at a frequency of $Z0/\pi$ with respect to a wave number k. Therefore, as the depth position Z0 of the reflecting surface is increased (that is, farther away from the coherence gate position), the oscillation frequency of the interference light becomes higher, and the influence of the interference light crosstalk between the adjacent pixels of the line sensor is increased. Accordingly, in the SD-OCT, when attempting to image deeper positions, the decrease in sensitivity becomes significant. On the other hand, it is more advantageous for the SS-OCT that does not use a spectroscope than for the SD-OCT to image tomographic images at deeper positions. Additionally, in the spectroscope used in the SD-OCT, there is loss of the interference light due to a diffraction grating.

On the other hand, the sensitivity is easily improved in the SS-OCT when configured to perform, for example, differential detection of the interference light, without using a spectroscope. Therefore, in the SS-OCT, higher speed can be achieved with sensitivity equivalent to that in the SD-OCT, and by utilizing this high speed, wide-angle tomographic images can be obtained.

Although an optical fiber optical system that uses a coupler as a splitting unit is used in the above-described various examples and modifications, a spatial optical system that uses a collimator and a beam splitter may also be used. Further, the configuration of the OCT apparatus is not limited to the above-described configuration, and some of the components included in the OCT apparatus may be provided as separate components from the OCT apparatus. Note that, although a Mach-Zehnder interferometer is used, Michelson interferometer may be used.

Note that, although the controlling apparatus 200 is included in the OCT apparatus in the above-described various examples and modifications, the controlling apparatus 200 may be provided separately from the OCT apparatus. Additionally, when the controlling apparatus 200 is provided separately from the OCT apparatus, the controlling apparatus 200 and the OCT apparatus may be connected to each other with wires or wirelessly, and may be connected to each other via, for example, an arbitrary network such as the Internet.

Additionally, although the focus lens 114 is commonly used in the OCT optical system 100 and the SLO optical system 140 in the above-described various examples and modifications, it is not limited to this, and a focus lens may be separately provided in each of the optical systems. In addition, the control of the focus lens 114 by the drive controlling unit 180 may be such that the focus lens is driven based on the difference between the wavelength used by the light source 101, and the wavelength used by the light source 141. For example, when the focus lens is commonly provided to the OCT optical system 100 and the SLO optical system 140, when switching between the imaging using the SLO optical system 140 and the imaging using the OCT optical system 100 is performed, the drive controlling unit 180 may move the focus lens 114 according to the difference in the wavelengths. Additionally, in a case where the focus lens is provided in each of the optical systems, i.e., the OCT optical system 100 and the SLO optical system 140, when the focus lens of one of the optical systems is adjusted, the drive controlling unit 180 may move the focus lens of the other of the optical systems according to the difference in the wavelengths.

Further, the machine learning model used in the above-described various examples and modifications may be, for example, a capsule network (CapsNet). In this case, in a common neural network, by configuring each unit (each neuron) so as to output a scalar value, the neural network is configured so that, for example, spatial information relating to spatial positional relationships (relative positions) between features in an image is reduced. By this means, for example, learning can be performed in which the influence of local distortion or parallel displacement in an image is reduced. On the other hand, in a capsule network, each unit (each capsule) is configured so as to output spatial information as a vector, and for example, is configured so that spatial information is held. By this means, for example, learning can be performed in which spatial positional relationships (relative positions) between features in an image is taken into consideration.

Additionally, the display modes such as the GUIs described in the above-described various examples and modifications are not limited to those described above, and may be arbitrarily changed according to a desired configuration. For example, although it has been written for the display screen 1100, etc., that the OCTA front image, the tomographic images, and the depth ranges are displayed, motion contrast data may be displayed on a tomographic image. In this case, it is also enabled to confirm at which depths the motion contrast values are distributed. Additionally, colors may be used to display images, etc.

Additionally, in the above-described various examples and modifications, the controlling apparatus 200 obtains, by using the OCT optical system 100, the interference signal, the tomographic images generated by the reconstructing unit 1901, and the fundus front image generated by the signal processing unit 190, etc. However, the configuration in which the controlling apparatus 200 obtains these signals and images is not limited to this. For example, the controlling apparatus 200 may obtain these signals and data from a server and an imaging apparatus connected to the controlling apparatus 200 via a LAN, a WAN, or the Internet. In addition, when obtaining these signals and data, the controlling apparatus 200 may also obtain the imaging parameters including a scan pattern, the number of scanning lines, etc.

Note that, the learned models according to the above-described various examples and modifications can be provided in the controlling apparatus 200. These learned models, for example, may be constituted by a software module that is executed by a processor such as a CPU, an MPU, a GPU or an FPGA, or may be constituted by a circuit that serves a specific function such as an ASIC. Further, these learned models may be provided in a different apparatus such as a server that is connected to the controlling apparatus 200. In this case, the controlling apparatus 200 can use the learned models by connecting to the server or the like that includes the learned models through any network such as the Internet. The server that includes the learned models may be, for example, a cloud server, a FOG server, or an edge server. Further, the training data of the learned models is not limited to data obtained using the ophthalmic apparatus itself that performs the actual imaging, and according to a desired configuration, the training data may be data obtained using an ophthalmic apparatus of the same model, or may be data obtained using an ophthalmic apparatus of the same kind.

Note that, a GPU can perform efficient arithmetic operations by performing parallel processing of larger amounts of data. Therefore, in a case where learning is performed a plurality of times using a learning model such as deep learning, it is effective to perform processing with a GPU. Thus, a GPU may be used in addition to a CPU for processing by the controlling apparatus 200 that are an example of a learning unit (not illustrated). Specifically, when a learning program including the learning model is executed, learning is performed by the CPU and the GPU cooperating to perform arithmetic operations. Note that, with respect to the processing of the learning unit, arithmetic operations may be performed by only the CPU or the GPU. Further, a processing unit (estimating unit) that executes processing using the various learned models described above may also using a GPU, similarly to the learning unit. The learning unit may also include an error detecting unit and an updating unit (not illustrated). The error detecting unit obtains an error between output data that is output from the output layer of the neural network according to input data that is input to the input layer, and correct answer data. The error detecting unit may be configured to calculate an error between the output data from the neural network and the correct answer data using a loss function. Further, based on an error obtained by the error detecting unit, the updating unit updates combining weighting factors between nodes of the neural network or the like so that the error becomes small. The updating unit updates the combining weighting factors or the like using, for example, the error back-propagation method. The error back-propagation method is a method that adjusts combining weighting factors between the nodes of each neural network or the like so that the aforementioned error becomes small.

According to the above-described various embodiments and modifications of the present invention, misalignment between a plurality of pieces of data obtained by radial scan can be reduced.

Other Examples

The present invention can also be realized by a process in which program that realizes one or more functions according to the above examples and modifications is supplied to a system or an apparatus through a network or a storage medium, and a computer of the system or the apparatus reads and executes the program. The computer has one or a plurality of processors or circuits and, in order to read and execute computer-executable instructions, can include a plurality of computers separated from each other, a plurality of processors separated from each other, or a network of circuits.

Examples of the processor or circuit may include a central processing unit (CPU), a microprocessing unit (MPU), a graphics processing unit (GPU), an application specific integrated circuit (ASIC), or a field programmable gateway (FPGA). Further, examples of the processor or circuit may include a digital signal processor (DSP), a data flow processor (DFP) or a neural processing unit (NPU).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A medical image processing apparatus comprising:
    an obtaining unit configured to obtain (1) a plurality of tomographic images obtained by radially scanning measuring light on an eye to be examined, and corresponding to a plurality of locations of the eye to be examined, respectively, and (2) an imaging parameter corresponding to each tomographic image;
    a modifying unit configured to modify a shape of a tomographic image corresponding to the imaging parameter by using the imaging parameter;
    an aligning unit configured to align a plurality of shape-modified tomographic images with each other;
    a data generating unit configured to generate three-dimensional data using the plurality of aligned tomographic images; and
    a data integrating unit configured to define a pixel value of a position at which at least two tomographic images among the plurality of aligned tomographic images intersect in a three-dimensional space, using a value obtained by integrating pixel values of the position of the at least two tomographic images,
    wherein the data generating unit is configured to generate three-dimensional data using (1) the plurality of aligned tomographic images and (2) the pixel value defined by the data integrating unit.

2. The medical image processing apparatus according to claim 1, wherein the aligning unit is configured to align the plurality of shape-modified tomographic images with each other at least in a depth direction in the tomographic images.

3. The medical image processing apparatus according to claim 1, wherein the data integrating unit is configured to use, as the value obtained by integrating the pixel values, a statistic value of the pixel values of the at least two tomographic images at the position, or one pixel value of the pixel values.

4. The medical image processing apparatus according to claim 1, wherein the data generating unit is configured to generate data between the plurality of locations in the three-dimensional data by interpolation processing using two of the plurality of aligned tomographic images.

5. The medical image processing apparatus according to claim 1, wherein the data generating unit is configured to generate the three-dimensional data from the plurality of aligned tomographic images by using a learned model learned by using, as training data, three-dimensional data obtained by imaging an eye to be examined.

6. The medical image processing apparatus according to claim 1, wherein the data generating unit is configured to generate a front image obtained by projecting at least a part of data of the three-dimensional data onto a two-dimensional plane.

7. The medical image processing apparatus according to claim 6, wherein the tomographic images are intensity tomographic images or motion contrast tomographic images, and
    wherein the front image is an En-Face image or a motion contrast front image.

8. The medical image processing apparatus according to claim 1, wherein the imaging parameter includes at least one of scanning information of the measuring light, a distance between the eye to be examined and an objective lens, and an amount of eccentricity of the eye to be examined with respect to an optical axis of the measuring light.

9. The medical image processing apparatus according to claim 8, wherein the modifying unit is configured to modify the shape of the tomographic image by using the scanning information of the measuring light, a position in the eye to be examined that is conjugate with a scanning unit arranged to scan the measuring light, and a refractive index of a refraction element in the eye to be examined.

10. The medical image processing apparatus according to claim 8, wherein the modifying unit is configured to modify the shape of the tomographic image using at least one of the distance between the eye to be examined and the objective lens, and the amount of eccentricity of the eye to be examined with respect to the optical axis of the measuring light.

11. The medical image processing apparatus according to claim 1, wherein the obtaining unit is configured to further obtain a tomographic image obtained by scanning the measuring light in a circle on the eye to be examined, and corresponding to at least one location of the eye to be examined, and wherein the aligning unit is configured to align the plurality of tomographic images based on the tomographic image obtained by scanning the measuring light in the circle.

12. The medical image processing apparatus according to claim 1, further comprising:
   an image generating unit configured to generate a motion contrast image by using a plurality of tomographic images,
   wherein the obtaining unit is configured to obtain a tomographic image group obtained by scanning the same location in a predetermined time period for the plurality of locations, and
   wherein the image generating unit is configured to generate a motion contrast image using the tomographic image group.

13. The medical image processing apparatus according to claim 12, wherein the aligning unit is configured to align a plurality of motion contrast images corresponding to the plurality of tomographic images with each other, and
   wherein the medical image processing apparatus further comprises a data generating unit configured to generate three-dimensional data using the plurality of aligned motion contrast images.

14. The medical image processing apparatus according to claim 1, further comprising an analyzing unit configured to perform image analysis on the aligned tomographic images.

15. An optical coherence tomography apparatus comprising:
   the medical image processing apparatus according to claim 1; and
   an optical system including a scanning unit arranged to scan measuring light.

16. A medical image processing method comprising:
   obtaining (1) a plurality of tomographic images obtained by radially scanning measuring light on an eye to be examined, and corresponding to a plurality of locations of the eye to be examined, respectively, and (2) an imaging parameter corresponding to each tomographic image;
   modifying a shape of a tomographic image corresponding to the imaging parameter using the imaging parameter;
   aligning the plurality of shape-modified tomographic images with each other;
   generating three-dimensional data using the plurality of aligned tomographic images; and
   defining a pixel value of a position at which at least two tomographic images among the plurality of aligned tomographic images intersect in a three-dimensional space, using a value obtained by integrating pixel values of the position of the at least two tomographic images,
   wherein the generating includes generating three-dimensional data using (1) the plurality of aligned tomographic images and (2) the defined pixel value.

17. A non-transitory computer-readable medium storing a program, when executed by a computer, for causing the computer to perform the medical image processing method according to claim 16.

18. A medical image processing apparatus comprising:
   an obtaining unit configured to obtain (1) a plurality of tomographic images obtained by radially scanning measuring light on an eye to be examined, and corresponding to a plurality of locations of the eye to be examined, respectively, and (2) an imaging parameter corresponding to each tomographic image;
   a modifying unit configured to modify a shape of a tomographic image corresponding to the imaging parameter by using the imaging parameter; and
   an aligning unit configured to align a plurality of shape-modified tomographic images with each other,
   wherein the obtaining unit is configured to further obtain a tomographic image obtained by scanning the measuring light in a circle on the eye to be examined, and corresponding to at least one location of the eye to be examined, and
   wherein the aligning unit is configured to align the plurality of tomographic images based on the tomographic image obtained by scanning the measuring light in the circle.

* * * * *